US006521748B2

(12) United States Patent
Tang

(10) Patent No.: US 6,521,748 B2
(45) Date of Patent: Feb. 18, 2003

(54) **POLYNUCLEOTIDE ENCODING A MUTANT *RHODOTORULA GLUTINIS* TYROSINE AMMONIA LYASE POLYPEPTIDE**

(75) Inventor: Xiao-Song Tang, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/765,873

(22) Filed: Jan. 19, 2001

(65) Prior Publication Data

US 2001/0053847 A1 Dec. 20, 2001

Related U.S. Application Data

(63) Continuation-in-part of application No. 09/627,216, filed on Jul. 27, 2000, now Pat. No. 6,368,837.
(60) Provisional application No. 60/147,719, filed on Aug. 6, 1999.

(51) Int. Cl.$^7$ ............................ C07H 21/04; C12N 9/88
(52) U.S. Cl. ...................................... 536/23.2; 435/232
(58) Field of Search ........................ 536/23.2; 435/232

(56) References Cited

U.S. PATENT DOCUMENTS

| 4,681,850 A | 7/1987 | McGuire | 435/254 |
| 5,753,487 A | 5/1998 | Eigtved et al. | 435/232 |

FOREIGN PATENT DOCUMENTS

| EP | 0140707 A2 | 8/1985 |
| EP | 0 260919 A1 | 3/1988 |
| EP | 0278706 A2 | 8/1988 |
| EP | 0279665 A2 | 8/1988 |
| EP | 0477961 A2 | 1/1992 |
| EP | 321488 | 5/1997 |
| JP | 63 291583 A | 11/1988 |
| JP | 04330285 A2 | 11/1992 |
| JP | 05153978 | 6/1993 |
| WO | WO9307279 | 9/1987 |
| WO | WO 8912059 | 12/1989 |
| WO | WO/9312236 A | 6/1993 |
| WO | WO9732023 | 9/1997 |
| WO | WO9811205 | 3/1998 |
| WO | WO 01 11071 A2 | 2/2001 |

OTHER PUBLICATIONS

Database GenBank Accession No. X12702, Mar. 23, 1993.*
GenBank AJ010143, *Amanita muscaia* mRNA for phenylalanine ammonium lyase, Nehls, U. et al. (Jan. 29, 2002).
GenBank X75967, *Vitis vinifera*, Sparvoli, F. et al. (Jun. 9, 1994).
embl locus HTU2NFR, accession Z26250, *Helianthus tuberosus*, Hasenfratz, M. et al. (Oct. 28, 1996).
Genbank AF024634, *Petroselinum crispum*, Koopmann, E. et al. (Jan. 26, 1998).
Genbank ECU67186, *Eschscholzia californica*, Pauli, H. et al. (Mar. 6, 1998).
Genbank PSU67185, *Papaver somniferum*, Rosco et al. (Mar. 6, 1998).
embl accession Z17369, *Helianthus tuberosus*, Teutsch et al. (Jul. 6, 1993).
swissprot: accession Q43240,*Zinnie elegans*, Ye et al. (Jun. 15, 2002).
swissprot: accession P48522, *Catharanthus roseus*, Hotze et al. (Jun. 15, 2002).
swissprot accession O24312, *Populus tremuloides*, Ge et al. (Jun. 15, 2002).
swissprot accession Q43054, *Populus kitakamiensis*, Kawai et al. (Jun. 15, 2002).
swissprot accession Q96423, *Glycyrrhiza echinata*, Akashi et al. (Jun. 15, 2002).
swissprot accession Q42797, *Glycine max*, Schopfer et al. (Jun. 15, 2002).
embl accession Y09449, *Phaseolus vulgaris*, Nedelkina et al. (Jul. 7, 1999).
Koukol et al., *J. Biol. Chem.* 236:2692–2698 (1961).
Bandoni et al., *Phytochemistry* 7:205–207 (1968).
Ogata et al., *Agric. Biol. Chem.* 31:200–206 (1967).
Emes et al., *Can. J. Biochem* 48(5).:613–622 (1970).
Hanson and Havir In *The Enzymes*, 3rd ed.; Boyer, P., Ed.; Academic: New York, 1967; pp 75–167.
Hahlbrock et al., *Annu. Rev. Plant Phys. Plant Mol. Biol.* 40:347–369 (1989).
Edwards et al., *Proc. Natl. Acad. Sci., USA* 82:6731–6735 (1985).
Cramer et al., *Plant Mol. Biol.* 12:367–383 (1989).
Lois et al., *EMBO J.* 8:1641–1648 (1989).
Minami et al., *Eur. J. Biochem.* 185:19–25 (1989).
Anson et al., *Gene* 58:189–199 (1987).
Rasmussen & Oerum, *DNA Sequence*, 1:207–211 (1991).
Faulkner et al., *Gene* 143:13–20 (1994).
Langer et al., *Biochemistry* 36:10867–10871 (1997).
McKegney et al., *Phytochemistry* 41:1259–1263 (1996).
Bourget et al., *FEBS Lett.* 180:5–8 (1985).
Fritz et al., *J. Biol. Chem.* 251:4646–4650 (1976).
Koyama et al., *Clin. Chim. Acta*, 136:131–136 (1984).

(List continued on next page.)

*Primary Examiner*—Rebecca E. Prouty

(57) ABSTRACT

The present invention provides several methods for biological production of para-hydroxycinnamic acid (PHCA). The invention is also directed to the discovery of new fungi and bacteria that possess the ability to convert cinnamate to PHCA. The invention relates to developing of a new biocatalyst for conversion of glucose to PHCA by incorporation of the wild type PAL from the yeast *Rhodotorula glutinis* into *E. coli* underlining the ability of the wildtype PAL to convert tyrosine to PHCA. The invention is also directed to developing a new biocatalyst for conversion of glucose to PHCA by incorporation of the wildtype PAL from the yeast *Rhodotorula glutinis* plus the plant cytochrome P-450 and the cytochrome P-450 reductase into *E. coli*. In yet another embodiment, the present invention provides for the developing of a new biocatalyst through mutagenesis of the wild type yeast PAL which possesses enhanced tyrosine ammonia-lyase (TAL) activity.

1 Claim, 5 Drawing Sheets

OTHER PUBLICATIONS

Yamada et al., *Appl. Environ. Microbiol.* 42:773 (1981).
Hamilton et al., *Trends in Biotechnol.* 3:64–68 (1985).
Evans et al., *Microbial Biotechnology* 25:399–405 (1987).
Pierrel et al., *Eur. J. Biochem.* 224:835 (1994).
Urban et al., *Eur. J Biochem.* 222:843 (1994).
Cabello–Hurtado et al., *J. Biol. Chem.* 273:7260 (1998).
Teutsch et al., *Proc. Natl. Acad. Sci. USA* 90:4102 (1993).
Appert et al., *Eur. J. Biochem.* 225:491 (1994).
Havir et al., *Plant Physiol.* 48:130 (1971).
Hanson and Havir in *The Biochemistry of Plants;* Academic: New York, 1981; vol. 7, pp 577–625.
Rosco et al., Arch. Biochem. Biophys. 348(2) 369–377 (1997).
Shet et al., Proc. Natl. Acad. Sci. U.S.A. 90(7) 2890–2894 (1993).

Benveniste et al., "Purification and characterisation of the NADPH–cytochrome reductase from higher–plant microsomal fraction" Biochemical Journal, vol. 235, No. 2, 1986, pp 365–374 XP000943859.

Bocks, Sheila M., "Fungal metabolism, I. The transformation of coumarin, o–coumaric acid, and trans–cinnamic acid by *Aspergillus niger*", Phytochemistry (1967) 6(1), 127–30 XP002158519.

Gotor et al., Fungal and Bacterial Regioselective Hydroxylation of Pyrimidine Heterocycles Tetrahedron, NL Elsevier Science Publishers, Amsterdam, vol. 53. No. 18, May 5, 1997, pp. 6421–6432 XP004105640.

* cited by examiner

SEQUENCE LISTING

<160> NUMBER OF SEQ ID NOS: 38

<210> SEQ ID NO 1
<211> LENGTH: 34
<212> TYPE: DNA
<213> ORGANISM: primer

<400> SEQUENCE: 1
atagtagaat tcatggcacc ctcgctcgac tcga        34

<210> SEQ ID NO 2
<211> LENGTH: 29
<212> TYPE: DNA
<213> ORGANISM: primer

<400> SEQUENCE: 2
gagagactgc agagaggcag ccaagaacg        29

<210> SEQ ID NO 3
<211> LENGTH: 45
<212> TYPE: DNA
<213> ORGANISM: primer

<400> SEQUENCE: 3
gagagactcg agcccgggag atctcagacc aagtttactc atata        45

<210> SEQ ID NO 4
<211> LENGTH: 45
<212> TYPE: DNA
<213> ORGANISM: primer

<400> SEQUENCE: 4
gagagactcg agctgcagtc tagaactctt ttttcaatat tattg        45

<210> SEQ ID NO 5
<211> LENGTH: 22
<212> TYPE: DNA
<213> ORGANISM: primer

<400> SEQUENCE: 5
tagctctaga atggcaccct cg                                22

<210> SEQ ID NO 6
<211> LENGTH: 21
<212> TYPE: DNA
<213> ORGANISM: primer

<400> SEQUENCE: 6
aactgcagct aagcgagcat c                                 21

<210> SEQ ID NO 7
<211> LENGTH: 2151
<212> TYPE: DNA
<213> ORGANISM: Rhodotorula glutinis
<220> FEATURE:
<221> NAME/KEY: CDS
<222> LOCATION: (1)..(2151)

<400> SEQUENCE: 7

```
atg gca ccc tcg ctc gac tcg atc tcg cac tcg ttc gca aac ggc gtc      48
Met Ala Pro Ser Leu Asp Ser Ile Ser His Ser Phe Ala Asn Gly Val
1               5                   10                  15 gca tcc gca aag cag gct gtc aat ggc gcc tcg acc aac ctc gca gtc      96
Ala Ser Ala Lys Gln Ala Val Asn Gly Ala Ser Thr Asn Leu Ala Val
            20                  25                  30 gca ggc tcg cac ctg ccc aca acc cag gtc acg cag gtc gac atc gtc     144
Ala Gly Ser His Leu Pro Thr Thr Gln Val Thr Gln Val Asp Ile Val
        35                  40                  45 gag aag atg ctc gcc gcg ccg acc gac tcg acg ctc gaa ctc gac ggc     192
Glu Lys Met Leu Ala Ala Pro Thr Asp Ser Thr Leu Glu Leu Asp Gly
    50                  55                  60 tac tcg ctc aac ctc gga gac gtc gtc tcg gcc gcg agg aag ggc agg     240
Tyr Ser Leu Asn Leu Gly Asp Val Val Ser Ala Ala Arg Lys Gly Arg
65                  70                  75                  80 cct gtc cgc gtc aag gac agc gac gag atc cgc tca aag att gac aaa     288
Pro Val Arg Val Lys Asp Ser Asp Glu Ile Arg Ser Lys Ile Asp Lys
                85                  90                  95 tcg gtc gag ttc ttg cgc tcg caa ctc tcc atg agc gtc tac ggc gtc     336
Ser Val Glu Phe Leu Arg Ser Gln Leu Ser Met Ser Val Tyr Gly Val
            100                 105                 110 acg act gga ttt ggc gga tcc gca gac acc cgc acc gag gac gcc atc     384
Thr Thr Gly Phe Gly Gly Ser Ala Asp Thr Arg Thr Glu Asp Ala Ile
        115                 120                 125 tcg ctc cag aag gct ctc ctc gag cac cag ctc tgc ggt gtt ctc cct     432
Ser Leu Gln Lys Ala Leu Leu Glu His Gln Leu Cys Gly Val Leu Pro
    130                 135                 140 tcg tcg ttc gac tcg ttc cgc ctc ggc cgc ggt ctc gag aac tcg ctt     480
Ser Ser Phe Asp Ser Phe Arg Leu Gly Arg Gly Leu Glu Asn Ser Leu
145                 150                 155                 160 ccc ctc gag gtt gtt cgc ggc gcc atg aca atc cgc gtc aac agc ttg     528
Pro Leu Glu Val Val Arg Gly Ala Met Thr Ile Arg Val Asn Ser Leu
                165                 170                 175 acc cgc ggc cac tcg gct gtc cgc ctc gtc gtc ctc gag gcg ctc acc     576
Thr Arg Gly His Ser Ala Val Arg Leu Val Val Leu Glu Ala Leu Thr
            180                 185                 190
```

```
aac ttc ctc aac cac ggc atc acc ccc atc gtc ccc ctc cgc ggc acc      624
Asn Phe Leu Asn His Gly Ile Thr Pro Ile Val Pro Leu Arg Gly Thr
            195                 200                 205 atc tct gcg tcg ggc gac ctg tct cct ctc tcc tac att gca gcg gcc      672
Ile Ser Ala Ser Gly Asp Leu Ser Pro Leu Ser Tyr Ile Ala Ala Ala
    210                 215                 220 atc agc ggt cac ccg gac agc aag gtg cac gtc gtc cac gag ggc aag      720
Ile Ser Gly His Pro Asp Ser Lys Val His Val Val His Glu Gly Lys
225                 230                 235                 240 gag aag atc ctg tac gcc cgc gag gcg atg gcg ctc ttc aac ctc gag      768
Glu Lys Ile Leu Tyr Ala Arg Glu Ala Met Ala Leu Phe Asn Leu Glu
                245                 250                 255 ccc gtc gtc ctc ggc ccg aag gaa ggt ctc ggt ctc gtc aac ggc acc      816
Pro Val Val Leu Gly Pro Lys Glu Gly Leu Gly Leu Val Asn Gly Thr
            260                 265                 270 gcc gtc tca gca tcg atg gcc acc ctc gct ctg cac gac gct cac atg      864
Ala Val Ser Ala Ser Met Ala Thr Leu Ala Leu His Asp Ala His Met
        275                 280                 285 ctc tcg ctc ctc tcg cag tcg ctc acg gcc atg acg gtc gaa gcg atg      912
Leu Ser Leu Leu Ser Gln Ser Leu Thr Ala Met Thr Val Glu Ala Met
    290                 295                 300 gtc ggc cac gcc ggc tcg ttc cac ccc ttc ctt cac gac gtc acg cgc      960
Val Gly His Ala Gly Ser Phe His Pro Phe Leu His Asp Val Thr Arg
305                 310                 315                 320 cct cac ccg acg cag atc gaa gtc gcg gga aac atc cgc aag ctc ctc     1008
Pro His Pro Thr Gln Ile Glu Val Ala Gly Asn Ile Arg Lys Leu Leu
                325                 330                 335 gag gga agc cgc ttt gct gtc cac cat gag gag gag gtc aag gtc aag     1056
Glu Gly Ser Arg Phe Ala Val His His Glu Glu Glu Val Lys Val Lys
            340                 345                 350 gac gac gag ggc att ctc cgc cag gac cgc tac ccc ttg cgc acg tct     1104
Asp Asp Glu Gly Ile Leu Arg Gln Asp Arg Tyr Pro Leu Arg Thr Ser
        355                 360                 365 cct cag tgg ctc ggc ccg ctc gtc agc gac ctc att cac gcc cac gcc     1152
Pro Gln Trp Leu Gly Pro Leu Val Ser Asp Leu Ile His Ala His Ala
    370                 375                 380 gtc ctc acc atc gag gcc ggc cag tcg acg acc gac aac cct ctc atc     1200
Val Leu Thr Ile Glu Ala Gly Gln Ser Thr Thr Asp Asn Pro Leu Ile
385                 390                 395                 400 gac gtc gag aac aag act tcg cac cac ggc ggc aat ttc cag gct gcc     1248
Asp Val Glu Asn Lys Thr Ser His His Gly Gly Asn Phe Gln Ala Ala
                405                 410                 415 gct gtg gcc aac acc atg gag aag act cgc ctc ggg ctc gcc cag atc     1296
Ala Val Ala Asn Thr Met Glu Lys Thr Arg Leu Gly Leu Ala Gln Ile
            420                 425                 430 ggc aag ctc aac ttc acg cag ctc acc gag atg ctc aac gcc ggc atg     1344
Gly Lys Leu Asn Phe Thr Gln Leu Thr Glu Met Leu Asn Ala Gly Met
        435                 440                 445 aac cgc ggc ctc ccc tcc tgc ctc gcg gcc gaa gac ccc tcg ctc tcc     1392
Asn Arg Gly Leu Pro Ser Cys Leu Ala Ala Glu Asp Pro Ser Leu Ser
    450                 455                 460 tac cac tgc aag ggc ctc gac atc gcc gct gcg gcg tac acc tcg gag     1440
Tyr His Cys Lys Gly Leu Asp Ile Ala Ala Ala Ala Tyr Thr Ser Glu
465                 470                 475                 480 ttg gga cac ctc gcc aac cct gtg acg acg cat gtc cag ccg gct gag     1488
Leu Gly His Leu Ala Asn Pro Val Thr Thr His Val Gln Pro Ala Glu
                485                 490                 495 atg gcg aac cag gcg gtc aac tcg ctt gcg ctc atc tcg gct cgt cgc     1536
Met Ala Asn Gln Ala Val Asn Ser Leu Ala Leu Ile Ser Ala Arg Arg
            500                 505                 510
```

-continued

| | | |
|---|---|---|
| acg acc gag tcc aac gac gtc ctt tct ctc ctc ctc gcc acc cac ctc<br>Thr Thr Glu Ser Asn Asp Val Leu Ser Leu Leu Leu Ala Thr His Leu<br>              515                    520                  525 | | 1584 |
| tac tgc gtt ctc caa gcc atc gac ttg cgc gcg atc gag ttc gag ttc<br>Tyr Cys Val Leu Gln Ala Ile Asp Leu Arg Ala Ile Glu Phe Glu Phe<br>530                    535                  540 | | 1632 |
| aag aag cag ttc ggc cca gcc atc gtc tcg ctc atc gac cag cac ttt<br>Lys Lys Gln Phe Gly Pro Ala Ile Val Ser Leu Ile Asp Gln His Phe<br>545                  550                  555                  560 | | 1680 |
| ggc tcc gcc atg acc ggc tcg aac ctg cgc gac gag ctc gtc gag aag<br>Gly Ser Ala Met Thr Gly Ser Asn Leu Arg Asp Glu Leu Val Glu Lys<br>              565                    570                  575 | | 1728 |
| gtg aac aag acg ctc gcc aag cgc ctc gag cag acc aac tcg tac gac<br>Val Asn Lys Thr Leu Ala Lys Arg Leu Glu Gln Thr Asn Ser Tyr Asp<br>580                    585                  590 | | 1776 |
| ctc gtc ccg cgc tgg cac gac gcc ttc tcc ttc gcc gcc ggc acc gtc<br>Leu Val Pro Arg Trp His Asp Ala Phe Ser Phe Ala Ala Gly Thr Val<br>              595                    600                  605 | | 1824 |
| gtc gag gtc ctc tcg tcg acg tcg ctc tcg ctc gcc gcc gtc aac gcc<br>Val Glu Val Leu Ser Ser Thr Ser Leu Ser Leu Ala Ala Val Asn Ala<br>610                    615                  620 | | 1872 |
| tgg aag gtc gcc gcc gcc gag tcg gcc atc tcg ctc acc cgc caa gtc<br>Trp Lys Val Ala Ala Ala Glu Ser Ala Ile Ser Leu Thr Arg Gln Val<br>625                    630                  635                  640 | | 1920 |
| cgc gag acc ttc tgg tcc gcc gcg tcg acc tcg tcg ccc gcg ctc tcg<br>Arg Glu Thr Phe Trp Ser Ala Ala Ser Thr Ser Ser Pro Ala Leu Ser<br>              645                    650                  655 | | 1968 |
| tac ctc tcg ccg cgc act cag atc ctc tac gcc ttc gtc cgc gag gag<br>Tyr Leu Ser Pro Arg Thr Gln Ile Leu Tyr Ala Phe Val Arg Glu Glu<br>660                    665                  670 | | 2016 |
| ctt ggc gtc aag gcc cgc cgc gga gac gtc ttc ctc ggc aag caa gag<br>Leu Gly Val Lys Ala Arg Arg Gly Asp Val Phe Leu Gly Lys Gln Glu<br>              675                    680                  685 | | 2064 |
| gtg acg atc ggc tcg aac gtc tcc aag atc tac gag gcc atc aag tcg<br>Val Thr Ile Gly Ser Asn Val Ser Lys Ile Tyr Glu Ala Ile Lys Ser<br>690                    695                  700 | | 2112 |
| ggc agg atc aac aac gtc ctc ctc aag atg ctc gct tag<br>Gly Arg Ile Asn Asn Val Leu Leu Lys Met Leu Ala<br>705                    710                  715 | | 2151 |

<210> SEQ ID NO 8
<211> LENGTH: 716
<212> TYPE: PRT
<213> ORGANISM: Rhodotorula glutinis

<400> SEQUENCE: 8

Met Ala Pro Ser Leu Asp Ser Ile Ser His Ser Phe Ala Asn Gly Val
1                 5                    10                  15

Ala Ser Ala Lys Gln Ala Val Asn Gly Ala Ser Thr Asn Leu Ala Val
              20                    25                  30

Ala Gly Ser His Leu Pro Thr Thr Gln Val Thr Gln Val Asp Ile Val
        35                    40                  45

Glu Lys Met Leu Ala Ala Pro Thr Asp Ser Thr Leu Glu Leu Asp Gly
50                    55                    60

Tyr Ser Leu Asn Leu Gly Asp Val Val Ser Ala Ala Arg Lys Gly Arg
65                70                    75                  80

Pro Val Arg Val Lys Asp Ser Asp Glu Ile Arg Ser Lys Ile Asp Lys
              85                    90                  95

-continued

```
Ser Val Glu Phe Leu Arg Ser Gln Leu Ser Met Ser Val Tyr Gly Val
            100                 105                 110
Thr Thr Gly Phe Gly Gly Ser Ala Asp Thr Arg Thr Glu Asp Ala Ile
            115                 120                 125
Ser Leu Gln Lys Ala Leu Leu Glu His Gln Leu Cys Gly Val Leu Pro
            130                 135                 140
Ser Ser Phe Asp Ser Phe Arg Leu Gly Arg Gly Leu Glu Asn Ser Leu
145                 150                 155                 160
Pro Leu Glu Val Val Arg Gly Ala Met Thr Ile Arg Val Asn Ser Leu
                    165                 170                 175
Thr Arg Gly His Ser Ala Val Arg Leu Val Leu Glu Ala Leu Thr
            180                 185                 190
Asn Phe Leu Asn His Gly Ile Thr Pro Ile Val Pro Leu Arg Gly Thr
            195                 200                 205
Ile Ser Ala Ser Gly Asp Leu Ser Pro Leu Ser Tyr Ile Ala Ala Ala
            210                 215                 220
Ile Ser Gly His Pro Asp Ser Lys Val His Val His Glu Gly Lys
225                 230                 235                 240
Glu Lys Ile Leu Tyr Ala Arg Glu Ala Met Ala Leu Phe Asn Leu Glu
                    245                 250                 255
Pro Val Val Leu Gly Pro Lys Glu Gly Leu Gly Leu Val Asn Gly Thr
                    260                 265                 270
Ala Val Ser Ala Ser Met Ala Thr Leu Ala Leu His Asp Ala His Met
            275                 280                 285
Leu Ser Leu Leu Ser Gln Ser Leu Thr Ala Met Thr Val Glu Ala Met
            290                 295                 300
Val Gly His Ala Gly Ser Phe His Pro Phe Leu His Asp Val Thr Arg
305                 310                 315                 320
Pro His Pro Thr Gln Ile Glu Val Ala Gly Asn Ile Arg Lys Leu Leu
                    325                 330                 335
Glu Gly Ser Arg Phe Ala Val His His Glu Glu Val Lys Val Lys
            340                 345                 350
Asp Asp Glu Gly Ile Leu Arg Gln Asp Arg Tyr Pro Leu Arg Thr Ser
            355                 360                 365
Pro Gln Trp Leu Gly Pro Leu Val Ser Asp Leu Ile His Ala His Ala
            370                 375                 380
Val Leu Thr Ile Glu Ala Gly Gln Ser Thr Thr Asp Asn Pro Leu Ile
385                 390                 395                 400
Asp Val Glu Asn Lys Thr Ser His His Gly Gly Asn Phe Gln Ala Ala
                    405                 410                 415
Ala Val Ala Asn Thr Met Glu Lys Thr Arg Leu Gly Leu Ala Gln Ile
            420                 425                 430
Gly Lys Leu Asn Phe Thr Gln Leu Thr Glu Met Leu Asn Ala Gly Met
            435                 440                 445
Asn Arg Gly Leu Pro Ser Cys Leu Ala Ala Glu Asp Pro Ser Leu Ser
            450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
                    485                 490                 495
Met Ala Asn Gln Ala Val Asn Ser Leu Ala Leu Ile Ser Ala Arg Arg
            500                 505                 510
Thr Thr Glu Ser Asn Asp Val Leu Ser Leu Leu Leu Ala Thr His Leu
```

-continued

```
                       515                 520                 525
Tyr Cys Val Leu Gln Ala Ile Asp Leu Arg Ala Ile Glu Phe Glu Phe
                530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
                565                 570                 575
Val Asn Lys Thr Leu Ala Lys Arg Leu Glu Gln Thr Asn Ser Tyr Asp
            580                 585                 590
Leu Val Pro Arg Trp His Asp Ala Phe Ser Phe Ala Ala Gly Thr Val
            595                 600                 605
Val Glu Val Leu Ser Ser Thr Ser Leu Ser Leu Ala Ala Val Asn Ala
            610                 615                 620
Trp Lys Val Ala Ala Ala Glu Ser Ala Ile Ser Leu Thr Arg Gln Val
625                 630                 635                 640
Arg Glu Thr Phe Trp Ser Ala Ala Ser Thr Ser Ser Pro Ala Leu Ser
                645                 650                 655
Tyr Leu Ser Pro Arg Thr Gln Ile Leu Tyr Ala Phe Val Arg Glu Glu
                660                 665                 670
Leu Gly Val Lys Ala Arg Arg Gly Asp Val Phe Leu Gly Lys Gln Glu
                675                 680                 685
Val Thr Ile Gly Ser Asn Val Ser Lys Ile Tyr Glu Ala Ile Lys Ser
            690                 695                 700
Gly Arg Ile Asn Asn Val Leu Leu Lys Met Leu Ala
705                 710                 715

<210> SEQ ID NO 9
<211> LENGTH: 2151
<212> TYPE: DNA
<213> ORGANISM: mutant from Rhodotorula glutinis
<220> FEATURE:
<221> NAME/KEY: CDS
<222> LOCATION: (1)..(2151)

<400> SEQUENCE: 9 atg gca ccc tcg ctc gac tcg atc tcg cac tcg ttc gca aac ggc gtc      48
Met Ala Pro Ser Leu Asp Ser Ile Ser His Ser Phe Ala Asn Gly Val
1               5                   10                  15 gca tcc gca aag cag gct gtc aat ggc gcc tcg acc aac ctc gca gtc      96
Ala Ser Ala Lys Gln Ala Val Asn Gly Ala Ser Thr Asn Leu Ala Val
                20                  25                  30 gca ggc tcg cac ctg ccc aca acc cag gtc acg cag gtc gac atc gtc     144
Ala Gly Ser His Leu Pro Thr Thr Gln Val Thr Gln Val Asp Ile Val
            35                  40                  45 gag aag atg ctc gcc gcg ccg acc gac tcg acg ctc gaa ctc gac ggc     192
Glu Lys Met Leu Ala Ala Pro Thr Asp Ser Thr Leu Glu Leu Asp Gly
        50                  55                  60 tac tcg ctc aac ctc gga gac gtc gtc tcg gcc gcg agg aag ggc agg     240
Tyr Ser Leu Asn Leu Gly Asp Val Val Ser Ala Ala Arg Lys Gly Arg
65                  70                  75                  80 cct gtc cgc gtc aag gac agc gac gag atc cgc tca aag att gac aaa     288
Pro Val Arg Val Lys Asp Ser Asp Glu Ile Arg Ser Lys Ile Asp Lys
                85                  90                  95 tcg gtc gag ttc ttg cgc tcg caa ctc tcc atg agc gtc tac ggc gtc     336
Ser Val Glu Phe Leu Arg Ser Gln Leu Ser Met Ser Val Tyr Gly Val
                100                 105                 110 acg act gga ttt ggc gga tcc gca gac acc cgc acc gag gac gcc atc     384
Thr Thr Gly Phe Gly Gly Ser Ala Asp Thr Arg Thr Glu Asp Ala Ile
```

```
                 115                 120                      125
tcg ctc cag aag gct ctc ctc gag cac cag ctc tgc ggt gtt ctc cct      432
Ser Leu Gln Lys Ala Leu Leu Glu His Gln Leu Cys Gly Val Leu Pro
    130                 135                 140 tcg tcg ttc gac tcg ttc cgc ctc ggc cgc ggt ctc gag aac tcg ctt      480
Ser Ser Phe Asp Ser Phe Arg Leu Gly Arg Gly Leu Glu Asn Ser Leu
145                 150                 155                 160 ccc ctc gag gtt gtt cgc ggc gcc atg aca atc cgc gtc aac agc ttg      528
Pro Leu Glu Val Val Arg Gly Ala Met Thr Ile Arg Val Asn Ser Leu
                165                 170                 175 acc cgc ggc cac tcg gct gtc cgc ctc gtc gtc ctc gag gcg ctc acc      576
Thr Arg Gly His Ser Ala Val Arg Leu Val Val Leu Glu Ala Leu Thr
            180                 185                 190 aac ttc ctc aac cac ggc atc acc ccc atc gtc ccc ctc cgc ggc acc      624
Asn Phe Leu Asn His Gly Ile Thr Pro Ile Val Pro Leu Arg Gly Thr
        195                 200                 205 atc tct gcg tcg ggc gac ctc tct cct ctc tcc tac att gca gcg gcc      672
Ile Ser Ala Ser Gly Asp Leu Ser Pro Leu Ser Tyr Ile Ala Ala Ala
    210                 215                 220 atc agc ggt cac ccg gac agc aag gtg cac gtc gtc cac gag ggc aag      720
Ile Ser Gly His Pro Asp Ser Lys Val His Val Val His Glu Gly Lys
225                 230                 235                 240 gag aag atc ctg tac gcc cgc gag gcg atg gcg ctc ttc aac ctc gag      768
Glu Lys Ile Leu Tyr Ala Arg Glu Ala Met Ala Leu Phe Asn Leu Glu
                245                 250                 255 ccc gtc gtc ctc ggc ccg aag gag ggt ctc ggt ctc gtc aac ggc acc      816
Pro Val Val Leu Gly Pro Lys Glu Gly Leu Gly Leu Val Asn Gly Thr
            260                 265                 270 gcc gtc tca gca tcg atg gcc acc ctc gct ctg cac gac gca cac atg      864
Ala Val Ser Ala Ser Met Ala Thr Leu Ala Leu His Asp Ala His Met
        275                 280                 285 ctc tcg ctc ctc tcg cag tcg ctc acg gcc atg acg gtc gaa gcg atg      912
Leu Ser Leu Leu Ser Gln Ser Leu Thr Ala Met Thr Val Glu Ala Met
    290                 295                 300 gtc ggc cac gcc ggc tcg ttc cac ccc ttc ctt cac gac gtc acg cgc      960
Val Gly His Ala Gly Ser Phe His Pro Phe Leu His Asp Val Thr Arg
305                 310                 315                 320 cct cac ccg acg cag atc gaa gtc gcg gga aac atc cgc aag ctc ctc     1008
Pro His Pro Thr Gln Ile Glu Val Ala Gly Asn Ile Arg Lys Leu Leu
                325                 330                 335 gag gga agc cgc ttt gct gtc cac cat gag gag gag gtc aag gtc aag     1056
Glu Gly Ser Arg Phe Ala Val His His Glu Glu Glu Val Lys Val Lys
            340                 345                 350 gac gac gag ggc att ctc cgc cag gac cgc tac ccc ttg cgc acg tct     1104
Asp Asp Glu Gly Ile Leu Arg Gln Asp Arg Tyr Pro Leu Arg Thr Ser
        355                 360                 365 cct cag tgg ctc ggc ccg ctc gtc agc gac ctc att cac gcc cac gcc     1152
Pro Gln Trp Leu Gly Pro Leu Val Ser Asp Leu Ile His Ala His Ala
    370                 375                 380 gtc ctc acc atc gag gcc ggc cag tcg acg acc gac aac cct ctc atc     1200
Val Leu Thr Ile Glu Ala Gly Gln Ser Thr Thr Asp Asn Pro Leu Ile
385                 390                 395                 400 gac gtc gag aac aag act tcg cac cac ggc ggc aat ttc cag gct gcc     1248
Asp Val Glu Asn Lys Thr Ser His His Gly Gly Asn Phe Gln Ala Ala
                405                 410                 415 gct gtg gcc aac acc atg gag aag act cgc ctc ggg ctc gcc cag atc     1296
Ala Val Ala Asn Thr Met Glu Lys Thr Arg Leu Gly Leu Ala Gln Ile
            420                 425                 430 ggc aag ctc aac ttc acg cag ctc acc gag atg ctc aac gcc ggc atg     1344
```

-continued

```
                Gly Lys Leu Asn Phe Thr Gln Leu Thr Glu Met Leu Asn Ala Gly Met
                        435                 440                 445 aac cgc ggc ctc ccc tcc tgc ctc gcg gcc gaa gac ccc tcg ctc tcc      1392
Asn Arg Gly Leu Pro Ser Cys Leu Ala Ala Glu Asp Pro Ser Leu Ser
        450                 455                 460 tac cac tgc aag ggc ctc gac atc gcc gct gcg gcg tac acc tcg gag      1440
Tyr His Cys Lys Gly Leu Asp Ile Ala Ala Ala Ala Tyr Thr Ser Glu
465                 470                 475                 480 ttg gga cac ctc gcc aac cct gtg acg acg cat gtc cag ccg gct gag      1488
Leu Gly His Leu Ala Asn Pro Val Thr Thr His Val Gln Pro Ala Glu
                485                 490                 495 atg gcg aac cag gcg gtc aac tcg ctt gcg ctc atc tcg gct cgt cgc      1536
Met Ala Asn Gln Ala Val Asn Ser Leu Ala Leu Ile Ser Ala Arg Arg
            500                 505                 510 acg acc gag tcc aac gac gtc ctt tct ctc ctc gcc acc cac ctc          1584
Thr Thr Glu Ser Asn Asp Val Leu Ser Leu Leu Leu Ala Thr His Leu
        515                 520                 525 tac tgc gtt ctc caa gcc atc gac ttg cgc gcg acc gag ttc gag ttc      1632
Tyr Cys Val Leu Gln Ala Ile Asp Leu Arg Ala Thr Glu Phe Glu Phe
    530                 535                 540 aag aag cag ttc ggc cca gcc atc gtc tcg ctc atc gac cag cac ttt      1680
Lys Lys Gln Phe Gly Pro Ala Ile Val Ser Leu Ile Asp Gln His Phe
545                 550                 555                 560 ggc tcc gcc atg acc ggc tcg aac ctg cgc gac gag ctc gtc gag aag      1728
Gly Ser Ala Met Thr Gly Ser Asn Leu Arg Asp Glu Leu Val Glu Lys
                565                 570                 575 gtg aac aag acg ctc gcc aag cgc ctc gag cag acc aac tcg tac gac      1776
Val Asn Lys Thr Leu Ala Lys Arg Leu Glu Gln Thr Asn Ser Tyr Asp
            580                 585                 590 ctc gtc ccg cgc tgg cac gac gcc ttc tcc ttc gcc gcc ggc acc gtc      1824
Leu Val Pro Arg Trp His Asp Ala Phe Ser Phe Ala Ala Gly Thr Val
        595                 600                 605 gtc gag gtc ctc tcg tcg acg tcg ctc tcg ctc gcc gcc gtc aac gcc      1872
Val Glu Val Leu Ser Ser Thr Ser Leu Ser Leu Ala Ala Val Asn Ala
    610                 615                 620 tgg aag gtc gcc gcc gcc gag tcg gcc atc tcg ctc acc cgc caa gtc      1920
Trp Lys Val Ala Ala Ala Glu Ser Ala Ile Ser Leu Thr Arg Gln Val
625                 630                 635                 640 cgc gag acc ttc tgg tcc gcc gcg tcg acc tcg tcg ccc gcg ctc tcg      1968
Arg Glu Thr Phe Trp Ser Ala Ala Ser Thr Ser Ser Pro Ala Leu Ser
                645                 650                 655 tac ctc tcg ccg cgc act cag atc ctc tac gcc ttc gtc cgc gag gag      2016
Tyr Leu Ser Pro Arg Thr Gln Ile Leu Tyr Ala Phe Val Arg Glu Glu
            660                 665                 670 ctt ggc gtc aag gcc cgc cgc gga gac gtc ttc ctc ggc aag caa gag      2064
Leu Gly Val Lys Ala Arg Arg Gly Asp Val Phe Leu Gly Lys Gln Glu
        675                 680                 685 gtg acg atc ggc tcg aac gtc tcc aag atc tac gag gcc atc aag tcg      2112
Val Thr Ile Gly Ser Asn Val Ser Lys Ile Tyr Glu Ala Ile Lys Ser
    690                 695                 700 ggc agg atc aac aac gtc ctc ctc aag atg ctc gct tag                  2151
Gly Arg Ile Asn Asn Val Leu Leu Lys Met Leu Ala
705                 710                 715

<210> SEQ ID NO 10
<211> LENGTH: 716
<212> TYPE: PRT
<213> ORGANISM: mutant from Rhodotorula glutinis

<400> SEQUENCE: 10
```

-continued

```
Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25              30

Ala Gly Ser His Leu Pro Thr Thr Gln Val Thr Gln Val Asp Ile Val
            35                  40              45

Glu Lys Met Leu Ala Ala Pro Thr Asp Ser Thr Leu Glu Leu Asp Gly
50                      55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
            115                 120                 125

Ser Leu Gln Lys Ala Leu Leu Glu His Gln Leu Cys Gly Val Leu Pro
130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
            195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Glu Val Lys Val Lys
            340                 345                 350

Asp Asp Glu Gly Ile Leu Arg Gln Asp Arg Tyr Pro Leu Arg Thr Ser
            355                 360                 365

Pro Gln Trp Leu Gly Pro Leu Val Ser Asp Leu Ile His Ala His Ala
370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
```

```
                    420                 425                 430
Gly Lys Leu Asn Phe Thr Gln Leu Thr Glu Met Leu Asn Ala Gly Met
    435                 440                 445
Asn Arg Gly Leu Pro Ser Cys Leu Ala Ala Glu Asp Pro Ser Leu Ser
450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
                485                 490                 495
Met Ala Asn Gln Ala Val Asn Ser Leu Ala Leu Ile Ser Ala Arg Arg
            500                 505                 510
Thr Thr Glu Ser Asn Asp Val Leu Ser Leu Leu Ala Thr His Leu
        515                 520                 525
Tyr Cys Val Leu Gln Ala Ile Asp Leu Arg Ala Thr Glu Phe Glu Phe
    530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
                565                 570                 575
Val Asn Lys Thr Leu Ala Lys Arg Leu Glu Gln Thr Asn Ser Tyr Asp
            580                 585                 590
Leu Val Pro Arg Trp His Asp Ala Phe Ser Phe Ala Ala Gly Thr Val
        595                 600                 605
Val Glu Val Leu Ser Ser Thr Ser Leu Ser Leu Ala Ala Val Asn Ala
    610                 615                 620
Trp Lys Val Ala Ala Ala Glu Ser Ala Ile Ser Leu Thr Arg Gln Val
625                 630                 635                 640
Arg Glu Thr Phe Trp Ser Ala Ala Ser Thr Ser Ser Pro Ala Leu Ser
                645                 650                 655
Tyr Leu Ser Pro Arg Thr Gln Ile Leu Tyr Ala Phe Val Arg Glu Glu
            660                 665                 670
Leu Gly Val Lys Ala Arg Arg Gly Asp Val Phe Leu Gly Lys Gln Glu
        675                 680                 685
Val Thr Ile Gly Ser Asn Val Ser Lys Ile Tyr Glu Ala Ile Lys Ser
    690                 695                 700
Gly Arg Ile Asn Asn Val Leu Leu Lys Met Leu Ala
705                 710                 715

<210> SEQ ID NO 11
<211> LENGTH: 1620
<212> TYPE: DNA
<213> ORGANISM: Helianthus tuberosus
<220> FEATURE:
<221> NAME/KEY: CDS
<222> LOCATION: (31)..(1548)
<221> NAME/KEY: UNSURE
<222> LOCATION: (1588)..(1588)
<223> OTHER INFORMATION: n= A, T, C, or G
<221> NAME/KEY: UNSURE
<222> LOCATION: (1591)..(1591)
<223> OTHER INFORMATION: n= A, T, C, or G
<221> NAME/KEY: UNSURE
<222> LOCATION: (1593)..(1593)
<223> OTHER INFORMATION: n= A, T, C, or G
<221> NAME/KEY: UNSURE
<222> LOCATION: (1594)..(1594)
<223> OTHER INFORMATION: n= A, T, C, or G
<221> NAME/KEY: UNSURE
<222> LOCATION: (1597)..(1597)
<223> OTHER INFORMATION: n= A, T, C, or G
```

```
<221> NAME/KEY: UNSURE
<222> LOCATION: (1599)..(1599)
<223> OTHER INFORMATION: n= A, T, C, or G
<221> NAME/KEY: UNSURE
<222> LOCATION: (1600)..(1600)
<223> OTHER INFORMATION: n= A, T, C, or G
<221> NAME/KEY: UNSURE
<222> LOCATION: (1602)..(1602)
<223> OTHER INFORMATION: n= A, T, C, or G
<221> NAME/KEY: UNSURE
<222> LOCATION: (1604)..(1604)
<223> OTHER INFORMATION: n= A, T, C, or G
<221> NAME/KEY: UNSURE
<222> LOCATION: (1607)..(1607)
<223> OTHER INFORMATION: n= A, T, C, or G
<221> NAME/KEY: UNSURE
<222> LOCATION: (1608)..(1608)
<223> OTHER INFORMATION: n= A, T, C, or G

<400> SEQUENCE: 11
aaatcacaca acaccaccac caccgtaacc atg gac ctc ctc ctc ata gaa aaa       54
                                Met Asp Leu Leu Leu Ile Glu Lys
                                 1               5 acc ctc gtc gcc tta ttc gcc gcc att atc ggc gca ata cta atc tcc      102
Thr Leu Val Ala Leu Phe Ala Ala Ile Ile Gly Ala Ile Leu Ile Ser
     10                  15                  20 aaa ctc cgc ggt aaa aaa ttc aag ctc cca cct ggc cca atc ccg gtt      150
Lys Leu Arg Gly Lys Lys Phe Lys Leu Pro Pro Gly Pro Ile Pro Val
 25                  30                  35                  40 cca att ttc ggc aac tgg cta caa gtt ggc gat gat ttg aac cac cgg      198
Pro Ile Phe Gly Asn Trp Leu Gln Val Gly Asp Asp Leu Asn His Arg
                 45                  50                  55 aac tta acc gat ctg gct aag agg ttt ggt gag atc ttg ctg cta cgc      246
Asn Leu Thr Asp Leu Ala Lys Arg Phe Gly Glu Ile Leu Leu Leu Arg
         60                  65                  70 atg ggg cag agg aat ctg gta gtt gtg tct tcg cct gag ctt gct aaa      294
Met Gly Gln Arg Asn Leu Val Val Val Ser Ser Pro Glu Leu Ala Lys
     75                  80                  85 gag gtg ttg cat aca caa gga gtg gag ttt ggt tcg aga aca agg aat      342
Glu Val Leu His Thr Gln Gly Val Glu Phe Gly Ser Arg Thr Arg Asn
 90                  95                 100 gtt gtg ttc gat att ttt act ggg aag ggt cag gat atg gtg ttt acg      390
Val Val Phe Asp Ile Phe Thr Gly Lys Gly Gln Asp Met Val Phe Thr
105                 110                 115                 120 gtt tat ggt gag cat tgg agg aag atg agg agg atc atg acc gta ccc      438
Val Tyr Gly Glu His Trp Arg Lys Met Arg Arg Ile Met Thr Val Pro
                125                 130                 135 ttt ttc acc aac aaa gtt gtt cag caa tac agg tat ggg tgg gag gct      486
Phe Phe Thr Asn Lys Val Val Gln Gln Tyr Arg Tyr Gly Trp Glu Ala
        140                 145                 150 gag gcc gcg gcg gtt gtg gac gat gtg aag aag aat ccg gct gca gca      534
Glu Ala Ala Ala Val Val Asp Asp Val Lys Lys Asn Pro Ala Ala Ala
    155                 160                 165 act gaa gga atc gtg atc cga aga cgg tta caa ctc atg atg tat aac      582
Thr Glu Gly Ile Val Ile Arg Arg Arg Leu Gln Leu Met Met Tyr Asn
170                 175                 180 aac atg ttc aga atc atg ttc gac aga cga ttc gaa agt gaa gat gat      630
Asn Met Phe Arg Ile Met Phe Asp Arg Arg Phe Glu Ser Glu Asp Asp
185                 190                 195                 200 ccc ttg ttt ttg aaa ctc aag gcg ttg aac ggt gag agg agt cga ttg      678
Pro Leu Phe Leu Lys Leu Lys Ala Leu Asn Gly Glu Arg Ser Arg Leu
                205                 210                 215 gcg cag agc ttt gag tac aac tat ggc gat ttc atc cct att ttg cgg      726
Ala Gln Ser Phe Glu Tyr Asn Tyr Gly Asp Phe Ile Pro Ile Leu Arg
```

-continued

| | | |
|---|---|---|
| ccg ttt ttg aga aat tat ttg aag ttg tgc aag gaa gtt aaa gat aaa<br>Pro Phe Leu Arg Asn Tyr Leu Lys Leu Cys Lys Glu Val Lys Asp Lys<br>235                          240                    245 | 774 |
| agg att cag ctc ttc aag gat tac ttc gtt gac gaa agg aag aag att<br>Arg Ile Gln Leu Phe Lys Asp Tyr Phe Val Asp Glu Arg Lys Lys Ile<br>250                          255                    260 | 822 |
| gga agc act aag aaa atg gac aac aat cag ttg aaa tgt gcc att gat<br>Gly Ser Thr Lys Lys Met Asp Asn Asn Gln Leu Lys Cys Ala Ile Asp<br>265                    270                   275                  280 | 870 |
| cac att ctt gaa gct aaa gag aag ggt gag atc aat gaa gac aat gtt<br>His Ile Leu Glu Ala Lys Glu Lys Gly Glu Ile Asn Glu Asp Asn Val<br>                  285                    290                    295 | 918 |
| ctt tac att gtt gaa aac atc aat gtt gca gca atc gag aca act cta<br>Leu Tyr Ile Val Glu Asn Ile Asn Val Ala Ala Ile Glu Thr Thr Leu<br>                  300                    305                    310 | 966 |
| tgg tcg atc gaa tgg gga att gcg gag cta gtt aac cat ccc gag atc<br>Trp Ser Ile Glu Trp Gly Ile Ala Glu Leu Val Asn His Pro Glu Ile<br>315                          320                    325 | 1014 |
| caa gcc aaa ctc agg cac gag ctc gac acc aag ctc ggg ccc ggt gtc<br>Gln Ala Lys Leu Arg His Glu Leu Asp Thr Lys Leu Gly Pro Gly Val<br>330                          335                    340 | 1062 |
| cag atc acc gag ccc gac gtc caa aac ctc cct tac ctc caa gcc gtg<br>Gln Ile Thr Glu Pro Asp Val Gln Asn Leu Pro Tyr Leu Gln Ala Val<br>345                          350                    355                    360 | 1110 |
| gtc aag gaa acc ctc cgt ctc cgt atg gcg atc ccg ctt cta gtc cca<br>Val Lys Glu Thr Leu Arg Leu Arg Met Ala Ile Pro Leu Leu Val Pro<br>                  365                    370                    375 | 1158 |
| cac atg aac ctc cat gac gct aag ctc ggc ggg ttt gac atc ccg gcc<br>His Met Asn Leu His Asp Ala Lys Leu Gly Gly Phe Asp Ile Pro Ala<br>                  380                    385                    390 | 1206 |
| gaa agc aag atc ttg gtc aac gcg tgg tgg tta gca aac aac ccc gac<br>Glu Ser Lys Ile Leu Val Asn Ala Trp Trp Leu Ala Asn Asn Pro Asp<br>395                          400                    405 | 1254 |
| caa tgg aag aaa ccc gag gag ttt agg cca gag agg ttt ttg gaa gag<br>Gln Trp Lys Lys Pro Glu Glu Phe Arg Pro Glu Arg Phe Leu Glu Glu<br>          410                    415                    420 | 1302 |
| gaa gcg aag gtt gag gct aac ggg aat gat ttt agg tac ttg ccg ttt<br>Glu Ala Lys Val Glu Ala Asn Gly Asn Asp Phe Arg Tyr Leu Pro Phe<br>425                          430                    435                    440 | 1350 |
| gga gtc ggg aga agg agt tgc ccc ggg att att ctt gca ttg ccg ata<br>Gly Val Gly Arg Arg Ser Cys Pro Gly Ile Ile Leu Ala Leu Pro Ile<br>                  445                    450                    455 | 1398 |
| ctt ggt att aca atc ggg cgt ttg gtg cag aat ttc gag ctg ttg cct<br>Leu Gly Ile Thr Ile Gly Arg Leu Val Gln Asn Phe Glu Leu Leu Pro<br>                  460                    465                    470 | 1446 |
| cca ccg gga cag tct aag atc gat acc gat gag aag ggt ggg cag ttt<br>Pro Pro Gly Gln Ser Lys Ile Asp Thr Asp Glu Lys Gly Gly Gln Phe<br>475                          480                    485 | 1494 |
| agt ttg cat atc ttg aag cac tct act atc gta gct aaa cct agg tca<br>Ser Leu His Ile Leu Lys His Ser Thr Ile Val Ala Lys Pro Arg Ser<br>          490                    495                    500 | 1542 |
| ttt taa ggattcttgt ttatgttctt tattgtatga taaaccaagn gngnnggng<br>Phe<br>505 | 1598 |
| nngngngann aaaaaaaaaa aa | 1620 |

<210> SEQ ID NO 12
<211> LENGTH: 505

```
<212> TYPE: PRT
<213> ORGANISM: Helianthus tuberosus

<400> SEQUENCE: 12

Met Asp Leu Leu Leu Ile Glu Lys Thr Leu Val Ala Leu Phe Ala Ala
1               5                   10                  15

Ile Ile Gly Ala Ile Leu Ile Ser Lys Leu Arg Gly Lys Lys Phe Lys
                20                  25                  30

Leu Pro Pro Gly Pro Ile Pro Val Pro Ile Phe Gly Asn Trp Leu Gln
            35                  40                  45

Val Gly Asp Asp Leu Asn His Arg Asn Leu Thr Asp Leu Ala Lys Arg
    50                  55                  60

Phe Gly Glu Ile Leu Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
130                 135                 140

Gln Tyr Arg Tyr Gly Trp Glu Ala Glu Ala Ala Val Val Asp Asp
145                 150                 155                 160

Val Lys Lys Asn Pro Ala Ala Ala Thr Glu Gly Ile Val Ile Arg Arg
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Leu Lys Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Asn Tyr Leu Lys
225                 230                 235                 240

Leu Cys Lys Glu Val Lys Asp Lys Arg Ile Gln Leu Phe Lys Asp Tyr
                245                 250                 255

Phe Val Asp Glu Arg Lys Lys Ile Gly Ser Thr Lys Met Asp Asn
            260                 265                 270

Asn Gln Leu Lys Cys Ala Ile Asp His Ile Leu Glu Ala Lys Glu Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ala Lys Leu Arg His Glu Leu
                325                 330                 335

Asp Thr Lys Leu Gly Pro Gly Val Gln Ile Thr Glu Pro Asp Val Gln
            340                 345                 350

Asn Leu Pro Tyr Leu Gln Ala Val Val Lys Glu Thr Leu Arg Leu Arg
    355                 360                 365

Met Ala Ile Pro Leu Leu Val Pro His Met Asn Leu His Asp Ala Lys
370                 375                 380

Leu Gly Gly Phe Asp Ile Pro Ala Glu Ser Lys Ile Leu Val Asn Ala
385                 390                 395                 400
```

```
Trp Trp Leu Ala Asn Asn Pro Asp Gln Trp Lys Lys Pro Glu Glu Phe
            405                 410                 415

Arg Pro Glu Arg Phe Leu Glu Glu Ala Lys Val Glu Ala Asn Gly
        420                 425                 430

Asn Asp Phe Arg Tyr Leu Pro Phe Gly Val Gly Arg Ser Cys Pro
            435                 440                 445

Gly Ile Ile Leu Ala Leu Pro Ile Leu Gly Ile Thr Ile Gly Arg Leu
        450                 455                 460

Val Gln Asn Phe Glu Leu Leu Pro Pro Gly Gln Ser Lys Ile Asp
465                 470                 475                 480

Thr Asp Glu Lys Gly Gly Gln Phe Ser Leu His Ile Leu Lys His Ser
                485                 490                 495

Thr Ile Val Ala Lys Pro Arg Ser Phe
            500                 505

<210> SEQ ID NO 13
<211> LENGTH: 1863
<212> TYPE: DNA
<213> ORGANISM: Helianthus tuberosus
<220> FEATURE:
<221> NAME/KEY: CDS
<222> LOCATION: (1)..(1764)

<400> SEQUENCE: 13 ttg ttt gaa gaa gcg aaa gcg cga tat gaa aaa gct gtg ttt aaa gtg      48
Leu Phe Glu Glu Ala Lys Ala Arg Tyr Glu Lys Ala Val Phe Lys Val
1               5                   10                  15 gtt gat ttg gat gat tat gct gct gat gat gag gag tat gca gag aaa      96
Val Asp Leu Asp Asp Tyr Ala Ala Asp Asp Glu Glu Tyr Ala Glu Lys
            20                  25                  30 ttc aag aag gag aca ttt gct ttc ttc ttc ttg gct aca tat gga gat     144
Phe Lys Lys Glu Thr Phe Ala Phe Phe Phe Leu Ala Thr Tyr Gly Asp
        35                  40                  45 ggt gag cca act gat aat gct gca aga ttt tat aaa tgg ttc acc gag     192
Gly Glu Pro Thr Asp Asn Ala Ala Arg Phe Tyr Lys Trp Phe Thr Glu
    50                  55                  60 gga gat gat aaa gga gtt tgg ctt gaa aaa ctt cac tat ggt gtg ttt     240
Gly Asp Asp Lys Gly Val Trp Leu Glu Lys Leu His Tyr Gly Val Phe
65                  70                  75                  80 ggt ctt ggc aac aaa cag tat gag cat ttc aac aag att gca tta gtg     288
Gly Leu Gly Asn Lys Gln Tyr Glu His Phe Asn Lys Ile Ala Leu Val
                85                  90                  95 gtt gat gag ggt ctc aca gag cag ggt gca aag cgc ttt gtt cca gtt     336
Val Asp Glu Gly Leu Thr Glu Gln Gly Ala Lys Arg Phe Val Pro Val
            100                 105                 110 ggc ctt gga gat gac gat caa tca att gaa gat gat ttt tct gca tgg     384
Gly Leu Gly Asp Asp Asp Gln Ser Ile Glu Asp Asp Phe Ser Ala Trp
        115                 120                 125 aaa gaa tta gtg tgg cct gaa ttg gat caa ttg ctt ctt gat gaa gac     432
Lys Glu Leu Val Trp Pro Glu Leu Asp Gln Leu Leu Leu Asp Glu Asp
    130                 135                 140 gac aag act gct gcc act cct tac aca gct gcc att ccc gaa tac cga     480
Asp Lys Thr Ala Ala Thr Pro Tyr Thr Ala Ala Ile Pro Glu Tyr Arg
145                 150                 155                 160 gtc gtg ttt cat gac aaa cct gat acg ttt tcc gag aat cat agt caa     528
Val Val Phe His Asp Lys Pro Asp Thr Phe Ser Glu Asn His Ser Gln
                165                 170                 175 act aat ggt cat act gtt cac gat gct caa cat cca tgc aga tcc aac     576
Thr Asn Gly His Thr Val His Asp Ala Gln His Pro Cys Arg Ser Asn
```

```
                   180                 185                  190
gtg gct gtt aaa aaa gag ctc cat acc cct gaa tcc gat cgc tcc tgc    624
Val Ala Val Lys Lys Glu Leu His Thr Pro Glu Ser Asp Arg Ser Cys
            195                 200                  205 act cat ctt gaa ttt gac atc tct cac act gga cta tca tac gaa act    672
Thr His Leu Glu Phe Asp Ile Ser His Thr Gly Leu Ser Tyr Glu Thr
    210                 215                  220 ggg gat cac gtc ggt gtc tac tgt gaa aac cta att gaa gta gtg gag    720
Gly Asp His Val Gly Val Tyr Cys Glu Asn Leu Ile Glu Val Val Glu
225                 230                  235                  240 gaa gct gag aaa ctg ata gga tta cca gca gat act tat ttc tca tta    768
Glu Ala Glu Lys Leu Ile Gly Leu Pro Ala Asp Thr Tyr Phe Ser Leu
                245                 250                  255 cac att gat aac gaa gat gga aca cca ctc ggt gga cct aca ttg cag    816
His Ile Asp Asn Glu Asp Gly Thr Pro Leu Gly Gly Pro Thr Leu Gln
            260                 265                  270 cct cct ttc cct ccc tgc act tta aga aaa gca ttg acc aat tac gca    864
Pro Pro Phe Pro Pro Cys Thr Leu Arg Lys Ala Leu Thr Asn Tyr Ala
        275                 280                  285 gat ctg ttg agt tct ccc aaa aag tca acc ttg ctt gct cta gct gcg    912
Asp Leu Leu Ser Ser Pro Lys Lys Ser Thr Leu Leu Ala Leu Ala Ala
    290                 295                  300 cat gct tct gat gcc act gaa gct gat cga cta caa ttt ctt gca tct    960
His Ala Ser Asp Ala Thr Glu Ala Asp Arg Leu Gln Phe Leu Ala Ser
305                 310                  315                  320 cgt gag ggc aag gat gaa tat gct gaa tgg att gtt gca aac caa aga   1008
Arg Glu Gly Lys Asp Glu Tyr Ala Glu Trp Ile Val Ala Asn Gln Arg
                325                 330                  335 agc ctt ctt gag gtc atg gaa gct ttt ccg tca gct aaa cct ccg ctc   1056
Ser Leu Leu Glu Val Met Glu Ala Phe Pro Ser Ala Lys Pro Pro Leu
            340                 345                  350 ggg gtt ttc ttt gca gct att gcc ccg cgt ttg cag cct cga tac tac   1104
Gly Val Phe Phe Ala Ala Ile Ala Pro Arg Leu Gln Pro Arg Tyr Tyr
        355                 360                  365 tct att tct tcc tcc cca aag atg gta ccc aac agg att cat gtt acg   1152
Ser Ile Ser Ser Ser Pro Lys Met Val Pro Asn Arg Ile His Val Thr
    370                 375                  380 tgt gca tta gtt tat gag aag act cct gga ggt cgt atc cac aaa gga   1200
Cys Ala Leu Val Tyr Glu Lys Thr Pro Gly Gly Arg Ile His Lys Gly
385                 390                  395                  400 ata tgc tca acc tgg atg aag aat gct gtg cct ttg acc gaa aat caa   1248
Ile Cys Ser Thr Trp Met Lys Asn Ala Val Pro Leu Thr Glu Asn Gln
                405                 410                  415 gat tgc agc tcg gca ccc att ttt gtt aga aca tcg aac ttc aga ctt   1296
Asp Cys Ser Ser Ala Pro Ile Phe Val Arg Thr Ser Asn Phe Arg Leu
            420                 425                  430 cca gct gac cct aaa gtc ccg gtt atc atg att ggc cct gga acc ggg   1344
Pro Ala Asp Pro Lys Val Pro Val Ile Met Ile Gly Pro Gly Thr Gly
        435                 440                  445 ttg gct ccg ttt aga ggt ttt ctt caa gaa aga tta gct ctc aag gaa   1392
Leu Ala Pro Phe Arg Gly Phe Leu Gln Glu Arg Leu Ala Leu Lys Glu
    450                 455                  460 tct gga acc gaa ctc ggt caa tcc att ttg ttc ttc ggt tgc aga aac   1440
Ser Gly Thr Glu Leu Gly Gln Ser Ile Leu Phe Phe Gly Cys Arg Asn
465                 470                  475                  480 cgt aaa gtg gat ttc ata tat gag aat gaa ctg aac aac ttt gtt gaa   1488
Arg Lys Val Asp Phe Ile Tyr Glu Asn Glu Leu Asn Asn Phe Val Glu
                485                 490                  495 aat ggc gcg ctt tcc gag ctt gac atg gct ttc tct cgc gaa ggc gca   1536
```

-continued

```
                        Asn Gly Ala Leu Ser Glu Leu Asp Met Ala Phe Ser Arg Glu Gly Ala
                                        500                 505                 510 tct aaa gaa tac gtg caa cat aaa atg agc caa aag gct tcg gat ata         1584
Ser Lys Glu Tyr Val Gln His Lys Met Ser Gln Lys Ala Ser Asp Ile
            515                 520                 525 tgg aac atg ctt tct gag gga gca tac tta tac gtg tgt ggt gat gcc         1632
Trp Asn Met Leu Ser Glu Gly Ala Tyr Leu Tyr Val Cys Gly Asp Ala
        530                 535                 540 aaa ggc atg gct aaa gat gta cac cga acc ctt cac acc att gtg caa         1680
Lys Gly Met Ala Lys Asp Val His Arg Thr Leu His Thr Ile Val Gln
545                 550                 555                 560 gaa cag gga aat ttg gat tcc tct aaa gca gag ctg tat gtg aag aat         1728
Glu Gln Gly Asn Leu Asp Ser Ser Lys Ala Glu Leu Tyr Val Lys Asn
                565                 570                 575 cta caa atg tcg gga aga tac ctc cgt gat gtt tgg tgatctatcg              1774
Leu Gln Met Ser Gly Arg Tyr Leu Arg Asp Val Trp
            580                 585 agtaaacgg  aaataaatgt gagggaatt tataaacact agtttatgac agtataattt        1834 tgatcttta cagtcagtaa ttcgaattt                                          1863
```

<210> SEQ ID NO 14
<211> LENGTH: 588
<212> TYPE: PRT
<213> ORGANISM: Helianthus tuberosus

<400> SEQUENCE: 14

```
Leu Phe Glu Glu Ala Lys Ala Arg Tyr Glu Lys Ala Val Phe Lys Val
1               5                   10                  15

Val Asp Leu Asp Asp Tyr Ala Ala Asp Asp Glu Glu Tyr Ala Glu Lys
            20                  25                  30

Phe Lys Lys Glu Thr Phe Ala Phe Phe Leu Ala Thr Tyr Gly Asp
        35                  40                  45

Gly Glu Pro Thr Asp Asn Ala Ala Arg Phe Tyr Lys Trp Phe Thr Glu
    50                  55                  60

Gly Asp Asp Lys Gly Val Trp Leu Glu Lys Leu His Tyr Gly Val Phe
65                  70                  75                  80

Gly Leu Gly Asn Lys Gln Tyr Glu His Phe Asn Lys Ile Ala Leu Val
                85                  90                  95

Val Asp Glu Gly Leu Thr Glu Gln Gly Ala Lys Arg Phe Val Pro Val
            100                 105                 110

Gly Leu Gly Asp Asp Asp Gln Ser Ile Glu Asp Asp Phe Ser Ala Trp
        115                 120                 125

Lys Glu Leu Val Trp Pro Glu Leu Asp Gln Leu Leu Leu Asp Glu Asp
    130                 135                 140

Asp Lys Thr Ala Ala Thr Pro Tyr Thr Ala Ala Ile Pro Glu Tyr Arg
145                 150                 155                 160

Val Val Phe His Asp Lys Pro Asp Thr Phe Ser Glu Asn His Ser Gln
                165                 170                 175

Thr Asn Gly His Thr Val His Asp Ala Gln His Pro Cys Arg Ser Asn
            180                 185                 190

Val Ala Val Lys Lys Glu Leu His Thr Pro Glu Ser Asp Arg Ser Cys
        195                 200                 205

Thr His Leu Glu Phe Asp Ile Ser His Thr Gly Leu Ser Tyr Glu Thr
    210                 215                 220

Gly Asp His Val Gly Val Tyr Cys Glu Asn Leu Ile Glu Val Val Glu
225                 230                 235                 240
```

-continued

```
Glu Ala Glu Lys Leu Ile Gly Leu Pro Ala Asp Thr Tyr Phe Ser Leu
                245                 250                 255
His Ile Asp Asn Glu Asp Gly Thr Pro Leu Gly Gly Pro Thr Leu Gln
            260                 265                 270
Pro Pro Phe Pro Pro Cys Thr Leu Arg Lys Ala Leu Thr Asn Tyr Ala
        275                 280                 285
Asp Leu Leu Ser Ser Pro Lys Lys Ser Thr Leu Leu Ala Leu Ala Ala
    290                 295                 300
His Ala Ser Asp Ala Thr Glu Ala Asp Arg Leu Gln Phe Leu Ala Ser
305                 310                 315                 320
Arg Glu Gly Lys Asp Glu Tyr Ala Glu Trp Ile Val Ala Asn Gln Arg
                325                 330                 335
Ser Leu Leu Glu Val Met Glu Ala Phe Pro Ser Ala Lys Pro Pro Leu
            340                 345                 350
Gly Val Phe Phe Ala Ala Ile Ala Pro Arg Leu Gln Pro Arg Tyr Tyr
        355                 360                 365
Ser Ile Ser Ser Ser Pro Lys Met Val Pro Asn Arg Ile His Val Thr
    370                 375                 380
Cys Ala Leu Val Tyr Glu Lys Thr Pro Gly Gly Arg Ile His Lys Gly
385                 390                 395                 400
Ile Cys Ser Thr Trp Met Lys Asn Ala Val Pro Leu Thr Glu Asn Gln
                405                 410                 415
Asp Cys Ser Ser Ala Pro Ile Phe Val Arg Thr Ser Asn Phe Arg Leu
            420                 425                 430
Pro Ala Asp Pro Lys Val Pro Val Ile Met Ile Gly Pro Gly Thr Gly
        435                 440                 445
Leu Ala Pro Phe Arg Gly Phe Leu Gln Glu Arg Leu Ala Leu Lys Glu
    450                 455                 460
Ser Gly Thr Glu Leu Gly Gln Ser Ile Leu Phe Phe Gly Cys Arg Asn
465                 470                 475                 480
Arg Lys Val Asp Phe Ile Tyr Glu Asn Glu Leu Asn Asn Phe Val Glu
                485                 490                 495
Asn Gly Ala Leu Ser Glu Leu Asp Met Ala Phe Ser Arg Glu Gly Ala
            500                 505                 510
Ser Lys Glu Tyr Val Gln His Lys Met Ser Gln Lys Ala Ser Asp Ile
        515                 520                 525
Trp Asn Met Leu Ser Glu Gly Ala Tyr Leu Tyr Val Cys Gly Asp Ala
    530                 535                 540
Lys Gly Met Ala Lys Asp Val His Arg Thr Leu His Thr Ile Val Gln
545                 550                 555                 560
Glu Gln Gly Asn Leu Asp Ser Ser Lys Ala Glu Leu Tyr Val Lys Asn
                565                 570                 575
Leu Gln Met Ser Gly Arg Tyr Leu Arg Asp Val Trp
            580                 585

<210> SEQ ID NO 15
<211> LENGTH: 27
<212> TYPE: DNA
<213> ORGANISM: primer

<400> SEQUENCE: 15
ggcactgcta gcgactcgat ctcgcac                                     27

<210> SEQ ID NO 16
```

```
<211> LENGTH: 27
<212> TYPE: DNA
<213> ORGANISM: primer

<400> SEQUENCE: 16
ggcactgcta gctcgttcgc aaacggc                                    27

<210> SEQ ID NO 17
<211> LENGTH: 27
<212> TYPE: DNA
<213> ORGANISM: primer

<400> SEQUENCE: 17
ggcactgcta gcgtcgcatc cgcaaag                                    27

<210> SEQ ID NO 18
<211> LENGTH: 27
<212> TYPE: DNA
<213> ORGANISM: primer

<400> SEQUENCE: 18
ggcactgcta gccaggctgt caatggc                                    27

<210> SEQ ID NO 19
<211> LENGTH: 27
<212> TYPE: DNA
<213> ORGANISM: primer

<400> SEQUENCE: 19
ggcactgcta gcgcagtcgc aggctcg                                    27

<210> SEQ ID NO 20
<211> LENGTH: 27
<212> TYPE: DNA
<213> ORGANISM: primer

<400> SEQUENCE: 20
ggcactgcta gccaggtcac gcaggtc                                    27

<210> SEQ ID NO 21
<211> LENGTH: 30
<212> TYPE: DNA
<213> ORGANISM: primer

<400> SEQUENCE: 21
ggcactgcta gcatgctcgc cgcgccgacc                                 30

<210> SEQ ID NO 22
<211> LENGTH: 30
<212> TYPE: DNA
<213> ORGANISM: primer

<400> SEQUENCE: 22
ggcactgcta gccagaaggc tctcctcgag                                 30

<210> SEQ ID NO 23
<211> LENGTH: 33
<212> TYPE: DNA
<213> ORGANISM: primer

<400> SEQUENCE: 23
gcagaattcg gtaccctaag cgagcatctt gag                             33
```

<210> SEQ ID NO 24
<211> LENGTH: 20
<212> TYPE: DNA
<213> ORGANISM: primer

<400> SEQUENCE: 24
cgcgtgacgt cgtgaaggaa                                               20

<210> SEQ ID NO 25
<211> LENGTH: 54
<212> TYPE: DNA
<213> ORGANISM: primer

<400> SEQUENCE: 25
gaggaggtca aggtcaagga cgacgagggc attctccgcc aggaccgcta cccc         54

<210> SEQ ID NO 26
<211> LENGTH: 54
<212> TYPE: DNA
<213> ORGANISM: primer

<400> SEQUENCE: 26
ggggatgcgg tcctggcgga gaatgccctc gtcgtccttg accttgacct cctc         54

<210> SEQ ID NO 27
<211> LENGTH: 54
<212> TYPE: DNA
<213> ORGANISM: primer

<400> SEQUENCE: 27
acgacgcatg tccagccggc tgagatggcg aaccaggcgg tcaactcgct tgcg         54

<210> SEQ ID NO 28
<211> LENGTH: 54
<212> TYPE: DNA
<213> ORGANISM: primer

<400> SEQUENCE: 28
cgcaagcgag ttgaccgcct ggttcgccat ctcagccggc tggacatgcg tcgt         54

<210> SEQ ID NO 29
<211> LENGTH: 45
<212> TYPE: DNA
<213> ORGANISM: primer

<400> SEQUENCE: 29
gtctcgctca tcgaccagca ctttggctcc gccatgaccg gctcg                   45

<210> SEQ ID NO 30
<211> LENGTH: 45
<212> TYPE: DNA
<213> ORGANISM: primer

<400> SEQUENCE: 30
cgagccggtc atggcggagc caaagtgctg gtcgatgagc gagac                   45

<210> SEQ ID NO 31
<211> LENGTH: 2061
<212> TYPE: DNA
<213> ORGANISM: mutant from Rhodotorula glutinis
<220> FEATURE:
<221> NAME/KEY: CDS]
<222> LOCATION: (1)..(2061)

<400> SEQUENCE: 31

-continued

| | |
|---|---|
| gca gtc gca ggc tcg cac ctg ccc aca acc cag gtc acg cag gtc gac<br>Ala Val Ala Gly Ser His Leu Pro Thr Thr Gln Val Thr Gln Val Asp<br>1                   5                     10                  15 | 48 |
| atc gtc gag aag atg ctc gcc gcg ccg acc gac tcg acg ctc gaa ctc<br>Ile Val Glu Lys Met Leu Ala Ala Pro Thr Asp Ser Thr Leu Glu Leu<br>            20                    25                    30 | 96 |
| gac ggc tac tcg ctc aac ctc gga gac gtc gtc tcg gcc gcg agg aag<br>Asp Gly Tyr Ser Leu Asn Leu Gly Asp Val Val Ser Ala Ala Arg Lys<br>               35                    40                   45 | 144 |
| ggc agg cct gtc cgc gtc aag gac agc gac gag atc cgc tca aag att<br>Gly Arg Pro Val Arg Val Lys Asp Ser Asp Glu Ile Arg Ser Lys Ile<br>    50                    55                    60 | 192 |
| gac aaa tcg gtc gag ttc ttg cgc tcg caa ctc tcc atg agc gtc tac<br>Asp Lys Ser Val Glu Phe Leu Arg Ser Gln Leu Ser Met Ser Val Tyr<br>65                    70                    75                  80 | 240 |
| ggc gtc acg act gga ttt ggc gga tcc gca gac acc cgc acc gag gac<br>Gly Val Thr Thr Gly Phe Gly Gly Ser Ala Asp Thr Arg Thr Glu Asp<br>               85                    90                   95 | 288 |
| gcc atc tcg ctc cag aag gct ctc ctc gag cac cag ctc tgc ggt gtt<br>Ala Ile Ser Leu Gln Lys Ala Leu Leu Glu His Gln Leu Cys Gly Val<br>           100                   105                110 | 336 |
| ctc cct tcg tcg ttc gac tcg ttc cgc ctc ggc cgc ggt ctc gag aac<br>Leu Pro Ser Ser Phe Asp Ser Phe Arg Leu Gly Arg Gly Leu Glu Asn<br>        115                   120                 125 | 384 |
| tcg ctt ccc ctc gag gtt gtt cgc ggc gcc atg aca atc cgc gtc aac<br>Ser Leu Pro Leu Glu Val Val Arg Gly Ala Met Thr Ile Arg Val Asn<br>    130                   135                140 | 432 |
| agc ttg acc cgc ggc cac tcg gct gtc cgc ctc gtc gtc ctc gag gcg<br>Ser Leu Thr Arg Gly His Ser Ala Val Arg Leu Val Val Leu Glu Ala<br>145                 150                   155                160 | 480 |
| ctc acc aac ttc ctc aac cac ggc atc acc ccc atc gtc ccc ctc cgc<br>Leu Thr Asn Phe Leu Asn His Gly Ile Thr Pro Ile Val Pro Leu Arg<br>                165                 170                175 | 528 |
| ggc acc atc tct gcg tcg ggc gac ctg tct cct ctc tcc tac att gca<br>Gly Thr Ile Ser Ala Ser Gly Asp Leu Ser Pro Leu Ser Tyr Ile Ala<br>        180                   185                 190 | 576 |
| gcg gcc atc agc ggt cac ccg gac agc aag gtg cac gtc gtc cac gag<br>Ala Ala Ile Ser Gly His Pro Asp Ser Lys Val His Val Val His Glu<br>    195                   200                 205 | 624 |
| ggc aag gag aag atc ctg tac gcc cgc gag gcg atg gcg ctc ttc aac<br>Gly Lys Glu Lys Ile Leu Tyr Ala Arg Glu Ala Met Ala Leu Phe Asn<br>210                 215                   220 | 672 |
| ctc gag ccc gtc gtc ctc ggc ccg aag gaa ggt ctc ggt ctc gtc aac<br>Leu Glu Pro Val Val Leu Gly Pro Lys Glu Gly Leu Gly Leu Val Asn<br>225                 230                   235                240 | 720 |
| ggc acc gcc gtc tca gca tcg atg gcc acc ctc gct ctg cac gac gct<br>Gly Thr Ala Val Ser Ala Ser Met Ala Thr Leu Ala Leu His Asp Ala<br>                     245                 250                255 | 768 |
| cac atg ctc tcg ctc ctc tcg cag tcg ctc acg gcc atg acg gtc gaa<br>His Met Leu Ser Leu Leu Ser Gln Ser Leu Thr Ala Met Thr Val Glu<br>    260                   265                270 | 816 |
| gcg atg gtc ggc cac gcc ggc tcg ttc cac ccc ttc ctt cac gac gtc<br>Ala Met Val Gly His Ala Gly Ser Phe His Pro Phe Leu His Asp Val<br>        275                   280                 285 | 864 |
| acg cgc cct cac ccg acg cag atc gaa gtc gcg gga aac atc cgc aag<br>Thr Arg Pro His Pro Thr Gln Ile Glu Val Ala Gly Asn Ile Arg Lys<br>    290                   295                300 | 912 |
| ctc ctc gag gga agc cgc ttt gct gtc cac cat gag gag gag gtc aag<br>Leu Leu Glu Gly Ser Arg Phe Ala Val His His Glu Glu Glu Val Lys | 960 |

```
     305                 310                 315                 320 gtc aag gac gac gag ggc att ctc cgc cag gac cgc tac ccc ttg cgc    1008
Val Lys Asp Asp Glu Gly Ile Leu Arg Gln Asp Arg Tyr Pro Leu Arg
                325                 330                 335 acg tct cct cag tgg ctc ggc ccg ctc gtc agc gac ctc att cac gcc    1056
Thr Ser Pro Gln Trp Leu Gly Pro Leu Val Ser Asp Leu Ile His Ala
                340                 345                 350 cac gcc gtc ctc acc atc gag gcc ggc cag tcg acg acc gac aac cct    1104
His Ala Val Leu Thr Ile Glu Ala Gly Gln Ser Thr Thr Asp Asn Pro
                355                 360                 365 ctc atc gac gtc gag aac aag act tcg cac cac ggc ggc aat ttc cag    1152
Leu Ile Asp Val Glu Asn Lys Thr Ser His His Gly Gly Asn Phe Gln
                370                 375                 380 gct gcc gct gtg gcc aac acc atg gag aag act cgc ctc ggg ctc gcc    1200
Ala Ala Ala Val Ala Asn Thr Met Glu Lys Thr Arg Leu Gly Leu Ala
385                 390                 395                 400 cag atc ggc aag ctc aac ttc acg cag ctc acc gag atg ctc aac gcc    1248
Gln Ile Gly Lys Leu Asn Phe Thr Gln Leu Thr Glu Met Leu Asn Ala
                405                 410                 415 ggc atg aac cgc ggc ctc ccc tcc tgc ctc gcg gcc gaa gac ccc tcg    1296
Gly Met Asn Arg Gly Leu Pro Ser Cys Leu Ala Ala Glu Asp Pro Ser
                420                 425                 430 ctc tcc tac cac tgc aag ggc ctc gac atc gcc gct gcg gcg tac acc    1344
Leu Ser Tyr His Cys Lys Gly Leu Asp Ile Ala Ala Ala Ala Tyr Thr
                435                 440                 445 tcg gag ttg gga cac ctc gcc aac cct gtg acg acg cat gtc cag ccg    1392
Ser Glu Leu Gly His Leu Ala Asn Pro Val Thr Thr His Val Gln Pro
                450                 455                 460 gct gag atg gcg aac cag gcg gtc aac tcg ctt gcg ctc atc tcg gct    1440
Ala Glu Met Ala Asn Gln Ala Val Asn Ser Leu Ala Leu Ile Ser Ala
465                 470                 475                 480 cgt cgc acg acc gag tcc aac gac gtc ctt tct ctc ctc ctc gcc acc    1488
Arg Arg Thr Thr Glu Ser Asn Asp Val Leu Ser Leu Leu Leu Ala Thr
                485                 490                 495 cac ctc tac tgc gtt ctc caa gcc atc gac ttg cgc gcg atc gag ttc    1536
His Leu Tyr Cys Val Leu Gln Ala Ile Asp Leu Arg Ala Ile Glu Phe
                500                 505                 510 gag ttc aag aag cag ttc ggc cca gcc atc gtc tcg ctc atc gac cag    1584
Glu Phe Lys Lys Gln Phe Gly Pro Ala Ile Val Ser Leu Ile Asp Gln
                515                 520                 525 cac ttt ggc tcc gcc atg acc ggc tcg aac ctg cgc gac gag ctc gtc    1632
His Phe Gly Ser Ala Met Thr Gly Ser Asn Leu Arg Asp Glu Leu Val
                530                 535                 540 gag aag gtg aac aag acg ctc gcc aag cgc ctc gag cag acc aac tcg    1680
Glu Lys Val Asn Lys Thr Leu Ala Lys Arg Leu Glu Gln Thr Asn Ser
545                 550                 555                 560 tac gac ctc gtc ccg cgc tgg cac gac gcc ttc tcc ttc gcc gcc ggc    1728
Tyr Asp Leu Val Pro Arg Trp His Asp Ala Phe Ser Phe Ala Ala Gly
                565                 570                 575 acc gtc gtc gag gtc ctc tcg tcg acg tcg ctc tcg ctc gcc gcc gtc    1776
Thr Val Val Glu Val Leu Ser Ser Thr Ser Leu Ser Leu Ala Ala Val
                580                 585                 590 aac gcc tgg aag gtc gcc gcc gcc gag tcg gcc atc tcg ctc acc cgc    1824
Asn Ala Trp Lys Val Ala Ala Ala Glu Ser Ala Ile Ser Leu Thr Arg
                595                 600                 605 caa gtc cgc gag acc ttc tgg tcc gcc gcg tcg acc tcg tcg ccc gcg    1872
Gln Val Arg Glu Thr Phe Trp Ser Ala Ala Ser Thr Ser Ser Pro Ala
                610                 615                 620 ctc tcg tac ctc tcg ccg cgc act cag atc ctc tac gcc ttc gtc cgc    1920
```

```
Leu Ser Tyr Leu Ser Pro Arg Thr Gln Ile Leu Tyr Ala Phe Val Arg
625                 630                 635                 640 gag gag ctt ggc gtc aag gcc cgc cgc gga gac gtc ttc ctc ggc aag     1968
Glu Glu Leu Gly Val Lys Ala Arg Arg Gly Asp Val Phe Leu Gly Lys
                645                 650                 655 caa gag gtg acg atc ggc tcg aac gtc tcc aag atc tac gag gcc atc     2016
Gln Glu Val Thr Ile Gly Ser Asn Val Ser Lys Ile Tyr Glu Ala Ile
            660                 665                 670 aag tcg ggc agg atc aac aac gtc ctc ctc aag atg ctc gct tag         2061
Lys Ser Gly Arg Ile Asn Asn Val Leu Leu Lys Met Leu Ala
            675                 680                 685

<210> SEQ ID NO 32
<211> LENGTH: 686
<212> TYPE: PRT
<213> ORGANISM: mutant from Rhodotorula glutinis

<400> SEQUENCE: 32

Ala Val Ala Gly Ser His Leu Pro Thr Thr Gln Val Thr Gln Val Asp
1               5                   10                  15

Ile Val Glu Lys Met Leu Ala Ala Pro Thr Asp Ser Thr Leu Glu Leu
                20                  25                  30

Asp Gly Tyr Ser Leu Asn Leu Gly Asp Val Val Ser Ala Ala Arg Lys
            35                  40                  45

Gly Arg Pro Val Arg Val Lys Asp Ser Asp Glu Ile Arg Ser Lys Ile
        50                  55                  60

Asp Lys Ser Val Glu Phe Leu Arg Ser Gln Leu Ser Met Ser Val Tyr
65                  70                  75                  80

Gly Val Thr Thr Gly Phe Gly Gly Ser Ala Asp Thr Arg Thr Glu Asp
                85                  90                  95

Ala Ile Ser Leu Gln Lys Ala Leu Leu Glu His Gln Leu Cys Gly Val
            100                 105                 110

Leu Pro Ser Ser Phe Asp Ser Phe Arg Leu Gly Arg Gly Leu Glu Asn
        115                 120                 125

Ser Leu Pro Leu Glu Val Val Arg Gly Ala Met Thr Ile Arg Val Asn
    130                 135                 140

Ser Leu Thr Arg Gly His Ser Ala Val Arg Leu Val Val Leu Glu Ala
145                 150                 155                 160

Leu Thr Asn Phe Leu Asn His Gly Ile Thr Pro Ile Val Pro Leu Arg
                165                 170                 175

Gly Thr Ile Ser Ala Ser Gly Asp Leu Ser Pro Leu Ser Tyr Ile Ala
            180                 185                 190

Ala Ala Ile Ser Gly His Pro Asp Ser Lys Val His Val Val His Glu
        195                 200                 205

Gly Lys Glu Lys Ile Leu Tyr Ala Arg Glu Ala Met Ala Leu Phe Asn
    210                 215                 220

Leu Glu Pro Val Val Leu Gly Pro Lys Glu Gly Leu Gly Leu Val Asn
225                 230                 235                 240

Gly Thr Ala Val Ser Ala Ser Met Ala Thr Leu Ala Leu His Asp Ala
                245                 250                 255

His Met Leu Ser Leu Leu Ser Gln Ser Leu Thr Ala Met Thr Val Glu
            260                 265                 270

Ala Met Val Gly His Ala Gly Ser Phe His Pro Phe Leu His Asp Val
        275                 280                 285

Thr Arg Pro His Pro Thr Gln Ile Glu Val Ala Gly Asn Ile Arg Lys
    290                 295                 300
```

```
Leu Leu Glu Gly Ser Arg Phe Ala Val His His Glu Glu Val Lys
305                 310                 315                 320

Val Lys Asp Asp Glu Gly Ile Leu Arg Gln Asp Arg Tyr Pro Leu Arg
            325                 330                 335

Thr Ser Pro Gln Trp Leu Gly Pro Leu Val Ser Asp Leu Ile His Ala
            340                 345                 350

His Ala Val Leu Thr Ile Glu Ala Gly Gln Ser Thr Thr Asp Asn Pro
            355                 360                 365

Leu Ile Asp Val Glu Asn Lys Thr Ser His His Gly Gly Asn Phe Gln
370                 375                 380

Ala Ala Ala Val Ala Asn Thr Met Glu Lys Thr Arg Leu Gly Leu Ala
385                 390                 395                 400

Gln Ile Gly Lys Leu Asn Phe Thr Gln Leu Thr Glu Met Leu Asn Ala
                405                 410                 415

Gly Met Asn Arg Gly Leu Pro Ser Cys Leu Ala Ala Glu Asp Pro Ser
            420                 425                 430

Leu Ser Tyr His Cys Lys Gly Leu Asp Ile Ala Ala Ala Ala Tyr Thr
            435                 440                 445

Ser Glu Leu Gly His Leu Ala Asn Pro Val Thr Thr His Val Gln Pro
450                 455                 460

Ala Glu Met Ala Asn Gln Ala Val Asn Ser Leu Ala Leu Ile Ser Ala
465                 470                 475                 480

Arg Arg Thr Thr Glu Ser Asn Asp Val Leu Ser Leu Leu Leu Ala Thr
                485                 490                 495

His Leu Tyr Cys Val Leu Gln Ala Ile Asp Leu Arg Ala Ile Glu Phe
            500                 505                 510

Glu Phe Lys Lys Gln Phe Gly Pro Ala Ile Val Ser Leu Ile Asp Gln
            515                 520                 525

His Phe Gly Ser Ala Met Thr Gly Ser Asn Leu Arg Asp Glu Leu Val
            530                 535                 540

Glu Lys Val Asn Lys Thr Leu Ala Lys Arg Leu Glu Gln Thr Asn Ser
545                 550                 555                 560

Tyr Asp Leu Val Pro Arg Trp His Asp Ala Phe Ser Phe Ala Ala Gly
                565                 570                 575

Thr Val Val Glu Val Leu Ser Ser Thr Ser Leu Ser Leu Ala Ala Val
            580                 585                 590

Asn Ala Trp Lys Val Ala Ala Ala Glu Ser Ala Ile Ser Leu Thr Arg
            595                 600                 605

Gln Val Arg Glu Thr Phe Trp Ser Ala Ala Ser Thr Ser Ser Pro Ala
            610                 615                 620

Leu Ser Tyr Leu Ser Pro Arg Thr Gln Ile Leu Tyr Ala Phe Val Arg
625                 630                 635                 640

Glu Glu Leu Gly Val Lys Ala Arg Arg Gly Asp Val Phe Leu Gly Lys
                645                 650                 655

Gln Glu Val Thr Ile Gly Ser Val Ser Lys Ile Tyr Glu Ala Ile
            660                 665                 670

Lys Ser Gly Arg Ile Asn Asn Val Leu Leu Lys Met Leu Ala
            675                 680                 685

<210> SEQ ID NO 33
<211> LENGTH: 716
<212> TYPE: PRT
<213> ORGANISM: mutant from Rhodotorula glutinis
<220> FEATURE:
```

```
<221> NAME/KEY: UNSURE
<222> LOCATION: (126)..(126)
<223> OTHER INFORMATION: X= Gly, Ser, Ala, Thr
<221> NAME/KEY: UNSURE
<222> LOCATION: (138)..(138)
<223> OTHER INFORMATION: X= Leu, Met, Ile, Val, Cys
<221> NAME/KEY: UNSURE
<222> LOCATION: (149)..(149)
<223> OTHER INFORMATION: X= Pro, Ala, Ser, Thr, Gly
<221> NAME/KEY: UNSURE
<222> LOCATION: (181)..(181)
<223> OTHER INFORMATION: X= Pro, Ala, Ser, Thr, Gly
<221> NAME/KEY: UNSURE
<222> LOCATION: (198)..(198)
<223> OTHER INFORMATION: X= Asp, Asn, Glu, Gln
<221> NAME/KEY: UNSURE
<222> LOCATION: (202)..(202)
<223> OTHER INFORMATION: X= Val, Met, Leu, Cys
<221> NAME/KEY: UNSURE
<222> LOCATION: (235)..(235)
<223> OTHER INFORMATION: X= Ala, Gly, Ser, Thr, Pro
<221> NAME/KEY: UNSURE
<222> LOCATION: (502)..(502)
<223> OTHER INFORMATION: X= Gly, Ala, Ser, Thr, Pro
<221> NAME/KEY: UNSURE
<222> LOCATION: (540)..(540)
<223> OTHER INFORMATION: X=Thr, Ala, Ser, Pro, Gly

<400> SEQUENCE: 33

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Xaa Ala Ile
        115                 120                 125

Ser Leu Gln Lys Ala Leu Leu Glu His Xaa Leu Cys Gly Val Leu Pro
130                 135                 140

Ser Ser Phe Asp Xaa Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Xaa Ala Val Arg Leu Val Val Leu Glu Ala Leu Thr
            180                 185                 190

Asn Phe Leu Asn His Xaa Ile Thr Pro Xaa Val Pro Leu Arg Gly Thr
        195                 200                 205

Ile Ser Ala Ser Gly Asp Leu Ser Pro Leu Ser Tyr Ile Ala Ala
    210                 215                 220

Ile Ser Gly His Pro Asp Ser Lys Val His Xaa Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
```

```
                    260                 265                 270
    Ala Val Ser Ala Ser Met Ala Thr Leu Ala Leu His Asp Ala His Met
                275                 280                 285

Leu Ser Leu Ser Gln Ser Leu Thr Ala Met Thr Val Glu Ala Met
        290                 295                 300

Val Gly His Ala Gly Ser Phe His Pro Phe Leu His Asp Val Thr Arg
    305                 310                 315                 320

Pro His Pro Thr Gln Ile Glu Val Ala Gly Asn Ile Arg Lys Leu Leu
                    325                 330                 335

Glu Gly Ser Arg Phe Ala Val His His Glu Glu Val Lys Val Lys
                340                 345                 350

Asp Asp Glu Gly Ile Leu Arg Gln Asp Arg Tyr Pro Leu Arg Thr Ser
                    355                 360                 365

Pro Gln Trp Leu Gly Pro Leu Val Ser Asp Leu Ile His Ala His Ala
        370                 375                 380

Val Leu Thr Ile Glu Ala Gly Gln Ser Thr Thr Asp Asn Pro Leu Ile
    385                 390                 395                 400

Asp Val Glu Asn Lys Thr Ser His His Gly Gly Asn Phe Gln Ala Ala
                    405                 410                 415

Ala Val Ala Asn Thr Met Glu Lys Thr Arg Leu Gly Leu Ala Gln Ile
                420                 425                 430

Gly Lys Leu Asn Phe Thr Gln Leu Thr Glu Met Leu Asn Ala Gly Met
                435                 440                 445

Asn Arg Gly Leu Pro Ser Cys Leu Ala Ala Glu Asp Pro Ser Leu Ser
        450                 455                 460

Tyr His Cys Lys Gly Leu Asp Ile Ala Ala Ala Tyr Thr Ser Glu
    465                 470                 475                 480

Leu Gly His Leu Ala Asn Pro Val Thr Thr His Val Gln Pro Ala Glu
                    485                 490                 495

Met Ala Asn Gln Ala Xaa Asn Ser Leu Ala Leu Ile Ser Ala Arg Arg
                500                 505                 510

Thr Thr Glu Ser Asn Asp Val Leu Ser Leu Leu Leu Ala Thr His Leu
                515                 520                 525

Tyr Cys Val Leu Gln Ala Ile Asp Leu Arg Ala Ile Glu Phe Glu Phe
        530                 535                 540

Lys Lys Gln Phe Gly Pro Ala Ile Val Ser Leu Ile Asp Gln His Phe
    545                 550                 555                 560

Gly Ser Ala Met Thr Gly Ser Asn Leu Arg Asp Glu Leu Val Glu Lys
                    565                 570                 575

Val Asn Lys Thr Leu Ala Lys Arg Leu Glu Gln Thr Asn Ser Tyr Asp
                580                 585                 590

Leu Val Pro Arg Trp His Asp Ala Phe Ser Phe Ala Ala Gly Thr Val
            595                 600                 605

Val Glu Val Leu Ser Ser Thr Ser Leu Ser Leu Ala Ala Val Asn Ala
    610                 615                 620

Trp Lys Val Ala Ala Ala Glu Ser Ala Ile Ser Leu Thr Arg Gln Val
    625                 630                 635                 640

Arg Glu Thr Phe Trp Ser Ala Ala Ser Thr Ser Ser Pro Ala Leu Ser
                    645                 650                 655

Tyr Leu Ser Pro Arg Thr Gln Ile Leu Tyr Ala Phe Val Arg Glu Glu
                660                 665                 670

Leu Gly Val Lys Ala Arg Arg Gly Asp Val Phe Leu Gly Lys Gln Glu
                675                 680                 685
```

```
Val Thr Ile Gly Ser Asn Val Ser Lys Ile Tyr Glu Ala Ile Lys Ser
        690                 695                 700

Gly Arg Ile Asn Asn Val Leu Leu Lys Met Leu Ala
705                 710                 715

<210> SEQ ID NO 34
<211> LENGTH: 716
<212> TYPE: PRT
<213> ORGANISM: mutant from Rhodotorula glutinis
<220> FEATURE:
<221> NAME/KEY: UNSURE
<222> LOCATION: (126)..(126)
<223> OTHER INFORMATION: X= Gly, Ala, Ser, Thr
<221> NAME/KEY: UNSURE
<222> LOCATION: (138)..(138)
<223> OTHER INFORMATION: X= Leu, Met, Ile, Val, Cys
<221> NAME/KEY: UNSURE
<222> LOCATION: (540)..(540)
<223> OTHER INFORMATION: X= Thr, Ala, Ser, Pro, Gly

<400> SEQUENCE: 34

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Xaa Ala Ile
        115                 120                 125

Ser Leu Gln Lys Ala Leu Leu Glu His Xaa Leu Cys Gly Val Leu Pro
130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285
```

-continued

```
Leu Ser Leu Leu Ser Gln Ser Leu Thr Ala Met Thr Val Glu Ala Met
    290                 295                 300
Val Gly His Ala Gly Ser Phe His Pro Phe Leu His Asp Val Thr Arg
305                 310                 315                 320
Pro His Pro Thr Gln Ile Glu Val Ala Gly Asn Ile Arg Lys Leu Leu
                325                 330                 335
Glu Gly Ser Arg Phe Ala Val His Glu Glu Val Lys Val Lys
            340                 345                 350
Asp Asp Glu Gly Ile Leu Arg Gln Asp Arg Tyr Pro Leu Arg Thr Ser
            355                 360                 365
Pro Gln Trp Leu Gly Pro Leu Val Ser Asp Leu Ile His Ala His Ala
    370                 375                 380
Val Leu Thr Ile Glu Ala Gly Gln Ser Thr Thr Asp Asn Pro Leu Ile
385                 390                 395                 400
Asp Val Glu Asn Lys Thr Ser His His Gly Gly Asn Phe Gln Ala Ala
                405                 410                 415
Ala Val Ala Asn Thr Met Glu Lys Thr Arg Leu Gly Leu Ala Gln Ile
            420                 425                 430
Gly Lys Leu Asn Phe Thr Gln Leu Thr Glu Met Leu Asn Ala Gly Met
        435                 440                 445
Asn Arg Gly Leu Pro Ser Cys Leu Ala Ala Glu Asp Pro Ser Leu Ser
    450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
                485                 490                 495
Met Ala Asn Gln Ala Val Asn Ser Leu Ala Leu Ile Ser Ala Arg Arg
            500                 505                 510
Thr Thr Glu Ser Asn Asp Val Leu Ser Leu Leu Ala Thr His Leu
        515                 520                 525
Tyr Cys Val Leu Gln Ala Ile Asp Leu Arg Ala Xaa Glu Phe Glu Phe
    530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
                565                 570                 575
Val Asn Lys Thr Leu Ala Lys Arg Leu Glu Gln Thr Asn Ser Tyr Asp
            580                 585                 590
Leu Val Pro Arg Trp His Asp Ala Phe Ser Phe Ala Ala Gly Thr Val
        595                 600                 605
Val Glu Val Leu Ser Ser Thr Ser Leu Ser Leu Ala Ala Val Asn Ala
    610                 615                 620
Trp Lys Val Ala Ala Glu Ser Ala Ile Ser Leu Thr Arg Gln Val
625                 630                 635                 640
Arg Glu Thr Phe Trp Ser Ala Ala Ser Thr Ser Ser Pro Ala Leu Ser
                645                 650                 655
Tyr Leu Ser Pro Arg Thr Gln Ile Leu Tyr Ala Phe Val Arg Glu Glu
            660                 665                 670
Leu Gly Val Lys Ala Arg Arg Gly Asp Val Phe Leu Gly Lys Gln Glu
        675                 680                 685
Val Thr Ile Gly Ser Asn Val Ser Lys Ile Tyr Glu Ala Ile Lys Ser
    690                 695                 700
Gly Arg Ile Asn Asn Val Leu Leu Lys Met Leu Ala
```

```
                705                 710                 715
```

<210> SEQ ID NO 35
<211> LENGTH: 716
<212> TYPE: PRT
<213> ORGANISM: mutant from Rhodotorula glutinis
<220> FEATURE:
<221> NAME/KEY: UNSURE
<222> LOCATION: (198)..(198)
<223> OTHER INFORMATION: X= Asp, Asn, Glu, Gln
<221> NAME/KEY: UNSURE
<222> LOCATION: (540)..(540)
<223> OTHER INFORMATION: X= Thr, Ala, Ser, Pro, Gly

<400> SEQUENCE: 35

```
Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Ser Ala Val Arg Leu Val Val Leu Glu Ala Leu Thr
            180                 185                 190

Asn Phe Leu Asn His Xaa Ile Thr Pro Ile Val Pro Leu Arg Gly Thr
        195                 200                 205

Ile Ser Ala Ser Gly Asp Leu Ser Pro Leu Ser Tyr Ile Ala Ala Ala
    210                 215                 220

Ile Ser Gly His Pro Asp Ser Lys Val His Val Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
        275                 280                 285

Leu Ser Leu Leu Ser Gln Ser Leu Thr Ala Met Thr Val Glu Ala Met
    290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335
```

```
Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser
            355                 360                 365

Pro Gln Trp Leu Gly Pro Leu Val Ser Asp Leu Ile His Ala His Ala
            370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
            405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
            435                 440                 445

Asn Arg Gly Leu Pro Ser Cys Leu Ala Ala Glu Asp Pro Ser Leu Ser
            450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
            485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
            515                 520                 525

Tyr Cys Val Leu Gln Ala Ile Asp Leu Arg Ala Xaa Glu Phe Glu Phe
530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
            565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
            595                 600                 605

Val Glu Val Leu Ser Ser Thr Ser Leu Ser Leu Ala Ala Val Asn Ala
            610                 615                 620

Trp Lys Val Ala Ala Glu Ser Ala Ile Ser Leu Thr Arg Gln Val
625                 630                 635                 640

Arg Glu Thr Phe Trp Ser Ala Ser Thr Ser Ser Pro Ala Leu Ser
            645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
            675                 680                 685

Val Thr Ile Gly Ser Asn Val Ser Lys Ile Tyr Glu Ala Ile Lys Ser
            690                 695                 700

Gly Arg Ile Asn Asn Val Leu Leu Lys Met Leu Ala
705                 710                 715

<210> SEQ ID NO 36
<211> LENGTH: 716
<212> TYPE: PRT
<213> ORGANISM: mutant from Rhodotorula glutinis
<220> FEATURE:
```

-continued

```
<221> NAME/KEY: UNSURE
<222> LOCATION: (181)..(181)
<223> OTHER INFORMATION: X= Pro, Ala, Ser, Thr, Gly
<221> NAME/KEY: UNSURE
<222> LOCATION: (235)..(235)
<223> OTHER INFORMATION: X= Ala, Gly, Ser, Thr, Pro
<221> NAME/KEY: UNSURE
<222> LOCATION: (540)..(540)
<223> OTHER INFORMATION: X= Thr, Ala, Ser, Pro, Gly

<400> SEQUENCE: 36
```

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
            35                  40                  45

Glu Lys Met Leu Ala Ala Pro Thr Asp Ser Thr Leu Glu Leu Asp Gly
50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
                100                 105                 110

Thr Thr Gly Phe Gly Gly Ser Ala Asp Thr Arg Thr Glu Asp Ala Ile
            115                 120                 125

Ser Leu Gln Lys Ala Leu Leu Glu His Gln Leu Cys Gly Val Leu Pro
130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
                165                 170                 175

Thr Arg Gly His Xaa Ala Val Arg Leu Val Val Leu Glu Ala Leu Thr
            180                 185                 190

Asn Phe Leu Asn His Gly Ile Thr Pro Ile Val Pro Leu Arg Gly Thr
        195                 200                 205

Ile Ser Ala Ser Gly Asp Leu Ser Pro Leu Ser Tyr Ile Ala Ala Ala
210                 215                 220

Ile Ser Gly His Pro Asp Ser Lys Val His Xaa Val His Glu Gly Lys
225                 230                 235                 240

Glu Lys Ile Leu Tyr Ala Arg Glu Ala Met Ala Leu Phe Asn Leu Glu
                245                 250                 255

Pro Val Val Leu Gly Pro Lys Glu Gly Leu Gly Leu Val Asn Gly Thr
            260                 265                 270

Ala Val Ser Ala Ser Met Ala Thr Leu Ala Leu His Asp Ala His Met
            275                 280                 285

Leu Ser Leu Leu Ser Gln Ser Leu Thr Ala Met Thr Val Glu Ala Met
290                 295                 300

Val Gly His Ala Gly Ser Phe His Pro Phe Leu His Asp Val Thr Arg
305                 310                 315                 320

Pro His Pro Thr Gln Ile Glu Val Ala Gly Asn Ile Arg Lys Leu Leu
                325                 330                 335

Glu Gly Ser Arg Phe Ala Val His His Glu Glu Val Lys Val Lys
            340                 345                 350

Asp Asp Glu Gly Ile Leu Arg Gln Asp Arg Tyr Pro Leu Arg Thr Ser

```
                355                 360                 365
Pro Gln Trp Leu Gly Pro Leu Val Ser Asp Leu Ile His Ala His Ala
    370                 375                 380

Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
                405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Glu Ser Ala Ile Ser Leu Thr Arg Gln Val
625                 630                 635                 640

Arg Glu Thr Phe Trp Ser Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715

<210> SEQ ID NO 37
<211> LENGTH: 716
<212> TYPE: PRT
<213> ORGANISM: mutant from Rhodotorula glutinis
<220> FEATURE:
<221> NAME/KEY: UNSURE
<222> LOCATION: (149)..(149)
<223> OTHER INFORMATION: X= Pro, Ala, Ser, Thr, Gly
<221> NAME/KEY: UNSURE
<222> LOCATION: (202)..(202)
```

```
<223> OTHER INFORMATION: X= Val, Met, Leu, Cys
<221> NAME/KEY: UNSURE
<222> LOCATION: (540)..(540)
<223> OTHER INFORMATION: X= Thr, Ala, Ser, Pro, Gly

<400> SEQUENCE: 37
```

| | | | | | | | | | | | | | | |
|---|---|---|---|---|---|---|---|---|---|---|---|---|---|---|
| Met | Ala | Pro | Ser | Leu | Asp | Ser | Ile | Ser | His | Ser | Phe | Ala | Asn | Gly | Val |
| 1 | | | | 5 | | | | | 10 | | | | | 15 | |
| Ala | Ser | Ala | Lys | Gln | Ala | Val | Asn | Gly | Ala | Ser | Thr | Asn | Leu | Ala | Val |
| | | | 20 | | | | | 25 | | | | | 30 | | |
| Ala | Gly | Ser | His | Leu | Pro | Thr | Thr | Gln | Val | Thr | Gln | Val | Asp | Ile | Val |
| | | 35 | | | | | 40 | | | | | 45 | | | |
| Glu | Lys | Met | Leu | Ala | Ala | Pro | Thr | Asp | Ser | Thr | Leu | Glu | Leu | Asp | Gly |
| | 50 | | | | | 55 | | | | | 60 | | | | |
| Tyr | Ser | Leu | Asn | Leu | Gly | Asp | Val | Val | Ser | Ala | Ala | Arg | Lys | Gly | Arg |
| 65 | | | | | 70 | | | | | 75 | | | | | 80 |
| Pro | Val | Arg | Val | Lys | Asp | Ser | Asp | Glu | Ile | Arg | Ser | Lys | Ile | Asp | Lys |
| | | | | 85 | | | | | 90 | | | | | 95 | |
| Ser | Val | Glu | Phe | Leu | Arg | Ser | Gln | Leu | Ser | Met | Ser | Val | Tyr | Gly | Val |
| | | | 100 | | | | | 105 | | | | | 110 | | |
| Thr | Thr | Gly | Phe | Gly | Gly | Ser | Ala | Asp | Thr | Arg | Thr | Glu | Asp | Ala | Ile |
| | | 115 | | | | | 120 | | | | | 125 | | | |
| Ser | Leu | Gln | Lys | Ala | Leu | Leu | Glu | His | Gln | Leu | Cys | Gly | Val | Leu | Pro |
| | 130 | | | | | 135 | | | | | 140 | | | | |
| Ser | Ser | Phe | Asp | Xaa | Phe | Arg | Leu | Gly | Arg | Gly | Leu | Glu | Asn | Ser | Leu |
| 145 | | | | | 150 | | | | | 155 | | | | | 160 |
| Pro | Leu | Glu | Val | Val | Arg | Gly | Ala | Met | Thr | Ile | Arg | Val | Asn | Ser | Leu |
| | | | | 165 | | | | | 170 | | | | | 175 | |
| Thr | Arg | Gly | His | Ser | Ala | Val | Arg | Leu | Val | Val | Leu | Glu | Ala | Leu | Thr |
| | | | 180 | | | | | 185 | | | | | 190 | | |
| Asn | Phe | Leu | Asn | His | Gly | Ile | Thr | Pro | Xaa | Val | Pro | Leu | Arg | Gly | Thr |
| | | 195 | | | | | 200 | | | | | 205 | | | |
| Ile | Ser | Ala | Ser | Gly | Asp | Leu | Ser | Pro | Leu | Ser | Tyr | Ile | Ala | Ala | Ala |
| | 210 | | | | | 215 | | | | | 220 | | | | |
| Ile | Ser | Gly | His | Pro | Asp | Ser | Lys | Val | His | Val | Val | His | Glu | Gly | Lys |
| 225 | | | | | 230 | | | | | 235 | | | | | 240 |
| Glu | Lys | Ile | Leu | Tyr | Ala | Arg | Glu | Ala | Met | Ala | Leu | Phe | Asn | Leu | Glu |
| | | | | 245 | | | | | 250 | | | | | 255 | |
| Pro | Val | Val | Leu | Gly | Pro | Lys | Glu | Gly | Leu | Gly | Leu | Val | Asn | Gly | Thr |
| | | | | 260 | | | | | 265 | | | | | 270 | |
| Ala | Val | Ser | Ala | Ser | Met | Ala | Thr | Leu | Ala | Leu | His | Asp | Ala | His | Met |
| | | | 275 | | | | | 280 | | | | | 285 | | |
| Leu | Ser | Leu | Leu | Ser | Gln | Ser | Leu | Thr | Ala | Met | Thr | Val | Glu | Ala | Met |
| | 290 | | | | | 295 | | | | | 300 | | | | |
| Val | Gly | His | Ala | Gly | Ser | Phe | His | Pro | Phe | Leu | His | Asp | Val | Thr | Arg |
| 305 | | | | | 310 | | | | | 315 | | | | | 320 |
| Pro | His | Pro | Thr | Gln | Ile | Glu | Val | Ala | Gly | Asn | Ile | Arg | Lys | Leu | Leu |
| | | | | 325 | | | | | 330 | | | | | 335 | |
| Glu | Gly | Ser | Arg | Phe | Ala | Val | His | His | Glu | Glu | Val | Lys | Val | Lys |
| | | | 340 | | | | | 345 | | | | | 350 | |
| Asp | Asp | Glu | Gly | Ile | Leu | Arg | Gln | Asp | Arg | Tyr | Pro | Leu | Arg | Thr | Ser |
| | | | 355 | | | | | 360 | | | | | 365 | | |
| Pro | Gln | Trp | Leu | Gly | Pro | Leu | Val | Ser | Asp | Leu | Ile | His | Ala | His | Ala |
| | | | 370 | | | | | 375 | | | | | 380 | | |

-continued

```
Val Leu Thr Ile Glu Ala Gly Gln Ser Thr Thr Asp Asn Pro Leu Ile
385                 390                 395                 400

Asp Val Glu Asn Lys Thr Ser His His Gly Gly Asn Phe Gln Ala Ala
            405                 410                 415

Ala Val Ala Asn Thr Met Glu Lys Thr Arg Leu Gly Leu Ala Gln Ile
            420                 425                 430

Gly Lys Leu Asn Phe Thr Gln Leu Thr Glu Met Leu Asn Ala Gly Met
        435                 440                 445

Asn Arg Gly Leu Pro Ser Cys Leu Ala Ala Glu Asp Pro Ser Leu Ser
    450                 455                 460

Tyr His Cys Lys Gly Leu Asp Ile Ala Ala Ala Tyr Thr Ser Glu
465                 470                 475                 480

Leu Gly His Leu Ala Asn Pro Val Thr Thr His Val Gln Pro Ala Glu
                485                 490                 495

Met Ala Asn Gln Ala Val Asn Ser Leu Ala Leu Ile Ser Ala Arg Arg
            500                 505                 510

Thr Thr Glu Ser Asn Asp Val Leu Ser Leu Leu Leu Ala Thr His Leu
        515                 520                 525

Tyr Cys Val Leu Gln Ala Ile Asp Leu Arg Ala Xaa Glu Phe Glu Phe
    530                 535                 540

Lys Lys Gln Phe Gly Pro Ala Ile Val Ser Leu Ile Asp Gln His Phe
545                 550                 555                 560

Gly Ser Ala Met Thr Gly Ser Asn Leu Arg Asp Glu Leu Val Glu Lys
                565                 570                 575

Val Asn Lys Thr Leu Ala Lys Arg Leu Glu Gln Thr Asn Ser Tyr Asp
            580                 585                 590

Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715
```

<210> SEQ ID NO 38
<211> LENGTH: 716
<212> TYPE: PRT
<213> ORGANISM: mutant from Rhodotorula glutinis
<220> FEATURE:
<221> NAME/KEY: UNSURE
<222> LOCATION: (502)..(502)
<223> OTHER INFORMATION: X= Gly, Ala, Ser, Thr, Pro
<221> NAME/KEY: UNSURE
<222> LOCATION: (540)..(540)
<223> OTHER INFORMATION: X= Thr, Ala, Ser, Pro, Gly

<400> SEQUENCE: 38

Met Ala Pro Ser Leu Asp Ser Ile Ser His Ser Phe Ala Asn Gly Val

-continued

```
1               5                   10                  15
Ala Ser Ala Lys Gln Ala Val Asn Gly Ala Ser Thr Asn Leu Ala Val
                20                  25              30

Ala Gly Ser His Leu Pro Thr Thr Gln Val Thr Gln Val Asp Ile Val
            35              40              45

Glu Lys Met Leu Ala Ala Pro Thr Asp Ser Thr Leu Glu Leu Asp Gly
        50              55              60

Tyr Ser Leu Asn Leu Gly Asp Val Val Ser Ala Ala Arg Lys Gly Arg
65              70              75              80

Pro Val Arg Val Lys Asp Ser Asp Glu Ile Arg Ser Lys Ile Asp Lys
                85              90              95

Ser Val Glu Phe Leu Arg Ser Gln Leu Ser Met Ser Val Tyr Gly Val
                100             105             110

Thr Thr Gly Phe Gly Gly Ser Ala Asp Thr Arg Thr Glu Asp Ala Ile
            115             120             125

Ser Leu Gln Lys Ala Leu Leu Glu His Gln Leu Cys Gly Val Leu Pro
    130             135             140

Ser Ser Phe Asp Ser Phe Arg Leu Gly Arg Gly Leu Glu Asn Ser Leu
145             150             155             160

Pro Leu Glu Val Val Arg Gly Ala Met Thr Ile Arg Val Asn Ser Leu
                165             170             175

Thr Arg Gly His Ser Ala Val Arg Leu Val Val Leu Glu Ala Leu Thr
            180             185             190

Asn Phe Leu Asn His Gly Ile Thr Pro Ile Val Pro Leu Arg Gly Thr
        195             200             205

Ile Ser Ala Ser Gly Asp Leu Ser Pro Leu Ser Tyr Ile Ala Ala Ala
    210             215             220

Ile Ser Gly His Pro Asp Ser Lys Val His Val Val His Glu Gly Lys
225             230             235             240

Glu Lys Ile Leu Tyr Ala Arg Glu Ala Met Ala Leu Phe Asn Leu Glu
                245             250             255

Pro Val Val Leu Gly Pro Lys Glu Gly Leu Gly Leu Val Asn Gly Thr
            260             265             270

Ala Val Ser Ala Ser Met Ala Thr Leu Ala Leu His Asp Ala His Met
        275             280             285

Leu Ser Leu Leu Ser Gln Ser Leu Thr Ala Met Thr Val Glu Ala Met
    290             295             300

Val Gly His Ala Gly Ser Phe His Pro Phe Leu His Asp Val Thr Arg
305             310             315             320

Pro His Pro Thr Gln Ile Glu Val Ala Gly Asn Ile Arg Lys Leu Leu
                325             330             335

Glu Gly Ser Arg Phe Ala Val His His Glu Glu Val Lys Val Lys
            340             345             350

Asp Asp Glu Gly Ile Leu Arg Gln Asp Arg Tyr Pro Leu Arg Thr Ser
        355             360             365

Pro Gln Trp Leu Gly Pro Leu Val Ser Asp Leu Ile His Ala His Ala
    370             375             380

Val Leu Thr Ile Glu Ala Gly Gln Ser Thr Thr Asp Asn Pro Leu Ile
385             390             395             400

Asp Val Glu Asn Lys Thr Ser His His Gly Gly Asn Phe Gln Ala Ala
                405             410             415

Ala Val Ala Asn Thr Met Glu Lys Thr Arg Leu Gly Leu Ala Gln Ile
            420             425             430
```

```
Gly Lys Leu Asn Phe Thr Gln Leu Thr Glu Met Leu Asn Ala Gly Met
        435                 440                 445
Asn Arg Gly Leu Pro Ser Cys Leu Ala Ala Glu Asp Pro Ser Leu Ser
        450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
            485                 490                 495
Met Ala Asn Gln Ala Xaa Asn Ser Leu Ala Leu Ile Ser Ala Arg Arg
            500                 505                 510
Thr Thr Glu Ser Asn Asp Val Leu Ser Leu Leu Leu Ala Thr His Leu
        515                 520                 525
Tyr Cys Val Leu Gln Ala Ile Asp Leu Arg Ala Xaa Glu Phe Glu Phe
    530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
                565                 570                 575
Val Asn Lys Thr Leu Ala Lys Arg Leu Glu Gln Thr Asn Ser Tyr Asp
            580                 585                 590
Leu Val Pro Arg Trp His Asp Ala Phe Ser Phe Ala Ala Gly Thr Val
        595                 600                 605
Val Glu Val Leu Ser Ser Thr Ser Leu Ser Leu Ala Ala Val Asn Ala
    610                 615                 620
Trp Lys Val Ala Ala Ala Glu Ser Ala Ile Ser Leu Thr Arg Gln Val
625                 630                 635                 640
Arg Glu Thr Phe Trp Ser Ala Ala Ser Thr Ser Ser Pro Ala Leu Ser
                645                 650                 655
Tyr Leu Ser Pro Arg Thr Gln Ile Leu Tyr Ala Phe Val Arg Glu Glu
            660                 665                 670
Leu Gly Val Lys Ala Arg Arg Gly Asp Val Phe Leu Gly Lys Gln Glu
        675                 680                 685
Val Thr Ile Gly Ser Asn Val Ser Lys Ile Tyr Glu Ala Ile Lys Ser
    690                 695                 700
Gly Arg Ile Asn Asn Val Leu Leu Lys Met Leu Ala
705                 710                 715
```

POLYNUCLEOTIDE ENCODING A MUTANT *RHODOTORULA GLUTINIS* TYROSINE AMMONIA LYASE POLYPEPTIDE

This application is a continuation in part of U.S. application Ser. No. 09/627,216 filed on Jul. 27, 2000, now U.S. Pat. No. 6,368,837, which claims the benefit of U.S. Provisional Application No. 60/147,719 filed on Aug. 6, 1999.

FIELD OF THE INVENTION

This invention relates to the field of molecular biology and microbiology. More specifically, this invention describes a new, genetically engineered biocatalyst possessing enhanced tyrosine ammonia-lyase activity.

BACKGROUND OF THE INVENTION

Phenylalanine ammonia-lyase (PAL) (EC 4.3.1.5) is widely distributed in plants (Koukol et al., *J. Biol. Chem.* 236:2692–2698 (1961)), fungi (Bandoni et al., *Phytochemistry* 7:205–207 (1968)), yeast (Ogata et al., *Agric. Biol. Chem.* 31:200–206 (1967)), and Streptomyces (Emes et al., *Can. J. Biochem.* 48:613–622 (1970)), but it has not been found in *Escherichia coli* or mammalian cells (Hanson and Havir In *The Enzymes*, 3rd ed.; Boyer, P., Ed.; Academic: New York, 1967; pp 75–167). PAL is the first enzyme of phenylpropanoid metabolism and catalyzes the removal of the (pro-3S)-hydrogen and —$NH_3^+$ from L-phenylalanine to form trans-cinnamic acid. In the presence of a P450 enzyme system, trans-cinnamic acid can be converted to para-hydroxycinnamic acid (PHCA) which serves as the common intermediate in plants for production of various secondary metabolites such as lignin and isoflavonoids. In microbes however, cinnamic acid and not the PHCA acts as the precursor for secondary metabolite formation. No cinnamate hydroxylase enzyme has so far been characterized from microbial sources. The PAL enzyme in plants is thought to be a regulatory enzyme in the biosynthesis of lignin, isoflavonoids and other phenylpropanoids (Hahlbrock et al., *Annu. Rev. Plant Phys. Plant Mol. Biol.* 40:347–369 (1989)). However, in the red yeast, *Rhodotorula glutinis* (*Rhodosporidium toruloides*), this lyase degrades phenylalanine as a catabolic function and the cinnamate formed by the action of this enzyme is converted to benzoate and other cellular materials.

The gene sequence of PAL from various sources, including *Rhodosporidium toruloides*, has been determined and published (Edwards et al., *Proc. Natl. Acad. Sci., USA* 82:6731–6735 (1985); Cramer et al., *Plant Mol. Biol.* 12:367–383 (1989); Lois et al., *EMBO J.* 8:1641–1648 (1989); Minami et al., *Eur. J. Biochem.* 185:19–25 (1989); Anson et al., *Gene* 58:189–199 (1987); Rasmussen & Oerum, *DNA Sequence*, 1:207–211 (1991). The PAL genes from various sources have been over-expressed as active PAL enzyme in yeast, *Escherichia coli* and insect cell culture (Faulkner et al., *Gene* 143:13–20 (1994); Langer et al., *Biochemistry* 36:10867–10871 (1997); McKegney et al., *Phytochemistry* 41:1259–1263 (1996)). PAL has received attention because of its potential usefulness in correcting the inborn error of metabolism phenylketonuria (Bourget et al., *FEBS Lett.* 180:5–8 (1985); U.S. Pat. No. 5,753,487), in altering tumor metabolism (Fritz et al. *J. Biol. Chem.* 251:4646–4650 (1976)), in quantitative analysis of serum phenylalanine (Koyama et al., *Clin. Chim. Acta*, 136:131–136 (1984)) and as a route for synthesizing L-phenylalanine from cinnamic acid (Yamada et al., *Appl. Environ. Microbiol.* 42:773 (1981), Hamilton et al., *Trends in Biotechnol.* 3:64–68 (1985) and Evans et al., *Microbial Biotechnology* 25:399–405 (1987)).

In plants, the PAL enzyme converts phenylalanine to trans-cinnamic acid which in turn is hydroxylated at the para position by cinnamate-4-hydroxylase to make PHCA (Pierrel et al., *Eur. J. Biochem.* 224:835 (1994); Urban et al., *Eur. J. Biochem.* 222:843 (1994); Cabello-Hurtado et al., *J. Biol. Chem.* 273:7260 (1998); and Teutsch et al., *Proc. Natl. Acad. Sci. USA* 90:4102 (1993)). However, since further metabolism of cinnamic acid in microbial systems does not usually involve its para hydroxylation to PHCA, information regarding this reaction in microorganisms is scarce.

Information available indicates that PAL from some plants and micro-organisms, in addition to its ability to convert phenylalanine to cinnamate, can accept tyrosine as substrate. In such reactions the enzyme activity is designated tyrosine ammonia lyase (TAL). Conversion of tyrosine by TAL results in the direct formation of PHCA from tyrosine without the intermediacy of cinnamate. However, all natural PAL/TAL enzymes prefer to use phenylalanine rather than tyrosine as their substrate. The level of TAL activity is always lower than PAL activity, but the magnitude of this difference varies over a wide range. For example, the parsley enzyme has a $K_M$ for phenylalanine of 15–25 $\mu$M and for tyrosine 2.0–8.0 mM with turnover numbers 22/sec and 0.3/sec respectively (Appert et al., *Eur. J. Biochem.* 225:491 (1994)). In contrast, the maize enzyme has a $K_M$ for phenylalanine only fifteen times higher than for tyrosine, and turnover numbers about ten-fold higher (Havir et al., *Plant Physiol.* 48:130 (1971)). The exception to this rule, is the yeast, Rhodosporidium, in which a ratio of TAL catalytic activity to PAL catalytic activity is approximately 0.58 (Hanson and Havir In *The Biochemistry of Plants;* Academic: New York, 1981; Vol. 7, pp 577–625).

The above mentioned biological systems provide a number of enzymes that may be useful in the production of PHCA, however, the efficient production of this monomer has not been achieved. The problem to be overcome therefore is the design and implementation of a method for the efficient production of PHCA from a biological source using an inexpensive substrate or fermentable carbon source. Applicants have solved the stated problem by engineering both microbial and plant hosts to produce PHCA, either by the overexpression of foreign genes encoding PAL and p450/p-450 reductase system or by the expression of genes encoding mutant and wildtype TAL activity.

SUMMARY OF THE INVENTION

The object of the present invention is bioproduction of PHCA, a compound that has potential as a monomer for production of Liquid Crystal Polymers (LCP). There are two potential bio-routes for production of PHCA from glucose and other fermentable carbon substrates:

1) Conversion of phenylalanine to cinnamic acid to PHCA. This route requires the enzyme PAL as well as a cytochrome P-450 and a cytochrome P-450 reductase (Scheme 1).
2) Conversion of tyrosine to PHCA in one step without the intermediacy of cinnamate (Scheme 1). This route requires the enzyme TAL which is likely to be very similar to PAL but with a higher substrate specificity for tyrosine. This route does not require the cytochrome P-450 and the cytochrome P-450 reductase. Operation of the TAL route therefore requires generation of a biocatalyst with increased TAL activity to function through the TAL route.

Scheme 1

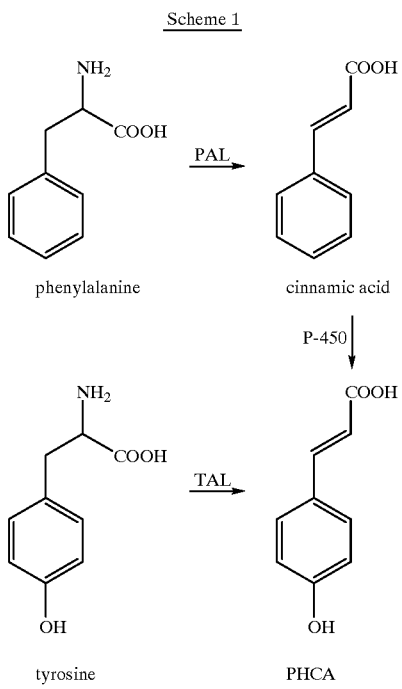

The present invention describes methods for bioproduction of PHCA through conversion of: 1) cinnamate to PHCA; 2) glucose to phenylalanine to PHCA via the PAL route and 3) through generation of a new biocatalyst possessing enhanced tyrosine ammonia-lyase (TAL) activity. The evolution of TAL requires isolation of a yeast PAL gene, mutagenesis and evolution of the PAL coding sequence, and selection of variants with improved TAL activity. The instant invention further demonstrates the bioproduction of PHCA from glucose through the above mentioned routes in various fungi and bacteria.

It is an object of the present invention therefore to provide a method for the production of PHCA comprising: (i) contacting a recombinant host cell with a fermentable carbon substrate, said recombinant cell lacking a P-450/P-450 reductase system and comprising a gene encoding a tyrosine ammonia lyase activity operably linked to suitable regulatory sequences (ii) growing said recombinant cell for a time sufficient to produce PHCA; and (iii) optionally recovering said PHCA. Within the context of the invention a fermentable carbon substrate may be selected from the group consisting of monosaccharides, oligosaccharides, polysaccharides, carbon dioxide, methanol, formaldehyde, formate, and carbon-containing amines and the host cell from the group consisting of bacteria, yeasts, filamentous fungi, algae and plant cells.

Similarly provided are recombinant host cells lacking a cytochrome P-450/P-450 reductase system and comprising a gene encoding a tyrosine ammonia lyase activity operably linked to suitable regulatory sequences.

Additionally provided is a method for the production of PHCA comprising: (i) contacting a recombinant yeast cell with a fermentable carbon substrate, said recombinant cell comprising: a) a gene encoding a plant P-450/P-450 reductase system; and b) a gene encoding a yeast PAL activity operably linked to suitable regulatory sequences; (ii) growing said recombinant cell for a time sufficient to produce PHCA; and (iii) optionally recovering said PHCA.

It is another object of the present invention to provide a method for identifying a gene encoding a TAL activity comprising: (i) contacting a recombinant microorganism comprising a foreign gene suspected of encoding a TAL activity with PHCA for a time sufficient to metabolize PHCA; and (ii) monitoring the growth the recombinant microorganism whereby growth of the organism indicates the presence of a gene encoding a TAL activity.

Similarly a method for identifying a gene encoding a TAL activity is provided comprising: (i) transforming a host cell capable of using PHCA as a sole carbon source with a gene suspected of encoding a TAL activity to create a transformant; (ii) comparing the rate of growth of the transformant with an untransformed host cell capable of using PHCA as a sole carbon source wherein an accelerated rate of growth by the transformant indicates the presence of a gene encoding a TAL activity.

Additionally the present invention provides an isolated nucleic acid fragment selected from the group consisting of: a) an isolated nucleic acid fragment encoding a truncated mutant tyrosine ammonia lyase polypeptide, the polypeptide having the amino acid sequence as set forth in SEQ ID NO:32; b) an isolated nucleic acid fragment have the nucleotide sequence as set forth in SEQ ID NO:31; and c) an isolated nucleic acid fragment completely complementary to either (a) or (b), and polypeptides encoded by the same.

Similary the invention provides an isolated nucleic acid fragment selected from the group consisting of: a) an isolated nucleic acid fragment encoding a mutant tyrosine ammonia lyase polypeptide, the polypeptide having an amino acid sequence selected from the group consisting of SEQ ID NO:10, SEQ ID NO:33, SEQ ID NO:34, SEQ ID NO:35, SEQ DI NO:36, SEQ ID NO:37 and SEQ ID NO:38; and b) an isolated nucleic acid fragment completely complementary to either (a), and polypeptides encoded by the same.

BRIEF DESCRIPTION OF THE DRAWINGS AND SEQUENCE DESCRIPTIONS AND BIOLOGICAL DEPOSITS

Figure 1:
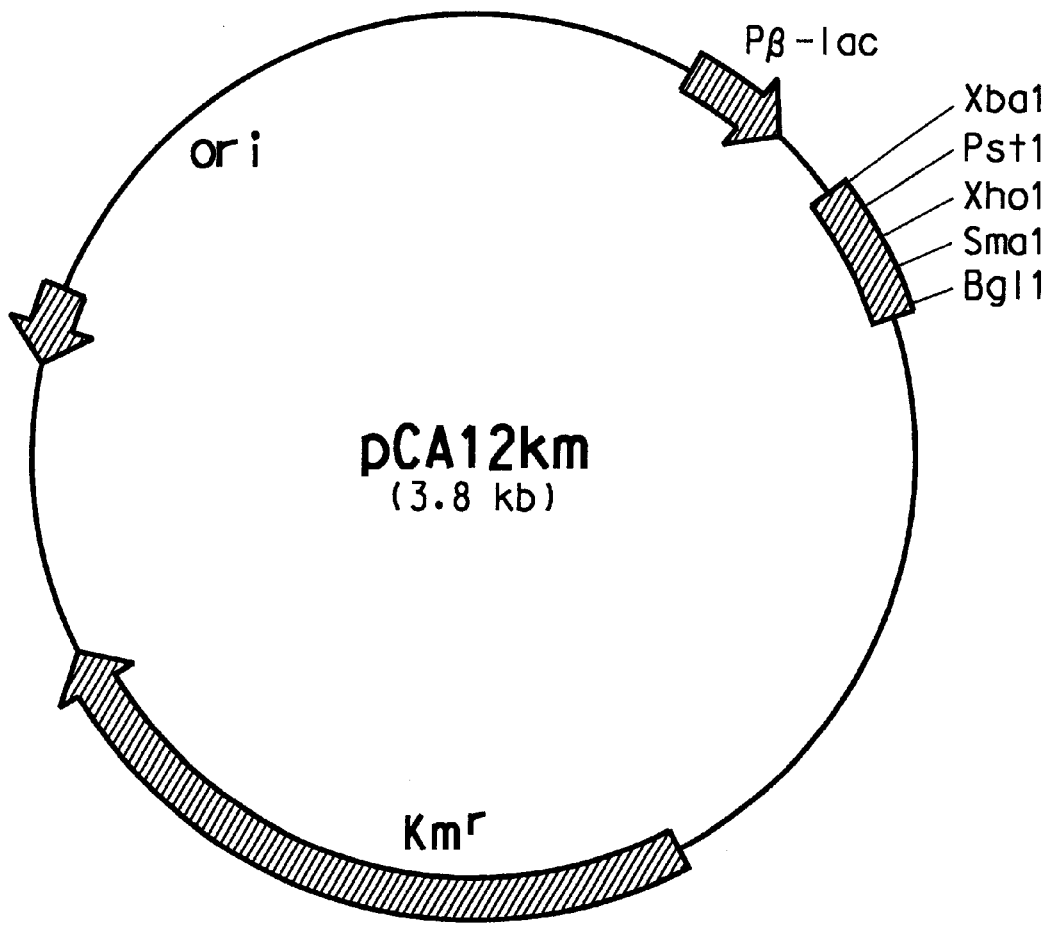
FIG. 1 is a plasmid map of the vector PCA12Km, derived from pBR322, and used for the construction of the PAL expression vector PCA18Km.

Applicants made the following biological deposits under the terms of the Budapest Treaty on the International Recognition of the Deposit of Microorganisms for the Purposes of Patent Procedure at the American Type Culture Collection (ATCC) 10801 University Boulevard, Manassas, Va. 20110-2209:

| Depositor Identification Reference | International Depository Designation | Date of Deposit |
|---|---|---|
| E. coli pKK223-3 PAL in DH10B | PTA 407 | July 21, 1999 |
| S. cereviseae containing wild-type PAL | PTA 408 | July 21, 1999 |
| S. cereviseae Aro4GSW | PTA 409 | July 21, 1999 |

The invention can be more fully understood from the following detailed description and the accompanying sequence descriptions which form a part of this application.

Applicant(s) has provided 30 sequences in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Adminstrative Instructions).

SEQ ID NOs:1–4 are primers used for vector construction.

SEQ ID NOs:5–6 are primers used for vector construction and for regional random mutagenesis of the mutant PAL enzyme.

SEQ ID NO:7 is the nucleotide sequence encoding the wildtype R. glutinis PAL enzyme.

SEQ ID NO:8 is the deduced amino acid sequence encoded by the nucleotide sequence encoding the wildtype R. glutinis PAL enzyme.

SEQ ID NO:9 is the nucleotide sequence encoding the mutant R. glutinis PAL enzyme having enhanced TAL activity.

SEQ ID NO:10 is the deduced amino acid sequence encoded by the nucleotide sequence encoding the mutant R. glutinis PAL enzyme having enhanced TAL activity.

SEQ ID NO:11 is the nucleotide sequence encoding the H. tuberosus cytochrome p-450 enzyme.

SEQ ID NO:12 is the deduced amino acid sequence encoded by the nucleotide sequence encoding the H. tuberosus cytochrome p-450 enzyme.

SEQ ID NO:13 is the nucleotide sequence encoding the H. tuberosus p-450 reductase enzyme.

SEQ ID NO:14 is the deduced amino acid sequence encoded by the nucleotide sequence encoding the H. tuberosus p-450 reductase enzyme.

SEQ ID NOs:15–23 are primers used for N-terminus truncation of the mutant PAL enzyme. SEQ ID NOs:24–30 are primers used for regional random mutagenesis of the mutant PAL enzyme.

SEQ ID NO:31 is the nucleotide sequence encoding a truncated TAL enzyme.

SEQ ID NO:32 is the amino acid sequence of a truncated TAL enzyme encoded by SEQ ID NO:31.

SEQ ID NO:33 is the amino acid sequence of a mutant TAL enzyme.

SEQ ID NO:34 is the amino acid sequence of the mutant TAL enzyme identified as RM120-1.

SEQ ID NO:35 is the amino acid sequence of the mutant TAL enzyme identified as RM120-2.

SEQ ID NO:36 is the amino acid sequence of the mutant TAL enzyme identified as RM120-4.

SEQ ID NO:37 is the amino acid sequence of the mutant TAL enzyme identified as RM120-7.

SEQ ID NO:38 is the amino acid sequence of the mutant TAL enzyme identified as RM492-1.

DETAILED DESCRIPTION OF THE INVENTION

The present invention describes biological methods for the production of PHCA. In one embodiment various bacteria and fungi were discovered that have the ability to convert trans-cinnamate to PHCA. In another embodiment yeast PAL was transformed into a host E. coli and conversion of glucose to PHCA was demonstrated. In an alternate embodiment yeast PAL and the Jerusalem Artichoke plant cytochrome P-450 and the cytochrome P-450 reductase genes were incorporated into yeast host strain and the recombinant yeast had the ability to convert glucose to PHCA. In additional embodiments, a new bio-catalyst possessing enhanced tyrosine ammonia-lyase (TAL) activity was developed and the gene encoding this activity was used to transform a recombinant host for the production of PHCA. The evolution of TAL required isolation of functional PAL gene, construction of a weak expression vector, mutagenesis and evolution of the PAL coding sequence, and selection of variants with improved TAL activity. Regional mutagenesis of a mutant with improved TAL activity led to further enhanced mutants and understanding of critical regions of the enyzme that affect TAL activity. The evolved TAL enzyme enables microorganisms to produce PHCA from tyrosine in a single step.

The following abbreviations and definitions will be used for the interpretation of the specification and the claims.

"Phenyl ammonia-lyase" is abbreviated PAL.

"Tyrosine ammonia-lyase" is abbreviated TAL.

"Para-hydroxycinnamic acid" is abbreviated PHCA.

"Cinnamate 4-hydroxylase" is abbreviated C4H.

As used herein the terms "cinnamic acid" and "cinnamate" are used interchangeably.

The term "TAL activity" refers to the ability of a protein to catalyze the direct conversion of tyrosine to PHCA.

The term "PAL activity" refers to the ability of a protein to catalyze the conversion of phenylalanine to cinnamic acid.

The term "P-450/P-450 reductase system" refers to a protein system responsible for the catalytic conversion of cinnamic acid to PHCA. The P-450/P-450 reductase system is one of several enzymes or enzyme systems known in the art that perform a cinnamate 4-hydroxylase function. As used herein the term "cinnamate 4-hydroxylase" will refer to the general enzymatic activity that results in the conversion of cinnamic acid to PHCA, whereas the term "P-450/P-450 reductase system" will refer to a specific binary protein system that has cinnamate 4-hydroxylase activity.

The term "PAL/TAL activity" or "PAL/TAL enzyme" refers to a protein which contains both PAL and TAL activity. Such a protein has at least some specificity for both tyrosine and phenylalanine as an enzymatic substrate.

The term "mutant PAL/TAL" refers to a protein which has been derived from a wild type PAL enzyme which has greater TAL activity than PAL activity. As such, a mutant PAL/TAL protein has a greater substrate specificity for tyrosine than for phenylalanine.

The term "catalytic efficiency" will be defined as the $k_{cat}/K_M$ of an enzyme. "Catalytic efficiency" will be used to quantitate the specificity of an enzyme for a substrate.

The term "$k_{cat}$" is often called the "turnover number". The term "$k_{cat}$" is defined as the maximum number of substrate molecules converted to products per active site per unit time, or the number of times the enzyme turns over per unit time. $k_{cat}$=Vmax/[E], where [E] is the enzyme concentration (Ferst In *Enzyme Structure and Mechanism*, $2^{nd}$ ed.; W. H. Freeman: New York, 1985; pp 98–120).

The term "aromatic amino acid biosynthesis" means the biological processes and enzymatic pathways internal to a cell needed for the production of an aromatic amino acid.

The term "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

"Coding sequence" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "Lineweaver-Burk plot refers a plot of enzyme kinetic data for the purpose of evaluating the kinetic parameters, $K_M$ and $V_{max}$.

The term "protein or peptide or polypeptide" will be used interchangeably and will refer to a sequence of contiguous amino acids having a defined function. "Wildtype proteins" will refer to proteins isolated from nature in an unaltered form. A "mutant protein" will refer to a wildtype protein having alterations in the amino acid sequence.

The term "amino acid" will refer to the basic chemical structural unit of a protein or polypeptide. The following abbreviations will be used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "chemically equivalent amino acid" will refer to an amino acid that may be substituted for another in a given protein without altering the chemical or functional nature of that protein. For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, alanine, a hydrophobic amino acid, may be substituted by another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Additionally, in many cases, alterations of the N-terminal and C-terminal portions of the protein molecule would also not be expected to alter the activity of the protein.

Standard recombinant DNA and molecular cloning techniques used here are well known in the art and are described by Sambrook, J., Fritsch, E. F. and Maniatis, T. *Molecular Cloning: A Laboratory Manual*, 2$^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions;* Cold Spring Harbor Laboratory: Cold Spring Harbor, N.Y., 1984; and by Ausubel, F. M. et al., In *Current Protocols in Molecular Biology,* published by Greene Publishing and Wiley-Interscience, 1987.

The present invention describes biological methods for the production of PHCA. The method makes use of genes encoding proteins having cinnamate 4-hydroxylase activity (C4H), phenylalanine ammonium-lyase (PAL) activity or tyrosine ammonium lyase (TAL) activity. A cinnamate hydroxylase activity will convert cinnamate to PHCA. Within the context of the present invention a P-450/P-450 reductase system performs this C4H function. A PAL activity will convert phenylalanine to PHCA in the presence of a P-450/P-450 reductase system. These activities are linked according to the following scheme:

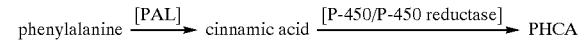

A TAL activity will convert tyrosine directly to PHCA with no intermediate step according to the following scheme:

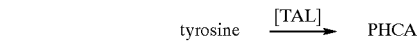

In one embodiment the method utilizes recombinant microbial host cells expressing an activity comprising both PAL and TAL functionalities in the same protein. In this embodiment the host cell lacks the P-450/P-450 reductase system and produces PHCA via the TAL route.

In another embodiment, the method utilizes a recombinant host comprising a gene encoding the PAL activity in the presence of the gene encoding the P-450/P-450 reductase system.

In an alternate embodiment the invention describes a method for the production of PHCA from cinnamate by organisms selected for their C4H activity.

The invention is useful for the biological production of PHCA which may be used as a monomer for production of Liquid Crystal Polymers (LCP). LCP's may be used in electronic connectors and telecommunication and aerospace applications. LCP resistance to sterilizing radiation has also enabled these materials to be used in medical devices as well as chemical, and food packaging applications.

Genes:

The key enzymatic activities used in the present invention are encoded by a number of genes known in the art. The principal enzymes include cinnamate-4-hydroxylase (C4H) activity (P-450/P-450 reductase), phenylalanine ammonium lyase (PAL) and tyrosine ammonium lyase (TAL).

Phenylalanine Ammonium Lyase (PAL), Tyrosine Ammonium Lyase (TAL) Activities and the P-450/P-450 Reductase System:

Genes encoding PAL are known in the art and several have been sequenced from both plant and microbial sources (see for example EP 321488 [*R. toruloides*]; WO 9811205 [*Eucalyptus grandis* and *Pinus radiata*]; WO 9732023 [Petunia]; JP 05153978 [*Pisum sativum*]; WO 9307279 [potato, rice]). The sequence of PAL genes is available (see for example GenBank AJ010143 and X75967). Where expression of a wild type PAL gene in a recombinant host is desired the wild type gene may be obtained from any source including but not limited to, yeasts such as Rhodotorula sp., Rhodosporidium sp. and Sporobolomyces sp.; bacterial organisms such as Streptomyces; and plants such as pea, potato, rice, eucalyptus, pine, corn, petunia, arabidopsis, tobacco, and parsley.

There are no known genes which encode an enzyme having exclusively TAL activity, i.e., which will use only tyrosine as a substrate for the production of PHCA. Several of the PAL enzymes mentioned above have some substrate affinity for tyrosine. Thus genes encoding TAL activity may be identified and isolated concurrently with the PAL genes described above. For example, the PAL enzyme isolated from parsley (Appert et al., *Eur. J. Biochem.* 225:491 (1994)) and corn ((Havir et al., *Plant Physiol.* 48:130 (1971)) both demonstrate the ability to use tyrosine as a substrate. Similarly, the PAL enzyme isolated from Rhodosporidium (Hodgins D S, *J. Biol. Chem.* 246:2977 (1971)) also may use tyrosine as a substrate. Such enzymes will be referred to herein as PAL/TAL enzymes or activities. Where it is desired to create a recombinant organism expressing a wild type gene encoding PAL/TAL activity, genes isolated from maize, wheat, parsley, *Rhizoctonia solani*, Rhodosporidium, *Sporobolomyces pararoseus* and Rhodosporidium may be used as discussed in Hanson and Havir, *The Biochemistry of Plants;* Academic: New York, 1981; Vol. 7, pp 577–625, where the genes from Rhodosporidium are preferred.

The invention provides a P-450/P-450 reductase system having C4H activity that is useful for the conversion of cinnamate to PHCA. This system is well known in the art and has been isolated from a variety of plant tissues. For example, the reductase as been isolated from Jerusalem Artichoke (*Helianthus tuberosus*), [embl locus HTU2NFR, accession Z26250.1]; parsley, (*Petroselinum crispum*) [Koopmann et al., *Proc. Natl. Acad. Sci. U.S.A.* 94 (26), 14954–14959 (1997), [locus AF024634 accession AF024634.1]; California poppy (*Eschscholzia californica*), Rosco et al., *Arch. Biochem. Biophys.* 348 (2), 369–377 (1997), [locus ECU67186 accession U67186.1]; *Arabidopsis thaliana,* [pir: locus S21531]; spring vetch (*Vicia sativa*), [pir: locus S37159]; mung bean, (*Vigna radiata*), Shet et al., *Proc. Natl. Acad. Sci. U.S.A.* 90 (7), 2890–2894 (1993), [pir: locus A47298]; and opium poppy (*Papaver somniferum*), [locus PSU67185 accession U67185.1].

The cytochrome has been isolated from the Jerusalem Artichoke (*Helianthus tuberosus*), [embl locus HTTC4MMR, accession Z17369.1]; *Zinnia elegans*, [swissprot: locus TCMO_ZINEL, accession Q43240] *Catharanthus roseus* [swissprot: locus TCMO_CATRO, accession P48522]; *Populus tremuloides* [swissprot: locus TCMO_POPTM, accession O24312]; *Populus kitakamiensis* [swissprot: locus TCMO_POPKI, accession Q43054]; *Glycyrrhiza echinata* [swissprot: locus TCMO_GLYEC, accession Q96423]; *Glycine max* [swissprot: locus TCMO_SOYBN, accession Q42797] as well as other sources.

Preferred in the instant invention are the genes encoding the P-450/P-450 reductase system isolated from Jerusalem Artichoke (*Helianthus tuberosus*) as set forth in SEQ ID NO:11 and SEQ ID NO:13. The skilled person will recognize that, for the purposes of the present invention, any cytochrome P-450/P-450 reductase system isolated from a plant will be suitable. As the sequence of the cytochrome gene (SEQ ID NO:11) ranges from about 92% identity (*Zinnia elegans,* Q43240) to about 63% identity (*Phaseolus vulgaris,* embl locus PV09449, accession Y09449.1) to known P-450 cytochromes in these systems, it is contemplated that any P-450 cytochrome isolated from a plant having at least 63% identity to SEQ ID NO:11 will be suitable in the present invention. Similarly, as the p-450 reductase in the system (SEQ ID NO13) ranges from about 79% identity (parsley, AF024634.1] to about 68% identity (opium poppy, U67185.1) identity to known reductases P-450's it is contemplated that any P-450 reductase isolated from a plant having at least 68% identity to SEQ ID NO:13 will be suitable in the present invention.

Methods of obtaining these or homologous wild type genes using sequence-dependent protocols are well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction (PCR), ligase chain reaction (LCR)).

For example, genes encoding homologs or anyone of the mentioned activites (PAL, TAL or the P-450/P-450 reductase system) could be isolated directly by using all or a portion of the known sequences as DNA hybridization probes to screen libraries from any desired plant, fungi, yeast, or bacteria using methodology well known to those skilled in the art. Specific oligonucleotide probes based upon the literature nucleic acid sequences can be designed and synthesized by methods known in the art (Maniatis, supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the literature sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the literature sequences, and the sequence of the other primer takes advantage of the presence of the polyadenylic acid tracts to the 3' end of the mRNA precursor encoding bacterial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the literature sequences. Using commercially available 3' RACE or 5' RACE systems (BRL), specific 3' or 5' cDNA fragments can be isolated (Ohara et al., *PNAS USA* 86:5673 (1989); Loh et al., Science 243:217 (1989)).

Mutant PAL/TAL Activities:

It is an object of the present invention to provide a mutant PAL/TAL activity having a greater substrate specificity for tyrosine than for phenylalanine. Typically the approach will involve the selection of an organism having a PAL/TAL activity with a higher substrate specificity for tyrosine than for phenylalanine. Generally, the substrate specificity is quantitated by $k_{cat}/K_M$ (catalytic efficiency), calculated on the basis of the number of active sites identified in the enzyme.

Phenylalanine ammonia-lyase has a molecular weight of about 330,000 and consists of four identical subunits of about 80 KD (Havir et al., *Biochemistry* 14:1620–1626 (1975)). It has been suggested that PAL contains a catalytically essential dehydroalanine residue (Hanson et al., *Arch. Biochem. Biophys.* 141:1–17 (1970)). Ser-202 of PAL from parsley has been indicated as the precursor of the dehydroalanine (Langer et al., *Biochemistry*, 36:10867–10871 (1997)). The $k_{cat}$ for PAL was calculated using information available from recent studies on the crystal structure of a homologous enzyme, histidine ammonia-lyase (HAL). These studies have revealed that the reactive electrophilic residue in the active site of the enzyme is a 4-methylidene-ididazole-5-one, which is autocatalytically formed by cyclization and dehydration of residues 142–144 containing the Ala-Ser-Gly sequence (Schwede et al., *Biochemistry* 38:5355–5361 (1999)). Since all tetrameric PAL enzymes studied so far, also contain the Ala-Ser-Gly sequence at each of their active sites, it is likely that each active site of PAL also contains a 4-methylidene-ididazole-5-one formed from this sequence.

Within the context of the present invention, the suitable wildtype enzyme selected for mutagenesis has a catalytic efficiency of about $4.14 \times 10^3$ to $1 \times 10^9$ $M^{-1}$ $sec^{-1}$ for tyrosine where a catalytic efficiency in a range of about of about $1 \times 10^4$ $M^{-1}$ $sec^{-1}$ to about $5 \times 10^4$ $M^{-1}$ $sec^{-1}$ is preferred.

The process of the selection of a suitable PAL/TAL enzyme, involves construction of a weak expression vector, mutagenesis and evolution of the PAL coding sequence, and finally selection of variants with improved TAL activity.

Mutagenesis of PAL:

A variety of approaches may be used for the mutagenesis of the PAL/TAL enzyme. Two suitable approaches used herein include error-prone PCR (Leung et al., *Techniques*, 1:11–15 (1989) and Zhou et al., *Nucleic Acids Res.* 19:6052–6052 (1991) and Spee et al., *Nucleic Acids Res.* 21:777–778 (1993)) and in vivo mutagenesis.

The principal advantage of error-prone PCR is that all mutations introduced by this method will be within the PAL gene, and any change may be easily controlled by changing the PCR conditions. Alternatively in vivo mutagenesis, may be employed using commercially available materials such as *E. coli* XL1-Red strain, and the *Epicurian coli* XL 1-Red mutator strain from Stratagene (Stratagene, La Jolla, Calif., Greener and Callahan, *Strategies* 7:32–34 (1994)). This strain is deficient in three of the primary DNA repair pathways (mutS, mutD and mutT), resulting in a mutation rate 5000-fold higher than that of wild-type. In vivo mutagenesis does not depend on ligation efficiency (as with error-prone PCR), however a mutation may occur at any region of the vector and the mutation rates are generally much lower.

Alternatively, it is contemplated that a mutant PAL/TAL enzyme with enhanced TAL activity may be constructed using the method of "gene shuffling" (U.S. Pat. No. 5,605,793; U.S. Pat. No. 5,811,238; U.S. Pat. No. 5,830,721; and U.S. Pat. No. 5,837,458). The method of gene shuffling is particularly attractive due to its facile implementation, and high rate of mutagenesis. The process of gene shuffling involves the restriction of a gene of interest into fragments of specific size in the presence of additional populations of DNA regions of both similarity to or difference to the gene of interest. This pool of fragments will then denature and then reanneal to create a mutated gene. The mutated gene is then screened for altered activity.

Wild type PAL/TAL sequences may be mutated and screened for altered or enhanced TAL activity by this method. The sequences should be double stranded and can be of various lengths ranging from 50 bp to 10 kb. The sequences may be randomly digested into fragments ranging from about 10 bp to 1000 bp, using restriction endonucleases well known in the art (Maniatis supra). In addition to the full length sequences, populations of fragments that are hybridizable to all or portions of the sequence may be added. Similarly, a population of fragments which are not hybridizable to the wild type sequence may also be added. Typically these additional fragment populations are added in about a 10 to 20 fold excess by weight as compared to the total nucleic acid. Generally this process will allow generation of about 100 to 1000 different specific nucleic acid fragments in the mixture. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. The salt concentration is preferably from 0 mM to 200 mM. The annealed nucleic acid fragments are next incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide of from about 50 bp to about 100 kb and may be screened for expression and altered TAL activity by standard cloning and expression protocols. (Maniatis supra).

Irrespective of the method of mutagenesis it is contemplated that a gene may be evolved having a catalytic efficiency of about $4.14 \times 10^3$ $M^{-1}$ $sec^{-1}$ to about $1 \times 10^9$ $M^{-1}$ $sec^{-1}$ where an catalytic efficiency of about $12.6 \times 10^3$ $M^{-1}$ $sec^{-1}$ is typical.

Selection of Variants with Improved TAL Activity:

Selection via Reversibility of Tyrosine to PHCA Reaction

In order to select for those mutants having genes encoding proteins with enhanced TAL activity, a selection system based on the reversibility of the tyrosine to PHCA reaction was developed. It will be appreciated that the TAL activity responsible for the conversion of tyrosine to PHCA is in a state of equilibrium with the opposite reaction. Mutant genes were cloned by standard methods into *E. coli* tyrosine auxotrophs, unable to grow in the absence of tyrosine. Transformants were plated on tyrosine minus medium in the presence of suitable concentrations of PHCA. Those colonies which grew under these conditions were picked and analyzed for the presence of the mutant gene. In this fashion, a gene was isolated that had a catalytic efficiency of about $12.6 \times 10^3$ $M^{-1}$ $sec^{-1}$ and a ratio of TAL catalytic activity to PAL catalytic activity of 1.7 compared to 0.5 for the wild type.

The skilled person will be able to envision additional screens for the selection of genes encoding enhanced TAL activity. For example, it is well known that *Acinetobacter calcoaceticus* DSM 586 (ATCC 33304) is able to efficiently degrade p-coumaric acid (PHCA) and use it as a sole carbon source (Delneri et al., *Biochim. Biophys. Acta* 1244:363–367 (1995)). The proposed pathway for this degradation is shown as Pathway I;

Pathway I

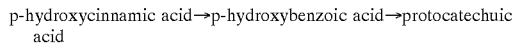

The enzymes involved in this proposed pathway are all induced by the addition of PHCA to cell cultures. By transformation of a TAL gene into *A. calcoaceticus* (ATCC 3304), or into other microorganisms able to use PHCA as a sole carbon source, the above pathway is now modified to show tyrosine as a substrate for PHCA, as illustrated in Pathway II;

Pathway II

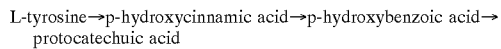

It will be appreciated that cells possessing the elements of Pathway II, when grown on PHCA will show more vigorous growth than those possessing only Pathway I. Thus, this system may be used as a screen for the identification of genes possessing TAL activity. This selection system has the added advantage of avoiding the effects of inhibitory levels of PHCA as the cell contains a pathway to degrade this compound further until the carbon enters central metabolism.

Selection via Comparison of TAL/PAL Ratio

The skilled artisan will appreciate that development of a high throughput assay for the identification of genes possessing altered PAL or TAL activity would greatly facilitate screening of microbial transformants. A simple method is dislosed that relies on separate measurements of the TAL and PAL activities in whole cells. The ratio of TAL to PAL activity then may be calculated and quickly compared to wild type activity, to monitor changes in the bio-catalyst activity.

Protein Engineering of PAL

It is now possible to attempt to modify many properties of proteins by combining information on three-dimensional structure and classical protein chemistry with methods of genetic engineering and molecular graphics, i.e. protein engineering. This approach to obtaining enzymes with altered activities relies first on the generation of a model molecule, or the use of a known structure that has a similar sequence to an unknown structure. In the instant invention, a homology model for the PAL enzyme was built and utilized, based on the crystal structure of histidine ammonialyase (HAL) (Schwede et al. *Biochemistry* 38: 5355–5361 (1999)). HAL shows 40% homology to the PAL enzyme, a sufficient degree to justify modeling since structure is conserved in evolution more than primary protein sequence. With a 3-dimensional model of PAL, it was possible to estimate which modifications in structure might bring about desired changes in the properties of the protein. Of particular interest were amino acids residues surrounding the active site of the enzyme that are involved in binding of the tyrosine or phenylalanine substrate. Applicants targeted these particular amino acids or regions of amino acids for regional site-directed mutagenesis to determine if altering them would impact the catalytic functionality of the enzyme, and thereby alter the PAL/TAL activity.

Identification of Critical Amino Acids for TAL Activity

Applicants disclose a variety of mutant PAL enzymes that have increased TAL activity, compared to the wild type gene. These mutants were identified using the methods of mutatgenesis and screening described above. The mutants, the altered amino acid residues, and the TAL/PAL activity are summarized below.

| Strain | Mutations | TAL/PAL ratio |
|---|---|---|
| Wild Type PAL | None | 0.5 |
| EPl8Km-6 (mutant PAL | CTG(Leu215) to CTC(Leu) GAA(Glu264) to GAG(Glu) GCT(Ala286) to GCA(Ala) ATC(Ile540) to ACC(Thr) | 1.7 |
| RM120-1 | GAC(Asp126) to GGC(Gly) CAG(Gln138) to CTG(Leu) CTG(Leu215) to CTC(Leu) GAA(Glu264) to GAG(Glu) GCT(Ala286) to GCA(Ala) ATC(Ile540) to ACC(Thr) | 7.2 |
| RM120-2 | TTG(Leu176) to CTG(Leu) GGC(Gly198) to CAC(Asp) CTG(Leu215) to CTC(Leu) GAA(Glu264) to GAG(Glu) GCT(Ala286) to GCA(Ala) ATC(Ile540) to ACC(Thr) | 2.1 |
| RM120-4 | TCG(Ser181) to CCG(Pro) GTC(Val235) to GCC(Ala) CTG(Leu215) to CTC(Leu) GAA(Glu264) to GAG(Glu) GCT(Ala286) to GCA(Ala) ATC(Ile540) to ACC(Thr) | 2.0 |
| RM120-7 | TCG(Ser149) to CCG(Pro) ATC(Ile202) to GTC(Val) CTG(Leu215) to CTC(Leu) GAA(Glu264) to GAG(Glu) GCT(Ala286) to GCA(Ala) ATC(Ile540) to ACC(Thr) | 0.8 |
| RM492-1 | GTC(Val502) to GGC(Gly) CTG(Leu215) to CTC(Leu) GAA(Glu264) to GAG(Glu) GCT(Ala286) to GCA(Ala) ATC(Ile540) to ACC(Thr) | 2.0 |

It will be appreciated that the invention encompases, not only the specific mutations described above, but also those that allow for the susbstitution of chemcially equavaly amino acids. So for example where a substitution of an amino acid with the aliphatic, nonpolar amino acid alanine is made, it will be expected that the same site may be substituted with the chemically equivalent amino acid serine. Thus the invention provides mutant TAL proteins having the following amino acid substitutions within the wildtype TAL amino acid seqeunce (SEQ ID NO:8):

| Sequence ID No. | Position | WT Amino Acid | Possible Amino Acids |
|---|---|---|---|
| 33 | 126 | Asp | Gly, Ala, Ser, Thr |
| | 138 | Gln | Leu, Met, Ile, Val, Cys |
| | 149 | Ser | Pro, Ala, Ser, Thr, Gly |
| | 181 | Ser | Pro, Ala, Ser, Thr, Gly |
| | 198 | Gly | Asp, Asn, Glu, Gln |
| | 202 | Ile | Val, Met, Leu, Cys |

-continued

| Sequence ID No. | Position | WT Amino Acid | Possible Amino Acids |
|---|---|---|---|
|  | 235 | Val | Ala, Gly, Ser, Thr, Pro |
|  | 502 | Val | Gly, Ala, Ser, Thr, Pro |
|  | 540 | Ile | Thr, Ala, Ser, Pro, Gly |
| 34 | 126 | Asp | Gly, Ala, Ser, Thr |
|  | 138 | Gln | Leu, Met, Ile, Val, Cys |
|  | 540 | Ile | Thr, Ala, Ser, Pro, Gly |
| 35 | 198 | Gly | Asp, Asn, Glu. Gln |
|  | 540 | Ile | Thr, Ala, Ser, Pro, Gly |
| 36 | 181 | Ser | Pro, Ala, Ser, Thr, Gly |
|  | 235 | Val | Ala, Gly, Ser, Thr, Pro |
|  | 540 | Ile | Thr, Ala, Ser, Pro, Gly |
| 37 | 149 | Ser | Pro, Ala, Ser, Thr, Gly |
|  | 202 | Ile | Val, Met, Leu, Cys |
|  | 540 | Ile | Thr, Ala, Ser, Pro, Gly |
| 38 | 502 | Val | Gly, Ala, Ser, Thr, Pro |
|  | 540 | Ile | Thr, Ala, Ser, Pro, Gly |

Additionally Applicants also disclose the importance of the N-terminus, the C-terminus, and various specific regions that are important for TAL activity in the mutant PAL enzyme. For example, it was determined that a truncation at the N-terminal region of up to 30 amino acids did not significantly alter the activity of the TAL enzyme.

Production Organisms:

Microbial Hosts

The production organisms of the present invention will include any organism capable of expressing the genes required for the PHCA production. Typically the production organism will be restricted to microorganisms and plants.

Microorganisms useful in the present invention for the production of PHCA may include, but are not limited to bacteria, such as the enteric bacteria (Escherichia, and Salmonella for example) as well as Bacillus, Acinetobacter, Streptomyces, Methylobacter, Rhodococcus and Pseudomona; Cyanobacteria, such as Rhodobacter and Synechocystis; yeasts, such as Saccharomyces, Zygosaccharomyces, Kluyveromyces, Candida, Hansenula, Debaryomyces, Mucor, Pichia and Torulopsis; and filamentous fungi such as Aspergillus and Arthrobotrys, and algae for example. The PAL, PAL/TAL and the P-450 and P-450 reductase genes of the present invention may be produced in these and other microbial hosts to prepare large, commercially useful amounts of PHCA.

Microbial expression systems and expression vectors containing regulatory sequences that direct high level expression of foreign proteins are well known to those skilled in the art. Any of these could be used to construct chimeric genes for production of PHCA. These chimeric genes could then be introduced into appropriate microorganisms via transformation to allow for expression of high level of the enzymes.

Vectors or cassettes useful for the transformation of suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the relevant genes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $1P_L$, $1P_R$, T7, tac, and trc (useful for expression in Escherichia coli).

Termination control regions may also be derived from various genes native to the preferred hosts. Optionally, a termination site may be unnecessary, however, it is most preferred if included.

Where commercial production of PHCA is desired a variety of fermentation methodologies may be applied. For example, large scale production may be effected by both batch or continuous fermentation.

A classical batch fermentation is a closed system where the composition of the media is set at the beginning of the fermentation and not subject to artificial alterations during the fermentation. Thus, at the beginning of the fermentation the medium is inoculated with the desired microorganism or microorganisms and fermentation is permitted to occur adding nothing to the system. Typically, however, the concentration of the carbon source in a "batch" fermentation is limited and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in the log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, T. D.; Biotechnology: A Textbook of Industrial Microbiology, 2nd ed.; Sinauer Associates: Sunderland, Mass., 1989; or Deshpande, M. V. Appl. Biochem. Biotechnol. 36:227, (1992), herein incorporated by reference.

Commercial production of PHCA may also be accomplished with continuous fermentation. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in their log phase of growth.

Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems strive to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

For production of PHCA via the PAL route in the presence of the P-450/P-450 reductase system any medium that will support the growth of the cells is suitable. Where, however, production of PHCA is desired as part of the natural carbon flow of the microorganism, the fermentation medium must contain suitable carbon substrates. Suitable substrates may include but are not limited to monosaccharides such as glucose, raffinose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, formaldehyde, formate or methanol for which metabolic conversion into key biochemical intermediates has been demonstrated.

Plant Hosts

Alternatively, the present invention provides for the production of PHCA in plant cells harboring the relevant PAL, PAL/TAL and the P-450 and P-450 reductase genes. Preferred plant hosts will be any variety that will support a high production level of PHCA or PHCA-glucoside conjugate. Suitable green plants will include but are not limited to soybean, rapeseed (*Brassica napus, B. campestris*), sunflower (*Helianthus annus*), Jerusalem artichoke (*Helianthus tuberosis*), cotton (*Gossypium hirsutum*), corn, tobacco (*Nicotiana tabacum*), alfalfa (*Medicago sativa*), wheat (*Triticum sp*), barley (*Hordeum vulgare*), oats (*Avena sativa,* L), sorghum (*Sorghum bicolor*), rice (*Oryza sativa*), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Overexpression of the necessary genes of the present invention may be accomplished by first constructing chimeric genes in which the coding regions are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences of the present invention should be capable of promoting expression of the present gene product. High level plant promoters that may be used in this invention include the promoter of the small subunit (ss) of the ribulose-1,5-bisphosphate carboxylase for example from soybean (Berry-Lowe et al., *J. Molecular and App. Gen.* 1:483–498 (1982)), and the promoter of the chlorophyll a/b binding protein. These two promoters are known to be light-induced in plant cells (see for example, Cashmore, A. *Genetic Engineering of Plants, an Agricultural Perspective;* Plenum: New York, 1983; pp 29–38; Coruzzi et al., *J. Biol. Chem.* 258:1399 (1983), and Dunsmuir et al., *J. Mol. Appl. Genetics* 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus that multiple events must be screened in order to obtain lines displaying the desired expression level and pattern. Such screening may be accomplished by Southern analysis of DNA blots (Southern et al., *J. Mol. Biol.* 98:503 (1975)), Northern analysis of mRNA expression (Kroczek, *J. Chromatogr. Biomed. Appl.,* 618:133–145 (1993), Western analysis of protein expression, enzymatic activity analysis of expressed gene product, or phenotypic analysis.

For some applications it will be useful to direct the gene products of the PHCA producing genes to different cellular compartments. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N., *Plant Phys.* 100:1627–1632 (1992)) added and/or with targeting sequences that are already present removed. While the references cited give examples of each of these, the list is not exhaustive and more targeting signals of utility may be discovered in the future that are useful in the invention.

Optionally it is contemplated that PHCA production in plants may be enhanced by the antisense inhibition or co-suppression of genes encoding enzymes down stream of PHCA. These enzymes may serve to transform PHCA into less useful products and prevent PHCA accumulation. Transgenic plants comprising constructs harboring genes encoding these down stream genes in antisense conformation may be useful in enhancing PHCA accumulation. Similarly, the same genes, overexpressed may serve to enhance PHCA accumulation by gene co-suppression. Thus, the skilled person will appreciate that chimeric genes designed to express antisense RNA (U.S. Pat. No. 5,107,065) for all or part of the instant down stream genes can be constructed by linking the genes or gene fragment in reverse orientation to plant promoter sequences. Either the co-suppression or antisense chimeric genes could be introduced into plants via transformation whereby expression of the corresponding endogenous genes are reduced or eliminated.

Methods of Production:

The present invention provides several methods for the bio-production of PHCA. In one embodiment cinnamate may be contacted with an organism which contains the requisite C4H activity. These organisms may be wild type or recombinant. Several organisms were uncovered by the present invention as having the ability to convert cinnamate to PCHA including *Streptomyces griseus* (ATCC 13273, ATCC 13968, TU6), *Rhodococcus erythropolis* (ATCC 4277), *Aspergillus petrakii* (ATCC 12337), *Aspergillus niger* (ATCC 10549) and *Arthrobotrys robusta* (ATCC 11856).

In an alternate embodiment, yeast PAL and the plant cytochrome P-450 and the cytochrome P-450 reductase genes were incorporated into yeast host strains and the recombinant yeast demonstrated the ability to convert glucose to PHCA. *Saccharomyces cerevisiae* was chosen for this means of production, however it will be appreciated by the skilled artisan that a variety of yeasts will be suitable, including, but not limited to those microbial production organisms described above. Similarly, glucose was employed as a carbon substrate, however a variety of other fermentable carbon substrates may be used.

In a preferred embodiment PHCA may be produced from a recombinant microorganism or plant cell which lacks a P-450/P-450 reductase system and harbors a PAL/TAL enzyme where the enzyme has a minimum level of TAL activity and the carbon flow is directed from a fermentable carbon source through tyrosine to PHCA.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

EXAMPLES

General Methods:

Procedures required for PCR amplification, DNA modifications by endo- and exonucleases for generating desired ends for cloning of DNA, ligation, and bacterial transformation are well known in the art. Standard molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions;* Cold Spring Harbor Laboratory: Cold Spring, N.Y., 1984 and by Ausubel et al., *Current Protocols in Molecular Biology*; Greene Publishing and Wiley-Interscience; 1987.

Materials and methods suitable for the maintenance and growth of bacterial cultures are well known in the art. Techniques suitable for use in the following examples may be found as set out in *Manual of Methods for General Bacteriology;* Phillipp Gerhardt, R. G. E. Murray, Ralph N. Costilow, Eugene W. Nester, Willis A. Wood, Noel R. Krieg and G. Briggs Phillips, Eds., American Society for Microbiology: Washington, D.C., 1994 or by Brock, T. D.; *Biotechnology: A Textbook of Industrial Microbiology*, 2nd ed.; Sinauer Associates: Sunderland, Mass., 1989. All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

PCR reactions were run on GeneAMP PCR System 9700 using Amplitaq or Amplitaq Gold enzymes (PE Applied Biosystems, Foster City, Calif.), unless otherwise specified. The cycling conditions and reactions were standardized according to the manufactures instructions.

The meaning of abbreviations is as follows: "sec" means second(s), "min"means minute(s), "h" means hour(s), "d" means day(s), "μL" means microliter, "mL" means milliliters, "L" means liters, "mm" means millimeters, "nm" means nanometers, "mM" means millimolar, "M" means molar, "mmol" means millimole(s), "μmole" mean micromole", "g" means gram, "μg" means microgram and "ng" means nanogram, "U" means units, and "mU" means milliunits.

Strains, Vectors and Culture Conditions:

Tyrosine auxotrophic *Escherichia coli* strain AT2471 and wild type *Escherichia coli* W3110 were originally obtained from Coli Genetic Stock Center (CGSC #4510), Yale University, New Haven, Conn.). *Epicurian coli* XL1-Red strain was purchased from Stratagene. *Escherichia coli* BL21 (DE3) cells were used for enzyme over-expression (Shuster, B. and Retey, J., *FEBS Lett.* 349:252–254 (1994)). Vector pBR322 was purchased from New England Biolab (Bevely, Mass.). pET 24d and pET 17b were purchased from Novagen (Madison, Wis.) and pKK223-3 was purchased from Amersham Pharmacia.

Growth Media for *Rhodosporidium toruloides:*

Complex Medium:

*Rhodosporidium toruloides* (ATCC number 10788) was cultured in a medium containing malt extract (1.0%), yeast extract (0.10%) and L-phenylalanine (0.10%) in deionized water. Difco certified Bacto-malt and Bacto-yeast extract were used. A solution of malt and yeast extract was autoclaved without phenylalanine. An aliquot (50 mL) of a filter-sterilized 2% solution of phenylalanine was added to the 1.0 L autoclaved malt and yeast extract solution. (Abell et al., "Phenylalanine Ammonia-lyase from Yeast *Rhodotorula glutinis*", *Methods Enzymol.* 142:242–248 (1987)).

Minimal Medium:

The medium contained 50 mM potassium phosphate buffer (pH 6.2), $MgSO_4$ (100 mg/L), biotin (10 mg/L) and L-phenylalanine (2.5 g/L) in deionized water. A solution of phosphate buffer was autoclaved without the other ingredients. A solution of L-phenylalanine (25 g/L), $MgSO_4$ (1.0 g/L) and biotin (0.1 g/L) in 1.0 l of 50 mM potassium phosphate buffer (pH 6.2) was filter sterilized and 100 mL added to 900 mL of the autoclaved phosphate buffer. Final concentrations of the ingredients were: $KH_2PO_4$ (5.55 g/L); $K_2HPO_4$ (1.61 g/L) $MgSO_4$ (100 mg/L); biotin (10 mg/L) and L-phenylalanine (2.5 g/L) (Marusich, W. C., Jensen, R. A. and Zamir, L. O. "Induction of L-Phenylalanine Ammonia-Lyase During Utilization of Phenylalanine as a Carbon or Nitrogen Source in *Rhodosporidium toruloides*", *J. Bacteriol.* 146:1013–1019 (1981)).

Enzyme Activity Assay:

The PAL or TAL activity of the purified enzymes were measured using a spectrophotometer according to Abell et al., "Phenylalanine Ammonia-lyase from Yeast *Rhodotorula glutinis,*" *Methods Enzymol.* 142:242–248 (1987). The spectrophotometric assay for PAL determination was initiated by the addition of the enzyme to a solution containing 1.0 mM L-phenylalanine and 50 mM Tris-HCl (pH 8.5). The reaction was then followed by monitoring the absorbance of the product, cinnamic acid, at 290 nm using a molar extinction coefficient of 9000 $cm^{-1}$. The assay was run over a 5 min period using an amount of enzyme that produced absorbance changes in the range of 0.0075 to 0.018/min. One unit of activity indicated deamination of 1.0 μmol of phenylalanine to cinnamic acid per minute. The TAL activity was similarly measured using tyrosine in the reaction solution. The absorbance of the para-hydroxycinnamic acid produced was followed at 315 nm and the activity was determined using an extinction coefficient of 10,000 cm$^{-1}$ for PHCA. One unit of activity indicated deamination of 1.0 μmol of tyrosine to para-hydroxycinnamic acid per minute.

SDS Gel Electrophoresis:

The 8–25% native PhastGels were run with 4.0 μg of protein per lane and stained with Coomassie blue. Pharmacia High Molecular Weight (HMW) markers and grade I PAL from Sigma were used as standards.

Sample Preparation for HPLC Analysis:

An HPLC assay was developed for measuring the levels of cinnamic acid and PHCA formed by the whole cells. In a typical assay, following centrifugation of a culture grown in the medium of choice, 20–1000 μL of the supernatant was acidified with phosphoric acid, filtered through a 0.2 or 0.45 micron filter and analyzed by the HPLC to determine the concentration of PHCA and cinnamic acid in the growth medium. Alternatively, following centrifugation, the cells were resuspended in 100 mM Tris-HCl (pH 8.5) containing 1.0 mM tyrosine or 1.0 mM phenylalanine and incubated at room temperature for 1.0–16 h. A filtered aliquot (20–1000 μL) of this suspension was then analyzed.

The HPLC Method:

A Hewlett Packard 1090M HPLC system with an auto sampler and a diode array UV/vis detector was used with a reverse-phase Zorbax SB-C8 column (4.6 mm×250 mm) supplied by MAC-MOD Analytical Inc. Flow rate of 1.0 mL per min, at column temperature of 40° C. was carried out. The UV detector was set to monitor the eluant at 250, 230, 270, 290 and 310 nm wavelengths.

Solvents/Gradients:

| Time (min) | Solvent A<br>Methanol | Solvent B<br>0.2% TFA |
|---|---|---|
| 0.0 | 10% | 90% |
| 0.1 | 10% | 90% |
| 9.0 | 35% | 65% |
| 9.1 | 50% | 50% |
| 14.0 | 50% | 50% |
| 18.0 | 0% | 0% |
| 21.0 | 0% | 0% |

Retention time (RT) of related metabolites using the HPLC system described above are summarized below.

| Compounds (1.0 mM) | RT (min) |
|---|---|
| 1. tyrosine | 6.7 |
| 2. phenylalanine | 9.4 |
| 3. 4-hydroxybenzoic acid (PHBA) | 11.6 |
| 4. 3,4-dihydroxycinnamate (caffeic acid) | 12.5 |
| 5. 3-(4-hydroxyphenyl)propionate | 13.3 |
| 6. 4-hydroxyphenylpyruvate | 13.6 |
| 7. 4-hydroxyacetaphenone | 14.0 |
| 8. 4-hydroxycinnamic acid (PHCA) | 14.2 |
| 9. 2-hydroxycinnamic acid (OHCA) | 15.3 |
| 10. benzoic acid | 15.5 |
| 11. coumarin | 16.0 |
| 12. cinnamyl alcohol | 17.3 |
| 13. phenylpyruvate | 18.1 |
| 14. cinnamic acid | 18.3 |

MONO Q Buffer:

The buffer used for these analyses was a 50 mM potassium phosphate, pH 7.0, as the starting buffer followed by a 400 mM potassium phosphate buffer, pH 7.2 as eluent for the Mono-Q column.

EB Buffer:

The buffer used for gene cloning was 10 mM Tris-HCl (pH 8.5) buffer.

Example 1

Microorganisms for Conversion of Cinnamic Acid to PHCA

Example 1 describes screening of various microorganisms for the presence of cinnamate hydroxylases and investigation of their ability to convert cinnamic acid to PHCA.

In order to discover microorganisms with cinnamate hydroxylase activity, over 150 different strains of bacteria and fungi were screened for their ability to convert cinnamic acid to PHCA. A two-stage fermentation protocol was used. Microorganisms were first grown in the medium for three days and then a 20% inoculum was used to start the second stage cultures. Following 24 h growth in stage two, cinnamic acid was added, samples were taken at intervals and analyzed by HPLC for the presence of PHCA.

Growth Media:

ATCC Medium #196—Yeast/malt Medium

This medium contained (in grams per liter): malt extract, 6.0; maltose, 1.8; dextrose, 6.0; and yeast extract, 1.2. The pH was adjusted to 7.0.

ATCC Medium #5—Sporulation Broth

This medium contained (in grams per liter): yeast extract, 1.0; beef extract, 1.0; tryptone, 2.0; and glucose, 10.0.

Soybean Flour/Glycerol Medium (SBG):

This medium contained (in grams per liter): glycerol, 20; yeast extract, 5.0; soybean flour, 5.0; sodium chloride, 5.0; potassium phosphate dibasic, 5.0. The pH was adjusted to 7.0.

Potato-Dextrose/Yeast Medium (PDY):

This medium which contained (in grams per liter): potato dextrose broth, 24.0; yeast extract, 5.0; was used for growth of fungal strains.

Of the 100–150 microorganisms tested, three separate strains of *Streptomyces griseus* (ATCC 13273, ATCC 13968, TU6), the bacterium *Rhodococcus erythropolis* (ATCC 4277), and the fungal strains, *Aspergillus petrakii* (ATCC 12337), *Aspergillus niger* (ATCC 10549) and *Arthrobotrys robusta* (ATCC 11856) demonstrated the ability to convert cinnamic acid to PHCA. The results indicated that Streptomycetes, in general, and *Streptomyces griseus*, in particular, appeared to be most active in this hydroxylation. Further studies were therefore performed using the following strains of *Streptomyces griseus* (ATCC 13273, ATCC 13968, TU6).

The ability of the *Streptomyces griseus* strains to para-hydroxylate cinnamic acid to PHCA while growing in three complex media (SBG, sporulation broth and yeast/malt media) was examined. The two stage fermentation protocol with SBG, sporulation broth and malt/yeast media was used. Samples were taken at various time intervals and analyzed by HPLC for the presence of PHCA. Data is shown below in Table 1.

TABLE 1

Effect of Different Media on the Ability of Various Strains of
Streptomyces griseus to Convert Cinnamic Acid to PHCA

| | PHCA Production ($\mu$M) | | |
|---|---|---|---|
| | malt/yeast | SBG | sporulation broth |
| Strain 13273: | | | |
| 4 h | 0.93 | 116.81 | 2.75 |
| 18 h | 0 | 360.75 | 14.31 |
| 24 h | 5.36 | 407.27 | 12.14 |
| 42 h | 0 | 350.08 | 7.26 |
| 60 h | 0 | 363.94 | 9.79 |
| Strain TU6: | | | |
| 4 h | 0 | 2.54 | 0.62 |
| 18 h | 0 | 20.76 | 0.64 |
| 24 h | 1.23 | 22.23 | 0.54 |
| 42 h | 0.93 | 30.46 | 0.95 |
| 60 h | 1.24 | 50.82 | 1.84 |
| Strain 13968: | | | |
| 4 h | 0 | 2.92 | 41.82 |
| 18 h | 0 | 6.02 | 267.38 |
| 24 h | 0 | 20.55 | 282.29 |
| 42 h | 0 | 127.25 | 177.44 |
| 60 h | 0 | 172.78 | 160.71 |

As is seen by the data, among *Streptomyces griseus* strains tested, ATCC 13273 followed by ATCC 13968 and TU6 were the most active in producing PHCA when grown in the SBG medium. With ATCC 13968 strain of *Streptomyces griseus* growth in both SBG and sporulation broth resulted in the ability to convert cinnamic acid to PHCA. Cells (ATCC 13968) grown on sporulation medium showed the highest ability to produce PHCA after 24 h of growth while those grown on SGB medium reached their maximum PHCA producing activity after 60 h.

Example 2

Screening of Microorganisms Containing Optimal TAL/PAL Activity Ratio

Example 2 describes the screening of various microorganisms for their PAL and TAL activities. This information was required to allow for selection of the most suitable microbe for further cloning, expression, purification and kinetic analysis of the PAL and PAL/TAL enzyme.

Medium for Growth and Induction of PAL in Streptomyces:

A two stage fermentation protocol was used for Streptomyces. Stage I medium contained, glucose (2%); soybean flour (1%); yeast extract (0.5%); meat extract (0.3%); calcium carbonate (0.3%); used 4% inoculum for stage II. Stage II medium contained, glucose (2%); yeast extract (2%); sodium chloride (0.5%); calcium carbonate (0.3%). The medium was distributed at 100 mL portions into 500 mL flasks. Cells transferred to this medium were incubated for 24 h at 25° C. on a shaker.

Preparation of Cells of *Rhodosporidium toruloides* Following Growth in the Complex Medium:

In order to determine the growth yield and PAL/TAL specific activity *Rhodosporidium toruloides* cells were grown in 50 mL (in 250 mL capacity DeLong flasks) of complex medium. The yield (wet weight of cells) was 8.11 grams. The second transfer was made into 200 mL (in 10×one liter DeLong flasks) using 0.8 g (wet weight) from the initial harvest. The yield was 16.0 grams after 3 washes with 100 mM phosphate buffer (pH 7.1).

Preparation of Cell Extracts:

The cell pellet was resuspended with 0.5 mL/g cells, 50 mM Tris-HCl buffer (pH 8.5) and disrupted by a single passage through the French Pressure Cell at 20,000 psi. The disrupted cells were then centrifuged for 30 min at 14,200×g to remove the unbroken cell mass. Samples of the extract were used for protein concentration assay and the PAL/TAL activity determination. Protein determination was performed by the BCA (bicinchoninic acid) method from Pierce Co.

Gels:

Precast 7.5% acrylamide gels from BioRad (Cambridge, Mass.) were used. Cell extracts or samples of enzyme solutions were loaded on the gel along with molecular weight standards were from Pharmacia (Upsula, Sweden). The High Molecular Weight (HMW) lyophilized proteins were solubilized in 100 $\mu$L of 50 mM Tris-HCl pH 8.5 and bromophenol blue was added. The running buffer from BioRad was prepared from a 10× solution and the gels were run at 150 volts. The running dye was electrophoresed off the gel, the gels were run for an additional 1 h. One end of the gels containing the molecular weight marker and the sample lanes was cut off and stained with Coomassie blue for approximately 45 min. Two sections of the gel were cut out and the gel material cut up and placed into 1.0–2.0 mL of 50 mM Tris-HCl buffer pH 8.5 at 4° C. PAL activity was then measured at two different time intervals. The gel slices contained a maximum of 173 mU of PAL activity, determined as described above.

PAL/TAL Activity:

The PAL/TAL activity was determined as described above. Using this procedure, specific activities of 0.0241±0.0005 U/mg and 0.0143±0.0005 U/mg were observed for PAL and TAL, respectively (Table 2). Based on these results, the ratio of PAL/TAL was calculated to be 1.68±0.07. A PAL/TAL ratio of 2.12 was observed for the purified enzyme. A literature value of 1.7 has been reported for these enzymes (Hanson and Havir In *The Biochemistry of Plants;* Academic: New York, 1981; Vol. 7, pp 577–625). The complete data is shown in Table 2.

TABLE 2

PAL and TAL Activity Observed in
Cell Free Extracts of Various Microorganisms

| | | | Specific Activity | | Ratio of |
|---|---|---|---|---|---|
| ATCC # | Name | Medium | PAL(U/mg) | TAL(U/mg) | PAL/TAL |
| 15873 | *Streptomyces griseus* | SBG | 0.0 | ND | ND |
| | *Streptomyces griseus* | SBG + Phe | 0.0004 | ND | ND |
| | *Streptomyces griseus* | Strep. + Phe | 0.0003 | ND | ND |
| 13495 | *Streptomyces verticillat* | 1 | 0.0025 | ND | ND |

TABLE 2-continued

PAL and TAL Activity Observed in
Cell Free Extracts of Various Microorganisms

| ATCC # | Name | Medium | Specific Activity | | Ratio of |
|---|---|---|---|---|---|
| | | | PAL(U/mg) | TAL(U/mg) | PAL/TAL |
| 11386 | Sporidiobolus pararoseus | 2 | 0.0158 | 0.0024 | 6.51 |
| 20804 | Rhodotorula graminis | 3 | 0.0436 | 0.0102 | 4.27 |
| 2080 | Saccharomycopsis fibulige | 4 | 0.0070 | 0.0016 | 4.27 |
| 10788 | Rhodotorula glutinis | 3 | 0.0241 | 0.0143 | 1.68 |

ND: not determined
1. Grown in medium in Can. J. Biochem. 48:613–622 (1970) at 25° C.
2. Grown in 0.7% Difco malt extract, 0.1% Difco yeast extract and 0.1% phenylalanine at 30° C.
3. Grown in 1% malt extract, 0.1% yeast extract and 0.1% phenylalanine medium at 30° C.
4. Grown in 1% peptone, 1% yeast extract, 0.5% phenylalanine, 0.1% $KH_2PO_4$, 0.3% $KHPO_4$ and 0.05% $MgSO_4.7H_2O$ at 25° C.

As outlined in Table 2, Rhodosporidium toruloides also known as Rhodotorula glutinis (ATCC 10788) possesses the highest TAL activity and was therefore selected for further studies.

Example 3

Cloning and Expression of Rhodosporidium toruloides PAL in E. coli

Example 3 describes the cloning and expression of phenylalanine ammonia lyase (PAL) from Rhodosporidium toruloides in E. coli in order to produce sufficient quantities of PAL for purification.

RNA Purification:

The Rhodosporidium toruloides RNA was purified from exponential phase cells grown in the complex medium containing phenylalanine. The total RNA was isolated and the mRNA was purified using Qiagen total RNA and mRNA isolation kits, respectively, according to the manufacturers instructions.

Reverse Transcription:

The Rhodosporidium toruloides mRNA (3 μL, 75 ng) was reversed transcribed according to Perkin Elmer (Norwich Conn.) GeneAmp kit instructions without diethylpyrocarbonate (DEPC) treated water. The PCR primers used (0.75 μM) were the random hexamers supplied with the kit, the upstream primer (SEQ ID NO:1) 5'-ATAGTAGAATTCATGGCACCCTCGCTCGACTCGA-3' containing a EcoRI restriction site, and a downstream PCR primer (SEQ ID NO:2) 5'-GAGAGACTGCAGAGAGGCAGCCAAGAACG-3' containing a PstI restriction site. These were synthesized from the Rhodosporidium toruloides PAL gene. A positive control using the kit pAW109 RNA and the DM151 and DM152 primers was also performed. PCR was carried out for 30 cycles with a 95° C. melting temperature for 1.0 min, a 55° C. annealing temperature for 1.0 min and a 72° C. elongation temperature for 2.0 min. Five sec were added per cycle to the elongation step and a final elongation step of 10 min was used. An aliquot (5.0 μL) was taken from the PCR reaction mix and loaded onto a 1% agarose gel to verify the PCR reaction product.

Digestion of PCR fragments was achieved by using 10× multibuffer (2.0 μL), bovine serum albumin (BSA, 10 mg/mL, 1.0 μL), EcoRI and PstI (0.5 μL each), PCR product (4.0 μL) and distilled deionized water (12.5 μL). The entire reaction was loaded onto a 1% agarose gel and the desired size of the DNA fragments were purified.

Ligation:

The ligation mixture (total vol. 50 μL) for constructs contained: ligation buffer (10×, 5.0 μL), 3.0 U/μL T4 DNA ligase (1.0 μL), BSA (10 mg/mL, 2.5 μL), 19 ng/μL PCR product using primers with EcoRI and PstI restriction sites (25 μL), 33 ng/μL pKK223-3 previously cut with EcoRI and PstI (2.0 μL) and distilled deionized water (14.5 μL). The ligation mixture (total vol. 50 μL) for the control vector contained, ligation buffer (10×, 5.0 μL), 3.0 U/μL T4 DNA ligase (1.0 μL), BSA (10 mg/mL, 2.5 μL), 33 ng/μL pKK223-3 previously cut with EcoRI and PstI (2.0 μL), and distilled deionized water (39.5 μL). The reaction mixtures were incubated overnight at 16° C.

Transformation:

Competent DH10b E. coli cells (Gibco) were thawed on ice for approximately 20 min. Then, 2.0 μL of the ligation mix were added to 50 μL of the cells and incubated on ice for 30 min. The cells were heat shocked for 20 sec at 37° C. and then chilled on ice again. Then, 0.95 μL of LB broth was added to the cells and incubated for 1.0 h at 37° C. on a shaker. The cells were then centrifuged, resuspended in approximately 50 μL of the LB broth and streaked on LB plates containing 100 mg/L ampicillin and incubated overnight at 37° C.

Clones:

The Rhodosporidium toruloides PAL gene was over-expressed in E. coli. The PCR product, which was prepared in this example, was first cloned into a standard cloning vector and then cloned into pKK223-3 over-expression vector under the tac promoter in DH10b E. coli. A total of six clones were tested for both whole cell and cell free PAL activity.

Cell Growth:

Cells were initially grown overnight, at 37° C. on 50 mL LB media with 100 mg/L ampicillin in baffled 250 mL flask. Before harvesting the non-induced cells, a 5.0 mL aliquot was transferred into the fresh medium and grown to about 0.9 ($OD_{600}$). IPTG was then added to a final concentration of 0.2 mg/mL to induce the enzyme and the cells were further grown for 3.0 h. $OD_{600}$ measurements are shown in Table 3.

TABLE 3

Growth and PHCA Production mAU's

| Medium | Glucose | Time (hr) | $OD_{600}$ | Cinn. 270 nm | PHCA 310 mn | [Cinn.] ($\mu$M) | [PHCA] ($\mu$M) | Cinn. ($\mu$M/$OD_{600}$) | PHCA ($\mu$M/$OD_{600}$) |
|---|---|---|---|---|---|---|---|---|---|
| LB | 0 | 24 | ND | 10689.27 | 5000.41 | 839.42 | 629.50 | | |
| LB | 0.2% | 24 | ND | 12000.60 | 3540.89 | 942.40 | 445.76 | | |
| M9 | 0.2% | 24 | 0.2377 | 418.84 | 336.98 | 32.89 | 42.42 | 138.37 | 178.47 |
| M9 | 2% | 24 | 0.2079 | 411.03 | 370.11 | 32.28 | 46.59 | 155.26 | 224.11 |
| LB | 0 | 72 | 2.1010 | 12698.07 | 7942.28 | 997.17 | 999.85 | 474.62 | 475.89 |
| LB | 0.2% | 72 | 4.2740 | 14038.05 | 8416.65 | 1102.40 | 1059.57 | 257.93 | 247.91 |
| Cinn. | | | | 12734.13 | | | | | |
| PHCA | | | | | 7943.46 | | | | |

Whole Cell PAL Activity:

Aliquots of non-induced (1.0 mL) and induced (0.2 mL) cells were taken before harvest. The cells were pelleted and resuspended in 1.0 mL of 50 mM Tris buffer pH 8.5. Phenylalanine was then added (1.0 mM, final concentration) and the mixtures were incubated on the shaker at 37° C. for 1.0 h. The mixtures were then acidified with 50 $\mu$L of phosphoric acid and the cells were pelleted. The solute was then filtered and analyzed by HPLC as described above. The culture media from the induced cells was similarly treated and analyzed by HPLC. Cinnamic acid and PHCA standards (1.0 mM) were also analyzed and used to calculate the concentration of the compounds in the samples (e.g., (177.66 mAU sample)/(12734.13 mAU/mM standard)* (1000 $\mu$M/mM)=13.95 $\mu$M cinnamic acid). Results are shown in Table 3.

Cell Free PAL Activity:

Cells were harvested by centrifugation. To the harvested cell pellet, 1.0 mL of 50 mM Tris buffer (pH 8.5) was added and the cells were disrupted by a single passage through the French Pressure Cell at approximately 18,000 psi. The extract was centrifuged for 10–15 min in an Ependorf Microfuge at 4° C. The supernatant (1.0 mL) was removed and used for PAL activity and Bradford protein assays (Bradford, M., *Anal. Biochem.*, 72, 248, 1976). The highest specific activities observed, were 0.244 (PAL) and 0.0650 (TAL) U/mg protein.

SDS Gel Electrophoresis:

The purified PAL protein was run on a 8–25% native PhastGel as described in General Methods. The molecular weight of the purified PAL was estimated to be 287 kD based on these analyses.

During the above experiments, it was discovered that both PHCA and cinnamic acid appeared during growth of the cells in the LB medium and also during the whole cell assays. Detection of PHCA in transformed *E. coli* cultures was an unexpected discovery since *E. coli* does not contain the enzymatic machinery for conversion of cinnamic acid to PHCA. Presence of PHCA in these cultures therefore indicated that the wild type yeast PAL enzyme expressed in *E. coli*, in addition to its PAL activity, contained the TAL activity and directly converts tyrosine to PHCA.

Example 4

PHCA Production from Glucose by Recombinant *E. coli* Over-Expressing the *Rhodosporidium toruloides* Wild Type PAL This Example describes analysis of the *E. coli* strain over-expressing the wild type PAL for its ability to produce PHCA during growth in either glucose or the LB medium.

As described above, there are two pathways to synthesize PHCA. In one pathway, PHCA can be synthesized through conversion of phenylalanine by PAL to trans-cinnamic acid which is in turn hydroxylated at the para position by the cytochrome P-450 enzyme system. In the other pathway, tyrosine is converted to PHCA in a single step reaction by TAL and no cytochrome P-450 is required. Since no cytochrome P-450 enzyme is present in *E. coli*, any PHCA formed in these cells should be through the TAL route. To confirm this hypothesis, the following experiments were carried out: *E. coli* cells containing PCA12Km (described in Example 8) were incubated overnight with 1.0 mM cinnamic acid, and the PHCA production was monitored by HPLC.

Cell Growth:

The cells were grown overnight, in LB broth, LB+0.2% glucose with 100 mg/L ampicillin at 30° C. or in the M9 medium (see below)+0.2% glucose or the M9 medium+2% glucose with 100 mg/L ampicillin for 24 h at 30° C. The cells grown in the M9 medium+glucose grew significantly more slowly than the cells in the LB medium.

Assay of PHCA:

An aliquot (1.0 mL) of each cell culture was acidified with 50 $\mu$L of phosphoric acid and pelleted and the supernatant was filtered and analyzed by HPLC as described in the General Methods. Samples were taken after 24 or 72 h. A PHCA standard (1.0 mM) was also analyzed and used to determine the concentration of the compound in the samples. Samples were also taken to measure the cell density at 600 nm in order to relate growth to PHCA production (see Table 3, Example 2).

As can be seen from the data in Table 3, the *E. coli* cells containing the wild type PAL produced PHCA when grown in either the LB (with and without glucose) or M9 (see below) with glucose medium. The addition of glucose to the LB medium increased the total amount of PHCA formed and the cell density of the culture, but decreased the PHCA production per cell density.

M9 Medium:

The M9 minimal medium for culturing bacteria contains (in gram per liter): $Na_2HPO_4$, 6.0; $KH_2PO_4$, 3.0; $NH_4Cl$, 1.0; NaCl, 0.5; and glucose, 4. (Maniatis, Appendix A.3).

Example 5

Purification of the Recombinant Wild Type *Rhodosporidium toruloides* PAL from *E. coli*

The wild type recombinant *R. toruloides*_PAL from transformed *E. coli* was purified using heat treatment, ammonium sulfate precipitation, anion exchange column, and hydrophobic interaction chromatography and gel filtration.

Cell Growth:

The cells were grown in a 10-L fermenter at 28° C. on 2× YT medium with 100 mg/L ampicillin.

Preparation of Cell Free Extracts:

The cells were harvested and kept as a frozen pellet until required for use. The pellet (76 g wet weight) was washed with 50 mM Tris-HCl pH 8.5 and resuspended with the same buffer to a density of 2.0 g wet weight of cells per 1.0 mL of buffer. A small amount of DNase was added and the cells were passed twice through a French Pressure Cell at approximately 18,000 psi. The protease inhibitor, PMSF, was then added to the extract to a final concentration of 0.5 mM. The cell debris was removed by centrifugation at 13,000×g for 30 min followed by another centrifugation at 105,000×g for 1.0 h.

Heat Treatment of Extract:

The extracts were heated to a temperature of 60° C. for 10 min and then placed on ice. The denatured proteins were pelleted by centrifugation at 25,000×g for 30 min.

Ammonium Sulfate Precipitation:

Ammonium sulfate precipitation was achieved by addition of saturated solutions of ammonium sulfate at 4° C. The solution was stirred on ice for 15–30 min. The precipitated protein was pelleted by centrifugation at 25,000×g for 15 min and the pellet dissolved in a minimal amount of Tris buffer. During the 35% ammonium sulfate cut, the pH of the solution was measured and adjusted back to 8.5. The volume of the extract was measured after each precipitation. The extracts were ammonium sulfate precipitated separately, but the 50% ammonium sulfate cuts from both runs were pooled, concentrated and desalted with Centricon-50 ultrafiltration tubes (Milipore, Bedford, Mass.).

Anion Exchange Chromatography:

Anion exchange chromatography was carried out on a 20 mm×165 mm, 50 μm HQ column (Perseptive Biosystems, Farmingham, Mass.) at a flow of 30 mL/min. The starting buffer (buffer A) was 5 mM Tris-HCl pH 8.5 and the eluting buffer (buffer B) was 0.5 M NaCl in 5.0 mM Tris-HCl pH 8.5. The column was equilibrated for two column volumes (CV) and washed for two CV with buffer A after sample injection. A gradient was run from 100% of buffer A to 50% of buffer A and buffer B over 10 CV. A second gradient was then run from 50% of buffer A and buffer B to 100% of buffer B over two CV. The column was washed with two CV of buffer B and then re-equilibrated with buffer A for two CV. Protein was monitored at 280 nm and 10 ml fractions were collected on ice during the first gradient. The sample size was up to 5.0 ml and contained up to 340 mg of protein or approximately 12% of the column's capacity of 2850 mg. Fractions from the different runs were pooled and concentrated as indicated above.

Hydrophobic Interaction Chromatography:

Hydrophobic interaction chromatography was carried out on a 20 mm×167 mm, 50 μm PE column (Perseptive Biosystems, Farmingham, Mass.) at a flow rate of 30 mL/min. The starting buffer (buffer A) was 1.0 M $(NH_4)_2SO_4$ in 5.0 mM Tris-HCl pH 8.5 and the eluting buffer (buffer B) was 5.0 mM Tris-HCl pH 8.5. The column was equilibrated for two CV and washed for two CV with buffer A after sample injection. A gradient was then run from 100% of buffer A to 100% of buffer B over 10 CV. The column was cleaned with 2 CV of buffer B and then re-equilibrated with buffer A for two CV. Protein was monitored at 280 nm and 10 mL fractions were collected and kept on ice during the gradient. Samples, up to 5.0 mL and containing up to 50 mg of protein or 12% of the column's capacity of 420 mg, were adjusted to 1.0 M $(NH_4)_2SO_4$ by the addition of a saturated ammonium sulfate solution. Fractions from different runs were pooled, desalted and concentrated as indicated above.

Gel Filtration Chromatography (GF):

Gel filtration was carried out on a 10 mm×305 mm, Superdex 200HR column at a flow rate of 0.5 mL/min. Using a 50 mM Tris-HCl buffer (pH 8.5) containing 0.2 M NaCl, a column was run for one CV and protein elution monitored at 280 nm. Fractions (0.5 mL) were collected and kept on ice. The volume of the sample applied to the column was 100 μL and contained up to 10 mg of protein. The fractions from the center of the peaks were pooled and concentrated as described above.

Data describing the purification and increase in specific activity are shown in Table 4.

TABLE 4

| | Purification of PAL from *E. coli* | | | | | | | |
|---|---|---|---|---|---|---|---|---|
| Step | Vol. (mL) | Protein (mg/mL) | Total Protein (mg) | PAL Activity (U/mL) | Total Activity (Units) | Specific Activity (U/mg) | Yield (%) | Purif. (Fold) |
| Crude Extract | 70 | 77.4 | 5415 | 13.62 | 953.6 | 0.176 | 100% | 1.00 |
| Heat Treatment | 43 | 52.0 | 2237 | 14.95 | 642.8 | 0.287 | 67% | 1.63 |
| Am. Sulf. PPT | 22.2 | 55.6 | 1235 | 54.7 | 1213.6 | 0.982 | 127% | 5.58 |
| Anion Exchange | 15.0 | 12.7 | 190.2 | 55.63 | 834.4 | 4.387 | 88% | 24.92 |
| HIC | 5.8 | 15.1 | 88 | 113.75 | 659.7 | 7.530 | 69% | 42.76 |
| Gel Filtration | 4.4 | 8.9 | 39 | 54.77 | 241.0 | 6.143 | 25% | 34.89 |
| GF Ends | 1.6 | 6.6 | 11 | 31.47 | 50.3 | 4.774 | 5% | 27.11 |

Example 6

Carbon Source Selection

This example describes the effect of various carbon sources on the ability of the recombinant *Saccharomyces cerevisiae* strain (PTA 408) containing the *Rhodosporidium toruloides* PAL gene (SEQ ID NO:7) plus the plant P-450 and the P-450 reductase (SEQ ID NO:11 and SEQ ID NO:13 respectively) to convert phenylalanine to PHCA.

Two colonies (#1 and #2) from the *Saccharomyces cerevisiae* containing the yeast PAL and the plant cytochrome P-450 and the cytochrome P-450 reductase were chosen and grown on three different media containing either raffinose, galactose or glucose. The media were identified as Raf/SCM or Gal/SCM or Glu/SCM. The formulation of various media used in these experiments is indicated below:

Glu/SCM (Ade/His/Ura) contained: Bacto-yeast nitrogen base (6.7 g/L); glucose, (20.0 g/L); and SCM, (2.0 g/L).

Raf/SCM (Ade/His/Ura) contained: Bacto-yeast nitrogen base, (6.7 g/L); raffinose, (20.0 g/L); and SCM, (2.0 g/L).

Raf/Gal SCM (Ade/His/Ura)/Tyr/Phe contained: Bacto-yeast nitrogen base, (6.7 g/L); raffinose, (10.0 g/L); galactose, (10.0 g/L); SCM, (2.0 g/L); tyrosine, (0.5 g/L); and phenylalanine, (10.0 g/L).

SCM (Ade/His/Ura) agar plate for yeast contained: Bacto-yeast nitrogen base, (3.35 g/L); dextrose, (10.0 g/L); agar, (10.0 g/L); SCM, (1.0 g/L); and ddH$_2$O, (500 mL).

Glycerol stocks (300 μL) of each of the colonies were used to inoculate the Glu/SCM, Gal/SCM and Raf/SCM media. Duplicate cultures were prepared with each strain and each medium and cultures were grown for 24 and 48 h.

The cell density was measured as described above and the cells were then centrifuged, washed once with 0.85% saline phosphate buffer, resuspended in the SCM medium (5.0 mL) and the OD$_{600}$ was measured again. The cells were then added to the corresponding flasks which contained either 25.0 mL of the Raf/SCM or the Gal/SCM medium to the final OD$_{600}$ of 0.5. Galactose (5% final concentration) was added to each flask and left on the shaker for about 16 h to allow for induction. Following induction, phenylalanine (1.0 mM final concentration) was added to each flask and samples (1.0 mL) were taken from each flask at 2, 4, 6, 24 and 48 h and analyzed by HPLC for the presence of PHCA (see Table 5).

TABLE 5

| Carbon Source | 2 h | 4 h | 6 h | 24 h | 48 h |
|---|---|---|---|---|---|
| Strain #1 PHCA Production (μM) after Addition of 1.0 mM Phenylalanine | | | | | |
| raffinose | 116.28 | 125.43 | 165.34 | 270.15 | 99.85 |
| galactose | 95.54 | 164.71 | 183.51 | 231.25 | 97.56 |
| glucose | 57.42 | 128.04 | 170.18 | 269.62 | 91.71 |
| Strain #2 PHCA Production (μM) after Addition of 1.0 mM Phenylalanine | | | | | |
| raffinose | 145.95 | 188.06 | 218.45 | 293.54 | 116.7 |
| galactose | 150.85 | 171.07 | 196.26 | 230.95 | 103.09 |
| glucose | 75.71 | 179.52 | 161.1 | 238.77 | 78.65 |

As is seen by the data in Table 5, both strains tested appeared to behave similarly when grown in different media. The highest level of production of PHCA was observed between 6–24 h and around 30% of the phenylalanine was converted to PHCA. Following the initial appearance and accumulation, a decrease in the concentration of the PHCA was observed (48 h).

Example 7

Production of PHCA by Recombinant Saccharomyces cerevisiae Strain Containing the Rhodosporidium toruloides PAL, the Plant Cytochrome P-450 and the Cytochrome P-450 Reductase This example describes induction by galactose for production of PHCA by a recombinant Saccharomyces cerevisiae strain that contains the wild type PAL plus the plant cytochrome P-450 and the cytochrome P-450 reductase genes.

Since PAL, the cytochrome P-450 and the cytochrome P-450 reductase that had been incorporated into the Saccharomyces cerevisiae strain, were under the control of the galactose promoter, experiments were performed in order to examine the effect of the length of induction by galactose on the level of PHCA formed. Saccharomyces cerevisiae strain #2, which had produced the highest level of PHCA, was chosen and induced by galactose. In order to examine if the recombinant Saccharomyces cerevisiae could directly convert glucose to PHCA, one set of cells, after one h induction with galactose, received glucose but no phenylalanine was added. Another set of cells was grown on raffinose. Samples were taken from all flasks at intervals and prepared for HPLC analysis as described above.

A sample of the glycerol suspension of Saccharomyces cerevisiae was streaked on an SCM-glucose plate and incubated at 30° C. Four colonies were picked from the plate, inoculated into 4.0 mL of Glu/SCM medium left on the shaker (30° C., 250 rpm) overnight. One mL of the cell suspension was taken and the OD$_{600}$ measured. After 24 h of growth, when the OD$_{600}$ was around 1.4 to 1.6, cells (1.0 mL) were transferred to 25 mL of Glu/SCM medium or 50 mL of Raf/SCM medium. Following overnight growth (30° C., 250 rpm) samples (1.0 mL) were taken from each flask and the OD$_{600}$ measured.

| | OD$_{600}$ |
|---|---|
| 1. #1 in Raf/SCM medium | 0.3775 |
| 2. #1 in Glu/SCM medium | 1.5119 |
| 3. #2 in Raf/SCM medium | 0.4730 |
| 4. #2 in Glu/SCM medium | 1.4923 |

As can be seen from the OD data, higher cell mass was obtained after growth on glucose compared to raffinose. In order to examine if the recombinant Saccharomyces cerevisiae could directly convert glucose to PHCA without additional phenylalanine an experiment was set up in which following growth on glucose or raffinose, cells were induced by galactose prior to glucose addition. Samples were taken at intervals and prepared for HPLC analysis as described above. Data is shown in Table 6.

TABLE 6

Effect of Growth on Glucose Versus Raffinose on PHCA Production by Saccharomyces cerevisiae Containing PAL + P-450 + P-450 Reductase (induced by galactose)

| Incubation Time | Induction 1.0 h | Induction 3.0 h | Induction 6.0 h |
|---|---|---|---|
| Recombinant Saccharomyces cerevisiae grown on glucose: PHCA production (μM) | | | |
| 2.0 h | 0.33 | 1.37 | 4.58 |
| 4.0 h | 0.57 | 2.62 | N/A |
| 6.0 h | 0.48 | 3.33 | N/A |
| 24 h | 0.98 | 7.63 | 14.59 |
| 48 h | 2.14 | 6.64 | 14.25 |
| Recombinant Saccharomyces cerevisiae grown on raffinose PHCA production (μM) | | | |
| 2.0 h | 7.11 | 30.72 | 62.73 |

TABLE 6-continued

Effect of Growth on Glucose Versus Raffinose on
PHCA Production by *Saccharomyces cerevisiae*
Containing PAL + P-450 + P-450 Reductase
(induced by galactose)

| Incubation Time | Induction 1.0 h | Induction 3.0 h | Induction 6.0 h |
| --- | --- | --- | --- |
| 4.0 h | 9.33 | 45.49 | N/A |
| 6.0 h | 12.55 | 55.88 | N/A |
| 24 h | 28.49 | 112.37 | 202.77 |
| 48 h | 38.63 | 110.85 | 193.63 |

As shown in the data in Table 6, while growth in the medium containing glucose produced higher cell mass, the amount of PHCA formed was much higher following growth in the presence of raffinose (approximately 200 μM PHCA within 24 h following growth in raffinose versus approximately 14.5 μM following growth in glucose). This underlines the inhibitory effect of glucose on the galactose inducible promoter.

In another experiment, the effect of addition of phenylalanine to the growth medium containing either glucose or raffinose was determined. Samples (10 mL) from each flask were transferred into a 125 mL capacity flask containing 25 mL of medium and cells were induced by galactose (2% final concentration). The induction was allowed for 1.0, 3.0, 6.0 h and overnight. After the specified induction time, phenylalanine (1.0 mM) was added to each flask and formation of PHCA was measured. Results are summarized in Table 7 below.

TABLE 7

Effect of Addition of Phenylalanine on PHCA Production by
*Saccharomyces cerevisiae* Containing PAL + P-450 + P-450 Reductase During
Growth on Glucose Versus Raffinose (induced by galactose)
PHCA Production (μM) after Addition of 1.0 mM Phenylalanine

| Induction Time | Carbon Source | 2.0 h | 4.0 h | 6.0 h | 24 h | 48 h | 54 h |
| --- | --- | --- | --- | --- | --- | --- | --- |
| 1.0 h | raffinose | 9.33 | 45.05 | 57.69 | 475.62 | 531.25 | 554.46 |
|  | glucose | 1.65 | 7.01 | 5.99 | 172.04 | 233.97 | 230.24 |
| 3.0 h | raffinose | 37.66 | 72.44 | 155.16 | 459.99 | 536.54 | 545.29 |
|  | glucose | 4.14 | 4.86 | 18.55 | 212.02 | 318.62 | 342.95 |
| 6.0 h | raffinose | 142.02 | N/A | N/A | 454.71 | 539.33 | 537.62 |
|  | glucose | 25.21 | N/A | N/A | 235.42 | 369.9 | 372.24 |
| overnight | raffinose | 11.56 | 208.11 | 260.46 | 497.97 | 424.28 | 408.32 |
|  | glucose | 9.87 | 10.13 | 36.74 | 354.15 | 424.89 | 398.81 |

As depicted in Table 7 and as expected, addition of phenylalanine to both cultures resulted in production of higher levels of PHCA compared to those produced in the absence of additional phenylalanine. Generally cells grown on raffinose produced higher amounts of PHCA from phenylalanine compared to those grown on glucose. The average level of PHCA produced from phenylalanine by cells growing on raffinose was around 500 μM and the highest level of PHCA was formed at around 24 h. In most cases, the level of PHCA reached a maximum at or around 24 h and remained without significant changes until the end of the experiment (approximately 54 h). Duration of induction (i.e., 1.0, 3.0, 6.0 h and overnight) did not seem to make a significant difference in the level of PHCA production. The level of PHCA formed in cultures growing on glucose was around 300 μM. While the total amount of PHCA formed by glucose-grown cells was less than that produced by cells grown on raffinose, the pattern of production of PHCA was similar.

In summary, the recombinant *Saccharomyces cerevisiae* cells containing the *Rhodosporidium toruloides* wild type PAL plus the plant cytochrome P-450 and the cytochrome P-450 reductase had the ability to convert glucose directly, in the absence of additional phenylalanine, to PHCA (approximately 25% conversion). When phenylalanine was added around 50% was converted to PHCA.

Example 8

Development of a Selection System for Identification of the Mutant PAL (PAL/TAL) Enzyme This example describes a method for selection of the mutant PAL enzyme with improved TAL activity. There are currently no engineered enzymes that can efficiently catalyze the conversion of tyrosine directly to PHCA with no intermediate step. In this reaction, the enzyme converts tyrosine to PHCA and ammonia while in the reverse reaction the same enzyme converts PHCA and ammonia to tyrosine. In order to detect mutant PAL enzymes able to convert tyrosine to PHCA, the following screen was developed. Constructing the Expression Vector (PCA12Km):

A weak expression vector was made by modifying the commercially available pBR322 vector. Briefly, pBR322 was digested with Pst I and subjected to 20 cycles of PCR with two primers, pBR1 (SEQ ID NO:3) 5'-GAGAGACTCGAGCCCGGGAGATCTCAGACCAA GTTTACTCATATA-3' and pBR2 (SEQ ID NO:4) 5'-GAGAGACTCGAGCTGCAGTCTAGAACTCTTTTT TCAATATTATTG-3'. The PCR reaction product was extracted with phenol chloroform, EtOH precipitated and digested with Xho I. The Xho I digested product was then gel isolated, ligated and transformed into *E. coli* selecting for tetracycline resistance. This vector is therefore a pBR322 lacking the ampicillin resistance gene but containing the beta-lactamase promoter and the following restriction sites: Xba I, Pst I, Xho I, Sma I, Bgl II. The tetracycline-resistance gene in pBR322 was replaced by the kanamycin-resistance gene. Tetracycline resistant gene was cut out of pCA12 (FIG. 1) at EcoR V (185) and Nru 1 (972) sites, the ends were polished by using pfu polymerase (PCR polishing kit, Stratagene) and ligated with the blunt-ended 9 kb kanamycin resistant gene fragment (Vieira and Messing, *Gene* 19:259–268 (1982)). Final construction was selected on the LB/km plates after transformation of the ligation in to the XL1-Blue vector (FIG. 1).

Subcloning the *Rhodosporidium toruloides* PAL Gene into PCA12Km:

The gene sequence of yeast (*Rhodosporidium toruloides*) PAL has been determined and published (Anson et al., *Gene* 58:189–199 (1987)). Based on the published sequence, the gene was subcloned into a pBR322-based vector. The entire PAL gene was then removed from the plasmid by XbaI-PstI digestion, and the gene was ligated into the XbaI-PstI-digested PCA12Km. The new construct containing the PAL gene was designated PCA18Km.

Expression of the PAL Enzyme in the Tyrosine-Auxotrophic *E. coli*:

The PCA12Km and PCA18Km were transformed into the tyrosine-auxotrophic *E. coli* strain AT2471 and the TAL and PAL activities were measured using the whole cell assay. Formation of small quantities of PHCA or cinnamic acid were detected following incubation of these cells with tyrosine or phenylalanine (Table 8).

TABLE 8

PHCA and Cinnamic Acid Formation from Tyrosine and Phenylalanine, Respectively*

|  | PHCA (µM) | cinnamic acid (µM) |
|---|---|---|
| Cells containing PCA12 Km | 0 | 0 |
| Cells containing PCA18 Km | 10.8 | 38 |

*The cells were incubated with 1.0 mM tyrosine or phenylalanine for 1.0 h, and the PHCA or cinnamic acid formation was detected by HPLC (see general methods).

As seen in Table 8, the yeast PAL enzyme was weakly expressed in the tyrosine-auxotrophic *E. coli* strain AT2471 containing the PCA18Km vector.

Determination of Selection Condition (Development of a Selection System):

The tyrosine-auxotrophic *E. coli* strain AT2471 containing pCA18Km showed the same tyrosine-auxotrophic property as the original strain. The cells did not grow on the minimal plate, but grew well when 0.004 mM tyrosine was added to the plate. In order to find the suitable condition for selection, cell growth was tested on a minimal plate containing various concentrations of tyrosine or PHCA (see Table 9).

TABLE 9

Tyrosine-Auxotrophic *E. coli* Cell Growth Under Various Concentrations of Tyrosine or PHCA

|  | Tyrosine* | PHCA** |
|---|---|---|
| 0.0001–0.0002 mM | − | +++ |
| 0.0003–0.0005 mM | + | +++ |
| 0.001–0.004 mM | +++ | +++ |
| 1.0–2.0 mM |  | ++ |
| 4.0–6.0 mM |  | + |
| 10 mM |  | − |

*No PHCA was added in the growth medium for testing the tyrosine-auxotrophic property.
**0.004 mM tyrosine was added in the growth medium for testing the toxicity of PHCA.
−: no growth;
+: very poor growth;
++: poor growth;
+++: good growth.

The results shown in Table 9 indicate that high concentrations of PHCA are toxic to the cells. The 2.0 mM PHCA concentration was chosen for the selection experiment. The information about the cell growth at different tyrosine concentrations is important for the selection. For example, when the tyrosine made from PHCA by the cell is not enough to support cell growth, small amounts of tyrosine (0.0001–0.0002 mM) can be added to the plate. This will allow identification of strains expressing the enzyme with slightly improved TAL activity. In other words, the selection stringency can be modulated by changing the concentration of PHCA and tyrosine in the selection plate.

Example 9

Engineering the Mutant PAL Enzyme with Improved TAL Activity Error-Prone PCR

The following primers were used for amplifying the entire PAL gene from PCA18Km construct:

Primer A (SEQ ID NO:5):
  5'-TAGCTCTAGAATGGCACCCTCG-3'
Primer B (SEQ ID NO:6):
  5'-AACTGCAGCTAAGCGAGCATC-3'.

The primer A (forward primer) contained a Xba I restriction enzyme site just before the ATG codon, and primer B (reverse primer) had a Pst I site just after the stop codon. To increase the rate of the PCR error, plain Taq polymerase and more reaction cycles (35 cycles) were used. In addition, the ratio of dATP, dTTP, dGTP and dCTP was changed. Four different reactions were performed. In each reaction, the concentration of one of the dNTP's was 0.1 mM, and the other three dNTP were adjusted to 0.4 mM. The PCR products from four reactions were mixed together following completion of the reaction. After digestion of the error-prone PCR products with Xba I and Pst I, fragments were ligated into the XbaI-PstI-digested PCA12Km.

In vivo Mutagenesis Using *E. coli* XL1-Red Strain:

The PCA18Km was transformed into the XL1-Red strain, and the cells were grown overnight in the LB medium plus kanamycin. To increase the mutation rate, the cells were diluted with fresh growth medium, and grown further. After 2–4 cell generation cycles, the plasmids were purified, and used for selection.

Selection:

After mutagenesis, the pool of mutated PCA18Km containing the randomly mutated PAL gene were transformed into the tyrosine-auxotrophic *E. coli* strain by electroporation. The transformation efficiency was $1.5 \times 10^8$ cfu/µg DNA. The cells were then incubated in the LB medium with antibiotics for more than 5.0 h. After washing with the minimal medium, the cells were streaked on plates containing the minimal medium supplemented with 0.0002 mM tyrosine and 2.0 mM PHCA. After 3.0–5.0 days of incubation at 30° C., 1.0–10 colonies appeared on each plate.

The colonies that had appeared on the selection plates were analyzed for their PAL/TAL activity using the whole cell assay described in the general methods. One of the mutants, designated EP18Km-6, showed an enhanced TAL activity ratio than the wild type cell. Genetic analysis for the EP18Km-6 mutant was carried out. The plasmid DNA was purified from the mutant cells, and then re-transformed into *E. coli*. The new transformant showed the same enhanced TAL ratio as the original mutant, indicating that all mutations that involved improvement of TAL activity were on the plasmid. To better characterize the mutants, the following analyses were carried out.

Example 10

Characterization of the Mutant PAL Enzyme

Sequence Analysis of the Mutant Gene:

The entire gene of EP18Km-6 was sequenced on an ABI 377 automated sequencer (Applied Biosystems, Foster City, Calif.), and the data managed using DNAstar program (DNASTAR Inc., Madison, Wis.). Analysis of the resulting PAL mutants followed by comparison with the wild type gene (SEQ ID NO:7), indicated that the mutant gene (SEQ ID NO:9) contained the following four single base substitution mutations (point mutations): CTG (Leu215) to CTC, GAA (Glu264) to GAG, GCT (Ala286) to GCA and ATC (Ile540) to ACC. The first three mutations were at the third base, generating silent mutations which did not result in any amino acid change. The fourth mutation was a second base change (ATC to ACC). This mutation changed the isoleucine-540, which is in the conserved region of the enzyme, to a threonine. Various PAL enzymes from different sources have either isoleucine or leucine at this critical position.

Figure 2:
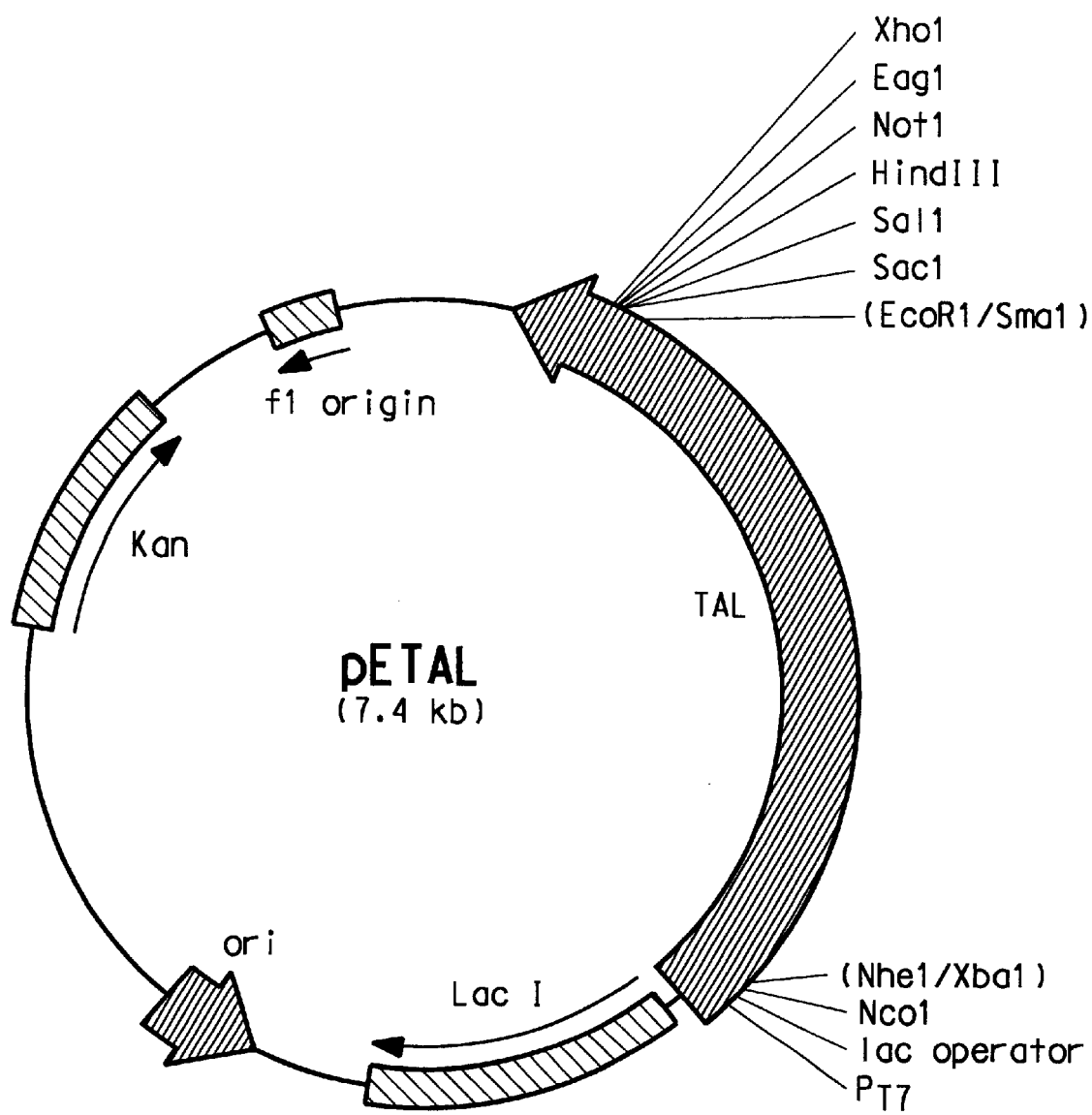
FIG. 2 is a plasmid map of the vector pETAL containing the mutal PAL/TAL enzyme.
Figure 3:
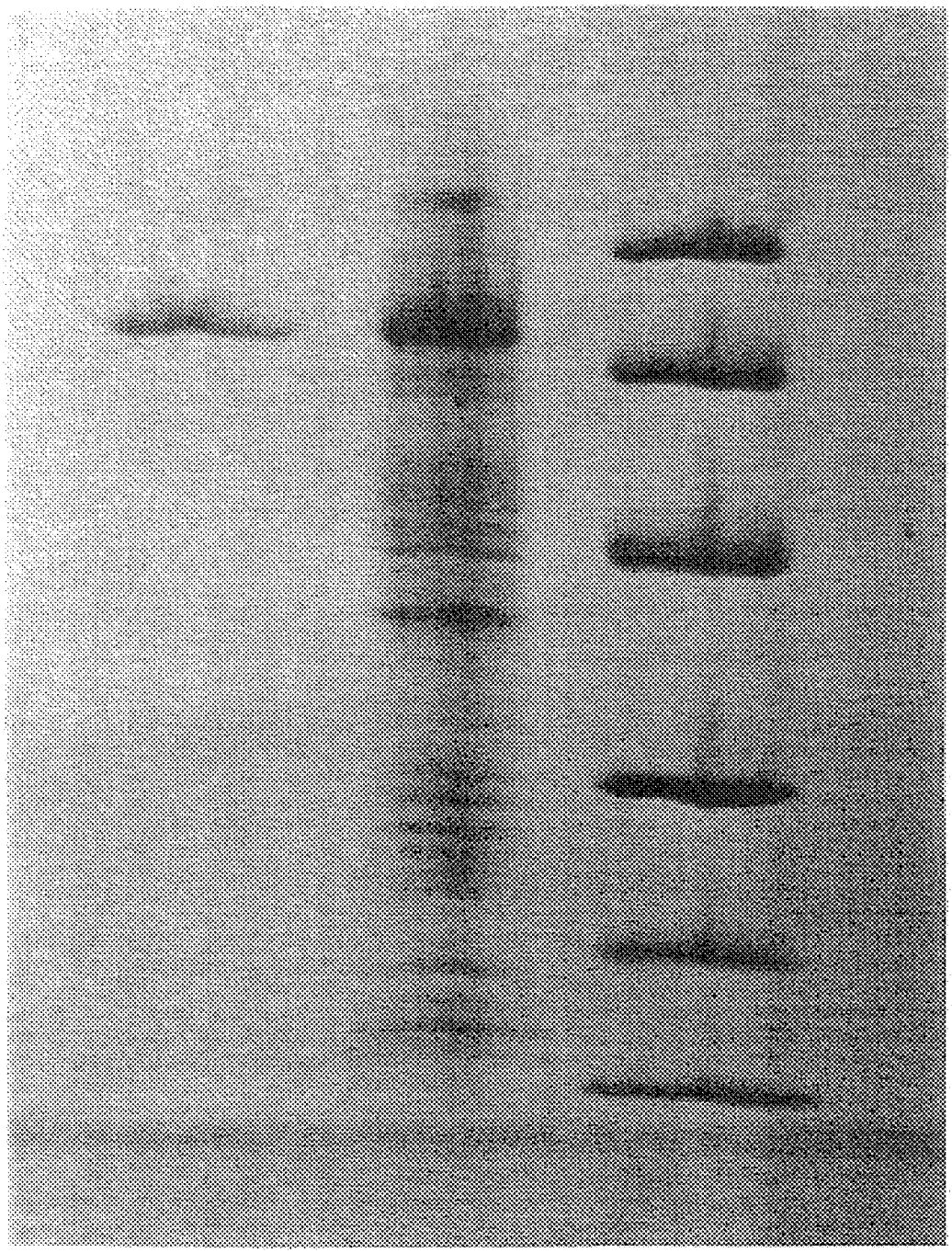
FIG. 3 shows the SDS-PAGE of purified mutant PAL enzyme and the cell crude extracts used as the starting materials for purification of the mutant PAL enzyme.

Over-Expression and Purification of EP18Km-6 Mutant Enzyme:

In order to obtain sufficient quantities of the pure enzyme for enzymatic kinetics analysis, the enzyme was expressed in the over-expression vector, pET-24-d. The pET-24-d vector was digested with EcoRI, and the digestion product was filled-in using the Klenow enzyme (Promega, Madison, Wis.) according to the manufacturer's instructions. The linearized vector was then digested with NheI and the mutant PAL gene was obtained by cutting the EP18Km-6 with XbaI and SmaI. Since the NheI and XbaI are compatible sites, the mutant gene was subcloned into the pET24-d vector by ligation in order to prepare the pETAL construct (FIG. 2). Although the pET-24-d vector carries an N-terminal T7 Tag sequence plus an optional C-terminal HisTag sequence, these Tags were not used so that the enzymes could be expressed with natural sequences at both N- and C-termini. After cloning the mutant gene into the pET-24-d vector, the construct was transformed into *E. coli* BL21(DE3). For over-expression, the cells were grown in the LB medium containing kanamycin to an $OD_{600}$ of 1.0 before 1.0 mM IPTG was added. After 4.0 h of induction, cells were harvested by centrifugation and the crude extracts prepared as described in the General Methods section. The SDS-PAGE analysis of the crude extracts revealed that the expressed enzyme was the dominant protein band, and the expression level was estimated to be 10–15% of total protein (FIG. 3). FIG. 3 shows the SDS-PAGE of purified mutant PAL enzyme (lane A) and the cell crude extracts (lane B) which has been used as the starting materials for purification. Lane C is the standard marker of molecular weight (94, 67, 43, 30, 20 and 14 kDa from top to bottom). For purification of PAL, the cell pellet was suspended in 10 mM potassium phosphate buffer, pH 6.6, containing protease inhibitors PMSF, amino caproic acid and benzamidine (1.0 mM, each). The cells were broken by sonication (Branson model 185, 70% power setting, 4 min in ice bath), followed by centrifugation (30,000×g, 30 min). The clear supernatant was applied to a Mono-Q HPLC column (flow rate of 1.0 mL/min). The column was started using a 50 mM potassium phosphate buffer, pH 7.0, followed by a 400 mM potassium phosphate buffer, pH 7.2 as the elution buffer. The enzyme was eluted at a concentration of approximately 90 mM potassium phosphate. The active fractions were pooled and concentrated using Centricon YM100 (Milipore, Bedford, Mass.). The enzyme was >98% pure as judged by the SDS-PAGE electrophoresis (FIG. 3).

Biochemical Characterization of Mutant PAL Enzyme:

A detailed enzyme kinetics analysis using the yeast wild type and the purified mutant PAL enzyme and tyrosine or phenylalanine as substrate, was carried out. The PAL and TAL activities were measured spectrophotometrically as described in the General Methods and the $K_M$ and $V_{max}$ were determined from its Lineweaver-Burke plot. The $k_{cat}$ was calculated from $V_{max}$ assuming the presence of four active sites in the active tetramer. The determined $K_M$ and $k_{cat}$ of the enzymes are shown in Table 10.

TABLE 10

$K_M$ and $k_{cat}$ of wild type and mutant PAL

| Enzyme | $K_M$ (mM) | $k_{cat}$ (sec$^{-1}$) |
|---|---|---|
| WT (Phe)* | 0.250 | 2.09 |
| WT (Tyr)** | 0.111 | 0.46 |
| Mutant (Phe)* | 0.333 | 2.45 |
| Mutant (Tyr)** | 0.05 | 0.63 |

*Phenylalanine was used as substrate.
**Tyrosine was used as substrate.

The catalytic efficiency, defined as $k_{cat}/K_M$, was calculated for both the wild type and mutant enzyme. The ratio of the TAL catalytic efficiency versus the PAL of the wild type enzyme was 0.5 while that of the mutant enzymes had increased to 1.7 (see Table 11). The results showed that unlike the wild type PAL enzyme which preferred to use phenylalanine, the mutant enzyme preferred to use tyrosine as substrate thereby clearly demonstrating that the substrate specificity of the yeast PAL enzyme had changed after mutagenesis and selection.

TABLE 11

Catalytic Efficiency[1] and TAL/PAL Ratio Comparison Between Wild Type and Mutant PAL

| Enzyme | PAL($k_{cat}/K_M$), M$^{-1}$ sec$^{-1}$* | TAL($k_{cat}/K_M$), M$^{-1}$ sec$^{-1}$** | TAL/PAL ratio |
|---|---|---|---|
| Wild type | 8.36 × 10$^3$ | 4.14 × 10$^3$ | 0.5 |
| Mutant | 7.36 × 10$^3$ | 12.61 × 10$^3$ | 1.7 |

*Phenylalanine was used as substrate
**Tyrosine was used as substrate
[1]catalytic efficiency is defined as $k_{cat}/K_M$

Example 11

Bioproduction of PHCA from Glucose in *E coli* through the TAL Route

Production of PHCA from Glucose in *E. coli* Using the Mutant PAL:

The plasmid with the mutant PAL gene, with improved TAL activity (EP18Km-6), was transformed into the wild type *E. coli* W3110. The cells were then grown in the minimal medium using glucose as the sole carbon source. After overnight growth, 20 μL of the growth medium was filtered, and analyzed by HPLC for detection of PHCA. No PHCA accumulation was found in the wild type (control) *E. coli* cells. However, when the mutant PAL gene was expressed in *E. coli*, 0.138 mM PHCA was detected in the overnight growth of the cells in a minimal medium containing glucose as the sole carbon source (see Table 12).

TABLE 12

PHCA Production from Glucose in E. coli cells With and Without Mutant PAL/TAL Enzyme Expressed

|  | PHCA (μM) | Cinnamic acid (μM) |
|---|---|---|
| Wild type E. coli | 0 | 0 |
| E. coli with mutant PAL expressed | 135 | 90 |

The E. coli Cells Lack Cinnamate Hydroxylase Activity:

An overnight incubation of the E. coli cells, containing the PCA12Km vector, with 1.0 mM cinnamic acid did not result in PHCA production underscoring the lack of ability of the E. coli cells to convert cinnamic acid to PHCA.

Example 12

Incorporation of the Modified PAL into the Yeast Expression Vector

The following yeast strains and the pGPD316 expression vector were used. Strain ZXY34-1A contained the genotype: Mata, ade2-1, can1–100, his3–11, -15, leu2–3, -112, trup1—1, ura3-1, aro 3:: ΔURA3, aro4:: ΔHIS3 and was designated an aro3, aro4 double knockout. Strain ZXY0304A contained the genotype: Mata, ade2-1, can1–100, his3–11, -15, leu2–3, -112, trup1-1, ura3-1, aro 3:: Δura3, aro4:: ΔHIS3 was an aro3, aro4 double knockout.

Figure 4:
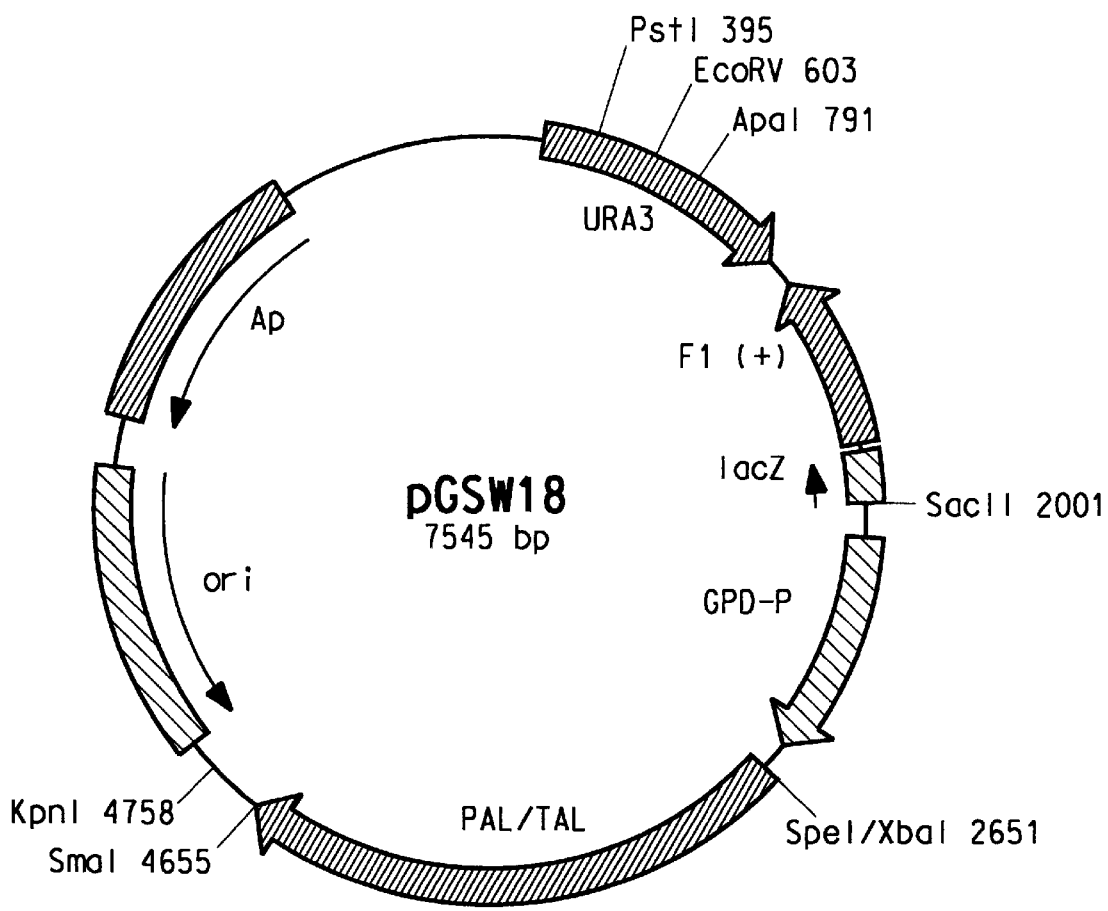
FIG. 4 is a plasmid map of the expression vector pGSW18 used for the expression of the mutant PAL/TAL enzyme in yeast.

Using standard sub-cloning methods well known in the art, the modified PAL was incorporated into the above vectors. The modified PAL cDNA (2.0 kb) was cut by XbaI and SmaI restriction enzymes and the cut fragment obtained ligated into the expression vector pGPD316 which had been cut by SpeI and SmaI restriction enzymes. The new construct from pGPD316 plus insert from pEp18 was designated pGSW18 (FIG. 4). The new construct were verified by restriction enzyme digestion followed by agarose gel electrophoresis.

Example 13

The Ability of ARO4GSW to Convert Glucose to PHCA in the Absence of Aromatic Amino Acids Strain ZXY0304A contained the genotype: Mata, ade2-1, can1-100, his3–11, -15, leu2–3, -112, trup1–1, ura3-1, aro 3:: Δura3, aro4:: ΔHIS3, designated as an aro3, aro4 double knockout was used. The ZXY0304A strain was transformed by pGSW18 containing the modified PAL with the standard lithium acetate method. The transformants, ARO4GSW, were selected using the SCM medium (without leucine and uracil). ARO4GSW (100 μL glycerol stock) was used to inoculate the regular SCM medium containing 2% glucose. The organisms were grown at 30° C. for 5.0 h, cells were centrifuged, resuspended in the SCM medium containing 2% glucose but without aromatic amino acids and allowed to grow overnight. The cells were then centrifuged and resuspended in the following media to a final cell density of 1.0 ($OD_{600}$ nm): a) regular SCM medium containing about 400 μm of phenylalanine and tyrosine and b) SCM medium without aromatic amino acids. The cells were left on the shaker (250 rpm, 0° C.) and samples (1.0 mL) were taken for HPLC analysis at 2.0, 4.0, 6.0 and 16 h. The results are shown in Table 13.

TABLE 13

Effect of Aromatic Amino Acids on PHCA Production of ARO4GSW Yeast Strain PHCA production (μM)

|  | 2.0 h | 4.0 h | 6.0 h | 16 h |
|---|---|---|---|---|
| no aromatic AA* | 1.157 | 2.187 | 2.866 | 5.813 |
| aromatic AA | 3.806 | 6.316 | 10.313 | 15.147 |

*AA = amino acid

As shown in Table 13, the recombinant yeast strain ARO4GSW produced PHCA from glucose in the absence of any additional aromatic amino acids in the growth medium. The data also demonstrate that addition of aromatic amino acids to the growth medium results in almost a 2.5 fold increase in the level of PHCA produced compared to growth in the absence of aromatic amino acids. These results underscore the ability of the recombinant Saccharomyces cerevisiae containing the mutated PAL, in the absence of the cytochrome P-450 and the cytochrome P-450 reductase, to convert glucose to PHCA.

Example 14

Effect of Phenylalanine and Tyrosine on PHCA Production by ARO4GSW Containing the Modified PAL During Aromatic Amino Acid Starvation This Example investigates the effects of phenylalanine and tyrosine on PHCA production by the recombinant yeast strain ARO4GSW containing the modified PAL during aromatic amino acid starvation.

A sample (100 μL) of glycerol stock of ARO4GSW was inoculated into the regular SCM medium containing 2% glucose. The cells were left on the shaker at 30° C. for 5.0 h before they were harvested. The pellet was resuspended in the SCM medium containing 2% glucose but without aromatic amino acids and grown overnight at 30° C. on a shaker. The cultures were then centrifuged and resuspended in the following media with final cell density of 1.0 $OD_{600}$ nm: a) regular SCM medium, b) SCM medium containing no aromatic amino acids, 2% glucose and 1.0 mM phenylalanine and c) SCM medium containing no aromatic amino acid, 2% glucose and 1.0 mM tyrosine. These cultures were returned to the shaker (250 rpm, 30° C.) and samples (1.0 mL) were taken for HPLC analysis after 2.0, 4.0, 6.0 and 16 h. Results are shown in Table 14.

TABLE 14

Effect of Aromatic Amino Acids on PHCA Production of ARO4GSW Yeast Strain PHCA production (μM)

|  | 2.0 h | 4.0 h | 6.0 h | o/n |
|---|---|---|---|---|
| no aromatic aa | 0 | 0.609 | 0.806 | 1.327 |
| Phe | 0 | 0.872 | 1.147 | 1.735 |
| Tyr | 1.141 | 1.563 | 2.433 | 4.272 |

As is seen by the data in Table 14, when cells were starved for aromatic amino acids, no significant PHCA was produced. Addition of phenylalanine did not have any significant effect on the level of PHCA produced. However, addition of tyrosine, resulted in significant increase in the level of PHCA. The results therefore confirm that the novel recombinant strain containing the modified PAL gene developed in this invention preferred tyrosine as the substrate for PHCA production.

Example 15

Transformation and Expression of Mutant PAL/TAL in Maize and Production of PHCA A chimeric gene comprising the mutant PAL/TAL gene (SEQ ID NO:8) in sense orientation can be constructed by polymerase chain reaction (PCR) of the gene using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a 100 μL volume in a standard PCR mix consisting of 0.4 mM of each oligonucleotide and 0.3 μM of target DNA in 10 mM Tris-HCl, pH 8.3, 50 mM KCl, 1.5 mM $MgCl_2$, 200 mM dGTP, 200 mM dATP, 200 mM dTTP, 200 mM dCTP and 0.025 unit DNA polymerase. Reactions are carried out in a Perkin-Elmer Cetus Thermocycler™ for 30 cycles comprising 1 min at 95° C., 2 min at 55° C. and 3 min at 72° C., with a final 7 min extension at 72° C. after the last cycle. The amplified DNA is then digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty with the ATCC and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega Corp., 7113 Benhart Dr., Raleigh, N.C.). Vector and insert DNA can be ligated at 15° C. overnight, essentially as described (Maniatis). The ligated DNA may then be used to transform *E. coli* XL1-Blue (*Epicurian Coli* XL-1; Stratagene). Bacterial transformants can be screened by restriction enzyme digestion of plasmid DNA and limited nucleotide sequence analysis using the dideoxy chain termination method (DNA Sequencing Kit, U.S. Biochemical). The resulting plasmid construct would comprise a chimeric gene encoding, in the 5' to 3' direction, the maize 27 kD zein promoter, a DNA fragment encoding the mutant PAL/TAL enzyme, and the 10 kD zein 3' region.

The chimeric gene so constructed can then be introduced into corn cells by the following procedure. Immature corn embryos can be dissected from developing caryopses derived from crosses of the inbred corn lines H99 and LH132 (Indiana Agric. Exp. Station, Ind., USA). The embryos are isolated 10 to 11 days after pollination when they are 1.0 to 1.5 mm long. The embryos are then placed with the axis-side facing down and in contact with agarose-solidified N6 medium (Chu et al., *Sci. Sin.* Peking 18:659–668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks. The plasmid, p35S/Ac (obtained from Dr. Peter Eckes, Hoechst Ag, v Frankfurt, Germany), may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al., *Nature* 313:810–812 (1985)) and the 3M region of the nopaline synthase gene from the T-DNA of the Ti plasmid of *Agrobacterium tumefaciens*. The particle bombardment method (Klein et al., *Nature* 327:70–73 (1987)) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 min, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a flying disc (Bio-Rad Labs, 861 Ridgeview Dr, Medina, Ohio). The particles are then accelerated into the corn tissue with a PDS-1000/He (Bio-Rad Labs, 861 Ridgeview Dr., Medina, Ohio), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks, the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium. Plants can be regenerated from the transgenic callus by first transferring clusters of tissue to N6 medium supplemented with 0.2 mg per liter of 2,4-D. After two weeks, the tissue can be transferred to regeneration medium (Fromm et al., *Bio/Technology* 8:833–839 (1990)).

Levels of PHCA production is expected to range from about 0.1% to about 10% dry weight of the plant tissue.

Example 16

Selection for an Improved TAL Enzyme Using L-Tyrosine As a Sole Carbon Source The mutagenized TAL gene (SEQ ID NO:8) is introduced into an Acinetobacter chromosome by natural transformation, essentially as described by Kok et al., (*Appl. Environ. Microbiol.* 65:1675–1680 (1999)), incorporated herein by reference. The TAL gene is inserted in the host in a vector under the control a constitutive promoter and in the presence of an antibiotic resistance marker gene. Transformants are cultured on an M9 salt media (Example 4) containing 15 g agar, 6 g $Na_2HPO_4$, 3 g $KH_2PO_4$, 0.5 g NaCl, 1 g $NH_4Cl$, 0.5 g L-tyrosine, 2 ml 1 M $MgSO_4$, 0.1 ml 1 M CaCl$_2$ in 1 L distilled water (pH 7.4). Transformants are isolated on the basis of antibiotic resistance. Transformants containing an evolved TAL gene that improves the conversion of L-tyrosine to PHCA show better growth on minimal media containing L-tyrosine and form larger colonies. These larger colonies are recovered for additional rounds of evolution until the desired level of TAL activity is achieved.

Example 17

Cloning of Mutant PAL (EP18Km-6) Gene into pET17b Vector

All N-terminal and C-terminal truncation mutants were made in vector pET17b. As a positive control, the mutant PAL (EP18Km-6) gene was first cloned into vector pET17b. This construct was named pET17b-Km6, and is also used as a positive control for regional mutagenesis experimentation (see Examples 21 and 22).
Preparation of NheI/Filled-in pET17b Vector and XbaI/SmaI-Digested Mutant PAL Gene:

10 μL of pET17b plasmid DNA (500 ng/μL) was digested at 37 C. for 1 hr in 4 μL of 10× Promega restriction enzyme reaction buffer E (Promega, Madison, Wis.), 2 μL of BamHI and 34 μL of distilled deionized water. After digestion, the sample was loaded onto a 1% agarose gel, and the linearized vector was gel purified using Qiagen's gel extraction kit (Qiagen Inc., Valencia, Calif.) according to manufacturer's instructions. The DNA was eluted in 50 μL of EB buffer. The linearized vector was filled-in using 1 μL of Promega Klenow enzyme, 1 μL of 2 mM dNTPs and 12 μL of 5× Klenow buffer. After incubation at 37 C for 20 min, the DNA was precipitated by ethanol and then suspended in 20 μL of EB buffer. The filled-in vector was digested by using 3 μL of 10× Promega restriction enzyme reaction buffer B, 1 μL of NheI and 6 μL of distilled deionized water. After incubation at 37 C. for 30 min, the reaction mixtures were heated at 65 C. for 20 min to inactivate the enzyme. The DNA was precipitated by ethanol again, and resuspended in 50 μL of EB buffer.

To obtain XbaI/SmaI-digested mutant PAL gene, 20 μL of EP18Km-6 plasmid DNA (200 ng/μL) was digested in 5 μL of 10× multibuffer, 2 μL of XbaI, 2 μL of SmaI and 21 μL of distilled deionized water. The digestion mixture was incubated at 25 C. for 1 hr, and then at 37 C. for another 1 hr. After digestion, the reaction mixture was loaded onto a 1% agarose gel, the mutant PAL gene (2.15 kb) was purified with a Promega PCR clean-up kit, and the DNA sample was resuspended in 70 μL of EB buffer.
Cloning Mutant PAL Gene into pET17b:

Since NheI and XbaI are compatible sites, the mutant PAL gene was ligated into the pET17b vector in a ligation mixture containing 6 μL of XbaI/SmaI-digested mutant PAL gene, 2 μL of NheI/filled-in pET17b, 1 μL of 10× ligation buffer and 1 μL of T4 ligase (3 U/μL). The ligation mixture was incubated at 15 C. for 3 hrs, and then transformed into competent BL21(DE3) E. coli cells (Novagen, Madison, Wis.). Briefly, competent cells were thawed on ice for approximately 20 min. Then, 3.3 μL of the ligation mixture was added to 20 μL of the cells and set on ice for 20 min. Cells were heat shocked for 45 sec at 42 C. and put back on ice. After addition of 0.5 mL of SOC medium, the cells were incubated for 1 hr at 37 C. on a shaker. The cells were plated onto LB plates in the presence of ampicillin and incubated overnight at 37 C. Several colonies were picked for plasmid preparation. The entire insert was sequenced on an ABI377 automated sequencer (Applied Biosystem, Foster City, Calif.), and the data managed using DNAstar program (DNASTAR Inc., Madison, Wis.). Sequencing results showed that no mutations were introduced during subcloning.
Whole Cell TAL/PAL Activity Assay:

The following assay was performed to confirm that fully active mutant PAL enzyme was produced in BL21(DE3) E. coli cells. E. coli cells were grown in LB medium overnight. One mL of cell culture was pelleted and resuspended in 1 mL of 50 mM Tris-HCl buffer (pH 8.5) containing 0.5 mM tyrosine (for TAL activity measurement) or phenylalanine (for PAL activity measurement). The reaction mixture was incubated on the shaker at 37 C. for 1 hr. The reaction mixture was filtrated using 0.2 μm pore size filter (Millipore, Bedford, Mass.), and injected into HPLC (Hewlett-Packard Company, Palo Alto, Calif.). TAL or PAL activity was determined by measuring the concentration of the resulting PHCA or cinnamate. Results indicated that the mutant PAL gene was fully active in BL21(DE3) E. coli cells.

Example 18

Investigating the Role of the N-Terminus for TAL Activity in Mutant PAL (EP18Km-6) Gene by Making Truncation Mutants This Example describes the methods used to make a series of N-terminus truncated mutant PAL enzymes, to investigate the role of the N-terminus for TAL activity.
Making Truncated Mutant PAL Gene Fragments by PCR:

The following forward primers were used for making truncated mutant PAL gene fragments by PCR:

18NT-15 (SEQ ID NO:15):
  5'-GGCACTGCTAGCGACTCGATCTCGCAC-3'
18NT-30 (SEQ ID NO:16):
  5'-GGCACTGCTAGCTCGTTCGCAAACGGC-3'
18NT-45 (SEQ ID NO:17):
  5'-GGCACTGCTAGCGTCGCATCCGCAAAG-3'
18NT-60 (SEQ ID NO:18):
  5'-GGCACTGCTAGCCAGGCTGTCAATGGC-3'
18NT-90 (SEQ ID NO:19):
  5'-GGCACTGCTAGCGCAGTCGCAGGCTCG-3'
18NT-120 (SEQ ID NO:20):
  5'-GGCACTGCTAGCCAGGTCACGCAGGTC-3'
18NT-150 (SEQ ID NO:21):
  5'-GGCACTGCTAGCATGCTCGCCGCGCCGACC-3'
18NT-390 (SEQ ID NO:22):
  5'-GGCACTGCTAGCCAGAAGGCTCTCCTCGAG-3'

The number after 18NT indicates the number of base pairs truncated by the primer. For example, 18NT-15 was used to truncate the first 15 base pairs (first 5 amino acids) at the N-terminus, and 18NT-30 truncated the first 30 base pairs (first 10 amino acids), and so on. All of the primers contain a NheI (GCTAGC) restriction enzyme site for cloning.

The following reverse primer, which contains an EcoRI restriction enzyme site just after the stop codon, was used for PCR for all N-terminal truncation experiments:

EP9 (SEQ ID NO:23):
  5'-GCAGAATTCGGTACCCTAAGCGAGCATCTTGAG-3'

50 μL PCR reactions containing 5 μL of 2 mM dNTPs, 3 μL of 1 pmol/μL forward primer, 3 μL of 1 pmol/μL reverse primer, 1 μL of 30 ng/μL EP18Km-6 plasmid DNA as template, 0.5 μL HotStart Taq polymerase (Promega), and 33 μL of distilled deionized water were set up for each truncation experiment. PCR was carried out for 25 cycles with a 95 C. hot start for 10 min, a 94 C. melting temperature for 30 sec, a 55 C annealing temperature for 30 sec and 72 C. elongation temperature for 2 min.

Cloning PCR Fragments into pET17b Vector:

After PCR, the reaction mixtures were loaded onto a 1% agarose gel, and the PCR fragments were gel purified using a Qiagen gel extraction kit according to the manufacturer's instructions. PCR fragments were digested in 10× multibuffer (6 μL), NheI (2 μL), EcoRI (2 μL) and PCR product (50 μL). After incubation at 37 C. for 4 hrs, the reaction mixtures were heated at 65 C. for 20 min to inactivate the enzymes. The DNA fragments were further purified using Promega's PCR clean-up kit according the manufacturer's instructions. To prepare linearized vector, 60 μL of pET17b plasmid DNA was digested at 37 C. overnight in 10 μL of 10× multibuffer, 3 μL of NheI, 3 μL of EcoRI and 24 μL of distilled deionized water. After heat inactivation, the sample was loaded onto a 1% agarose gel, and the linearized vector was gel purified using Promega DNA clean-up kit.

The truncated mutant PAL gene fragments were then ligated into linearized pET17b vector in a ligation reaction containing 6 μL of NheI/EcoRI-digested PCR fragment (20 ng/μL), 2 μL of linearized pET17b (20 ng/μL), 1 μL of 10× ligation buffer and 1 μL of T4 ligase (3 U/μL). The ligation mixture was incubated at 15 C. overnight, and then transformed into BL21(DE3) E. coli cells, as described in Example 17. Several colonies were picked for each experiment, and the truncation constructs were confirmed by PCR and DNA sequence analysis.

Characterizing the Truncation Mutants:

The truncation mutants were analyzed by measuring TAL activity using the whole cell assay described in Example 17. Table 15 summarizes the results:

TABLE 15

Measurement of TAL activity in truncation mutants

| Strain | TAL Activity (%) |
|---|---|
| pET17b-Km6 | 100 |
| 5 a.a.* truncation | 100 |
| 10 a.a. truncation | 100 |
| 15 a.a. truncation | 100 |
| 20 a.a. truncation | 100 |
| 30 a.a. truncation | 95 |
| 40 a.a. truncation | 45 |
| 50 a.a. truncation | 0 |
| 130 a.a. truncation | 0 |

*a.a.: amino acid.

The results suggested that enzyme activity starts to decrease when more than 30–35 amino acids are truncated. Therefore, the N-terminus starting from amino acid No. 30 is important for TAL activity in the mutant PAL enzyme.

Example 19

Investigating the Role of the C-Terminus for TAL Activity in Mutant PAL (EP18Km-6) Gene by Making A Truncation Mutant This Example describes the method used to make a C-terminal truncation mutant PAL enzyme, to investigate the role of the C-terminus for TAL activity. Eighteen amino acids were removed from the mutant protein.

Preparation of C-Terminal Truncation Mutant PAL Gene Fragment:

A Bgl II restriction enzyme site is a unique cleavage site for mutant PAL; it cuts at base pair No. 2090, resulting in truncation of the last 18 C-terminal amino acids. To prepare the truncation gene fragment using this site, 20 μL of EP18Km-6 plasmid DNA (200 ng/μL) was digested at 37 C. for 1 hr in 4 μL of 10× multibuffer, 1 μL of XbaI, 1 μL of EcoRI and 14 μL of distilled deionized water. After digestion, the reaction mixture was loaded onto a 1% agarose gel, and the truncated gene fragment (2.1 kb) was purified using Promega PCR clean-up kit. The DNA sample was resuspended in 70 μL of EB buffer.

Cloning the Truncated Mutant PAL into pET17b:

First, the linearized pET17b vector was prepared. Digestion of the vector was achieved by using 4 μL of 10× multibuffer, 1 μL of NheI, 1 μL of BamHI and 10 μL of plasmid DNA (600 ng/μL). After incubation at 37 C for 1 hr, the sample was loaded onto a 1% agarose gel, and the linearized vector was gel purified using Promega DNA clean-up kit. Finally, the linearized pET17b vector was suspended in 70 μL of EB buffer.

The truncated mutant PAL gene fragment was ligated into linearized pET17b vector in a ligation mixture containing 8 μL of XbaI/BglII-digested truncation gene fragment, 0.5 μL of linearized pET17b, 1 μL of 10× ligation buffer and 1 μL of T4 ligase (3 U/μL). The ligation mixture were incubated at 15 C. for overnight, and then transformed into BL21 (DE3) E. coli cells, as described in Example 17. Several colonies were picked for each experiment, and the truncation constructs were confirmed by DNA sequence analysis using an ABI377 automated sequencer.

Measuring the TAL Activity of C-Terminal Truncation Mutant:

The C-terminal truncation mutant was analyzed by measuring TAL and PAL activities using the whole cell assay described in Example 17, and pET17b-Km-6 was used as positive control. Table 16 summarizes the results:

TABLE 16

Measurement of TAL activity in C-terminal truncation mutant

| Strain TAL Activity | (%) |
|---|---|
| pET17b-Km6 | 100 |
| C-terminal truncation mutant | 0 |

The results demonstrated that the TAL activity of mutant PAL enzyme was completely inactivated by truncation of the last 18 amino acids of the C-terminus, indicating the importance of this region for enzyme activity in mutant PAL.

Example 20

Development of a High Throughput Screening Assay for Identification of the Mutant PAL Enzyme with Altered TAL/PAL Ratio This example describes a novel method for screening the mutant PAL enzyme with altered TAL/PAL activities. This method can directly measure the TAL/PAL ratio using whole cells in high throughput fashion. It can be used for screening of mutants with improved TAL or PAL activity.

To perform the assay, E. coli colonies were picked from agarose plates and grown in 96-deep-well plates (Beckman Coulter, Inc., Fullerton, Calif.). Each well in the deep-well plate can hold up to 2 mL culture, but only 0.3 mL of growth culture was used to promote good mixing on the shaker. Each plate was covered with sterile aluminum foil and grown on a shaker at 300 RPM at 36° C. for 5–16 hours. After growth, 25 μL of cell culture was transferred to a Millipore MultiScreen 96-well plate (Millipore, Bedford, Mass.). The bottom of the MultiScreen plate has a 0.22 μm pore size Durapore membrane. This prevents passage of *E. coli* cells through the membrane but allows removal of the growth medium by vacuum. The cells were then washed with 50 mM Tris-HCl (pH 8.5) using a Biomek2000 Laboratory Automation Workstation (Beckman Coulter, Inc., Fullerton, Calif.). To measure the TAL activity, 100 μL of 0.5 mM tyrosine in washing buffer was added to each well. After incubation of the plate on the shaker at room temperature for 5–12 hours, the reaction solution was separated from the cells and transferred into a Coster 96-well UV plate (Corning, Corning, N.Y.) by applying vacuum using Biomek2000. The plate is now ready for detection.

The same procedure was used to measure PAL activity except 0.5 mM phenylalanine was used for the reaction. The TAL and PAL activities can be measured simultaneously by making duplicate plates from the cell culture; or the TAL activity can be measured first. After filtration of the reaction solution into the UV plate, the MultiScreen plate which still contains the *E. coli* cells was washed and phenylalanine solution was added into each well for PAL activity measurement. Both approaches worked well.

For detection, the formation of PHCA or cinnamate can be easily detected by measuring absorption at 290 or 270 nm, respectively. Tyrosine and phenylalanine do not have strong absorption at these wavelengths. Measurements were made on a SpectraMAX190 96-well plate reader (Molecular Devices Corp., Sunnyvale, Calif.). Each plate contained a negative control (*E. coli* cells containing the expression vector only) and a positive control (*E. coli* cells with mutant PAL gene expressed). The absorption difference between negative and positive control generally was 10 fold. Such signal to noise levels gives reliable results.

Cell growth rate and enzyme expression level in each well are not always the same. This produces variations in the assay results. To eliminate this variability, the TAL/PAL ratio was calculated after exporting TAL and PAL data to Microsoft Excel. We found the TAL/PAL ratio of the positive control to be quite consistent (variation always less than 20%). The method described here is quite simple, and enables screening of several thousands of clones per day, when colonies are manually picked. With the robot colony picker, the throughput can be easily increased 5 to 10 fold. Also, this method can be used for any other types of cells in addition to *E. coli* (e.g., yeast cells).

Example 21

Homology Modeling of Mutant PAL Enzyme

Figure 5:
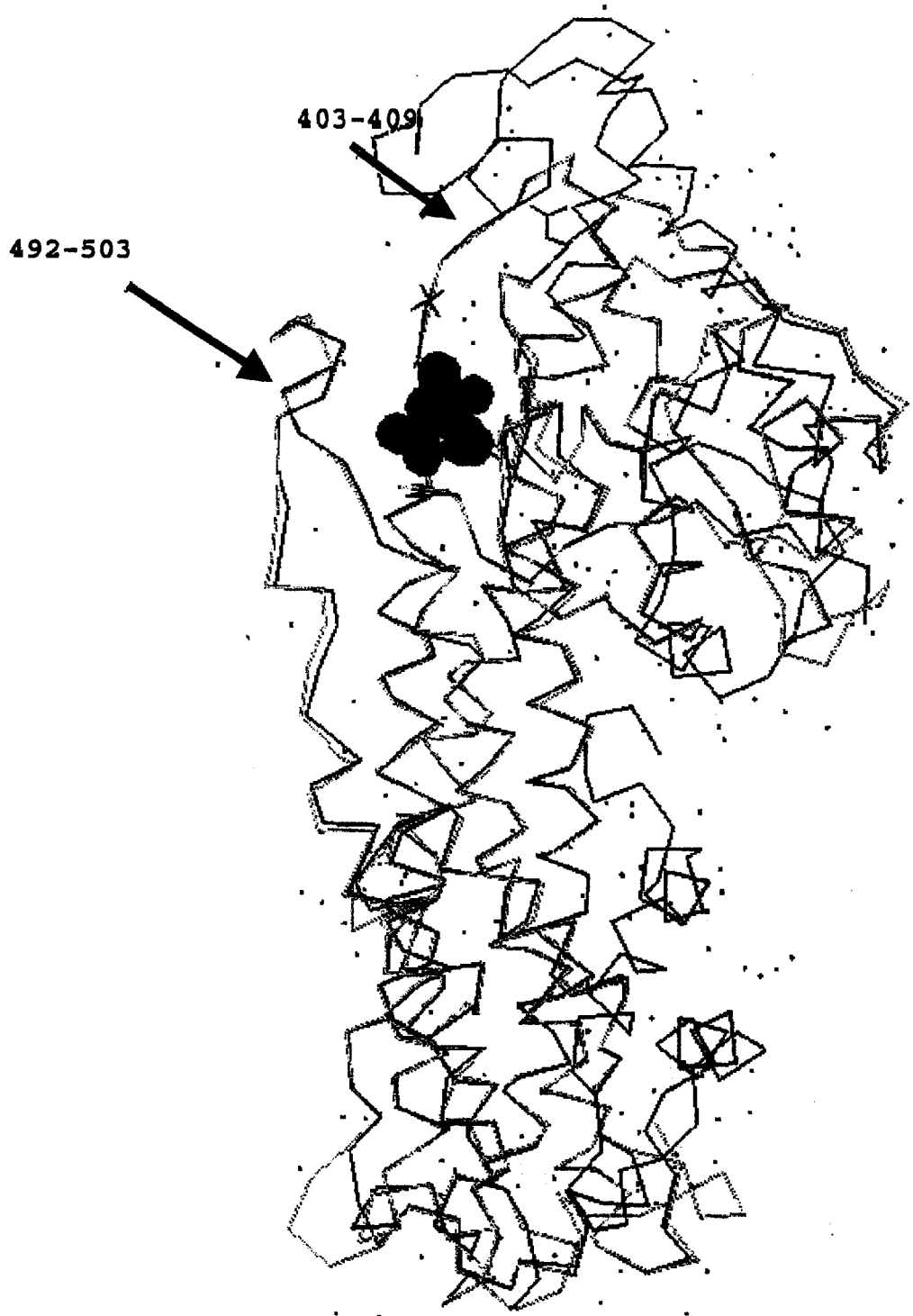
FIG. 5 is a homology model of the histidine ammoniumlyase enzyme and the PAL/TAL enzyme.

Although no crystal structure is presently available for the PAL/TAL enzyme, the crystal structure of histidine ammonia-lyase (HAL), which shows ~40% homology to PAL/TAL, has been solved by Schwede et al. (*Biochemistry* 38: 5355–5361 (1999)). Based on the crystal structure of HAL, a homology model for the PAL/TAL enzyme was built using the SWISS-MODEL server (Peitsch, M. C. *Bio/Technology* 13: 658–660(1995); Peitsch, M. C. *Biochem. Soc. Trans.* 24: 274–279(1996); Guex et al. *Electrophoresis* 18: 2714–2723(1997)). An overlap of HAL with the homology model of PAL/TAL is shown in FIG. 5. Histidine Ammonia-Lyase is colored in red, while the PAL/TAL enzyme is white. The spacefilling model is the active site prosthetic group 4-methylidene-imidazole-5-one. Both HAL and PAL/TAL appear to function as a tetramer. As revealed by the crystal structure of HAL, the active site consists of residues from three subunits (Schwede et al. *Biochemistry* 38: 5355–5361 (1999)).

The PAL/TAL sequence is much longer than the HAL sequence in our homology modeling by 208 amino acids. Due to the rather limited homology between PAL/TAL and HAL, the PAL/TAL's homology model does not include the first 150 amino acids. However, since HAL's N-terminus is involved in the formation of the substrate-binding pocket, it is highly likely that some portion of the first 150 N-terminal amino acids of PAL/TAL also contribute to binding pocket formation. Indeed, the results from our N-terminal truncation experiments (Example 18) and regional mutagenesis (Example 22) appear to support this notion.

The homology model has proven to be a valuable structural frame to rationalize observed mutations and more importantly to select potential regions for further mutagenesis experiments. The region around amino acid No. 556 of the second subunit contributes to the active site formation. The Ile540Thr mutation, found in EP18Km6 is not far from this region.

Example 22

Regional Random Mutagenesis Targeting Amino Acid No. 120–280

To further improve the mutant PAL gene (EP18Km-6) and to investigate other important regions for TAL activity in mutant PAL, we performed regional mutagenesis on the gene. Ser212 has been demonstrated to be involved in catalysis by site-directed mutagenesis and other works (Hanson et al., *Arch. Biochem. Biophys.* 141:1–17 (1970); Langer et al., *Biochemistry*, 36:10867–10871 (1997)). On this basis, the first region targeted for mutagenesis was from amino acids No. 120 to No. 280.

Error-Prone PCR:

There are two unique restriction enzyme sites, BamHI and ClaI, in the pET17b-Km6 construct. BamHI cuts the mutant PAL gene at base pair No. 352, and ClaI at base pair No.829. This covers from amino acid No. 120 to 280. The following primers were used for amplifying part (from 5'-end to base pair No. 960) of the mutant PAL gene from pET17b-Km6:

Primer A (SEQ ID NO: 5):
5'-TAGCTCTAGAATGGCACCCTCG-3'

18EP-3 primer (SEQ ID NO: 24):
5'-CGCGTGACGTCGTGAAGGAA-3'

The error-prone PCR was performed as described in Example 9, with pET17b-Km6 plasmid DNA as template. The error-prone PCR product was a 960 base pair DNA fragment, from 5'-end to base pair No. 960 of mutant PAL gene. The BamHI-ClaI fragment can be obtained by restriction enzyme digestion of the PCR product.

Making Regional Mutant Library:

The error-prone PCR product was loaded onto a 1% agarose gel, the 960 base pair DNA fragment was gel purified (Qiagen's PCR clean-up kit, according to manufacturer's instruction), and eluted with 50 μL of EB buffer. 30 μL of error-prone PCR fragment was digested in 10× multibuffer (6 μL), NheI (2 μL), EcoRI (2 μL) and distilled deionized water (20 μL). After incubation at 37 C. for 2 hrs, the reaction mixture was loaded onto a 1% agarose gel. The BamHI/ClaI-digested DNA fragment was purified using Promega's PCR clean-up kit.

50 μL of pET17b-Km6 plasmid DNA was digested at 37 C. for 2 hrs in 10 μL of 10× multibuffer, 3 μL of BamI, 3 μL of ClaI, and 34 μL of distilled deionized water. The digestion mixture was loaded onto a 1% agarose gel, and the 4.9 kb DNA fragment was gel purified with Promega DNA clean-up kit. This digestion linearized the construct and removed 477 base pairs (from base pair No. 352 to 829) from the mutant PAL gene.

The BamHI/ClaI-digested error-prone fragment was ligated into BamHI/ClaI-digested pET17b-Km6 in a ligation mixture containing 35 µL of PCR fragment, 5 µL of linearized pET17b-Km6, 5 µL of 10× ligation buffer, 3 µL T4 ligase (3 U/µL) and 2 µL of distilled deionized water. The ligation mixture was incubated at 15 C. for 2 hrs. The regional mutant library was obtained by transforming the ligation mixture into BL21(DE3) E. coli cells, as described in Example 17.

Screening the Mutant Library and Characterizing the Mutant:

5,000 mutant colonies were picked from agarose plates and screened by high throughput assay (Example 20). The initial hits were further investigated by a follow-up assay to confirm screening results. The TAL and PAL activities were measured using the whole cell assay, described in Example 17, and then ratio of TAL/PAL activities was calculated. The following table summarizes results of the follow-up assay for four mutants with altered TAL/PAL ratios:

TABLE 17

Ratio of TAL and PAL activities in regional mutants

| Strain | TAL/PAL ratio |
|---|---|
| Mutant PAL (starting gene)* | 1.7 |
| RM120-1 | 7.2 |
| RM120-2 | 2.1 |
| RM120-4 | 2.0 |
| RM120-7 | 0.8 |

*pET17b-Km6 in BL21(DB3) E. coli cells.

Although our goal was to find mutants with higher TAL/PAL ratios than the starting gene, mutants with lower TAL/PAL ratios are also interesting. Both types of mutation reveal important information about how the enzyme binds tyrosine and phenylalanine differentially. As shown in the Table, in RM120-7 the TAL/PAL ratio has been largely decreased. In contrast, the TAL/PAL ratio in RM120-1 has been improved more than 4-fold compared with Km-6. Since the mutant PAL already has an improved TAL/PAL ratio compared to wild type yeast PAL enzyme (TAL/PAL ratio is 0.5), mutant RM120-1 exhibited greater than 14-fold improvement in TAL/PAL activity as compared to wild type PAL.

Sequence Analysis of the Mutants:

Plasmid DNA was purified from these mutants using Qiagen plasmid MiniPrep kit. The mutant genes were sequenced on an ABI377 automated sequencer (Applied Biosystem, Foster City, Calif.), and the data managed using DNAstar program (DNASTAR Inc., Madison, Wis.). Analysis of the mutants, followed by comparison with the wild type yeast PAL gene, indicated that the mutant genes contained the following single base substitution mutations (point mutations):

TABLE 18

DNA sequence analysis of regional mutants

| Strain | Mutations |
|---|---|
| RM120-1 | GAC(Asp126) to GGC(Gly) |
| | CAG(Gln138) to CTG(Leu) |
| | CTG(Leu215) to CTC(Leu)* |
| | GAA(Glu264) to GAG(Glu) |
| | GCT(Ala286) to GCA(Ala) |
| | ATC(Ile540) to ACC(Thr) |

TABLE 18-continued

DNA sequence analysis of regional mutants

| Strain | Mutations |
|---|---|
| RM120-2 | TTG(Leu176) to CTG(Leu) |
| | GGC(Gly198) to CAC(Asp) |
| | CTG(Leu215) to CTC(Leu)* |
| | GAA(Glu264) to GAG(Glu) |
| | GCT(Ala286) to GCA(Ala) |
| | ATC(Ile540) to ACC(Thr) |
| RM120-4 | TCG(Ser181) to CCG(Pro) |
| | GTC(Val235) to GCC(Ala) |
| | CTG(Leu215) to CTC(Leu) |
| | GAA(Glu264) to GAG(Glu) |
| | GCT(Ala286) to GCA(Ala) |
| | ATC(Ile540) to ACC(Thr) |
| RM120-7 | TCG(Ser149) to CCG(Pro) |
| | ATC(Ile202) to GTC(Val) |
| | CTG(Leu215) to CTC(Leu) |
| | GAA(Glu264) to GAG(Glu) |
| | GCT(Ala286) to GCA(Ala) |
| | ATC(Ile540) to ACC(Thr) |

*The mutations indicated in bold letters were from the starting mutant PAL gene (EP18Km-6).

Since the mutant PAL gene (EP18Km-6) was used as the starting gene, four point mutations in the mutant PAL were also present in these regional mutant (indicated in bold letters in Table 18). Three of the four mutations were silent mutations that didn't result in any amino acid change. The ATC to ACC mutation has changed the isoleucine-540 to threonine. In addition to these mutations, RM120-2 contained an additional amino acid substitution and one silent mutation, while RM120-1, RM120-4 and RM120-7 all contained two additional amino acid substitutions. The affects of these amino acid substitutions were shown above in the altered TAL/PAL ratios of each mutant.

The N-terminus of histidine ammonia-lyase (HAL) is proposed to function in the formation of the substrate-binding pocket (Schwede et al. Biochemistry 38: 5355–5361 (1999)). Based on the homology of PAL to HAL, it is likely that the PAL N-terminus plays a similar role. We have shown in Example 18 that the N-terminus of mutant PAL is important for TAL activity. The two mutations found in RM120-1 (Asp126Gly and Gln138Leu) further support this hypothesis. At least one of the mutation sites could be quite close to the substrate-binding pocket.

Our results indicate that amino acid region 120 to 280 is very important for enzyme substrate specificity. To improve the TAL activity of the PAL enzyme, this is one of the ideal regions for protein engineering.

Example 23

Regional Random Mutagenesis Targeting Amino Acids No. 350–361, 492–503 and 556–564

By comparing the homology model of mutant PAL to the crystal structure of HAL (Schwede et al. Biochemistry 38: 5355–5361 (1999)), we chose the following regions for regional random mutagenesis: 1) amino acids No. 350–361; 2) amino acids No. 492–503 and 3) amino acids No. 556–564. Since all of these regions are quite short, an oligo-directed mutagenesis approach was used to make a mutant library.

Designing and Synthesizing the Degenerate Oligonucleotides:

The following degenerate olignucleotide primers were designed and synthesized for oligo-directed mutagenesis:
RM350-F2 (SEQ ID NO.25):

5'-GAGGAGGTCAAGGTCAAGGACGACGAGGGCA
TTCTCCGCCAGGACCGCTACCCC-3'
RM350-R1 (SEQ ID NO. 26):
5'-GGGGATGCGGTCCTGGCGGAGAATGCCCTCGTC
GTCCTTGACCTTGACCTCCTC-3'
RM492-F2 (SEQ ID NO.27):
5'-ACGACGCATGTCCAGCCGGCTGAGATGGCGAAC
CAGGCGGTCAACTCGCTTGCG-3'
RM492-R1 (SEQ ID NO.28):
5'-CGCAAGCGAGTTGACCGCCTGGTTCGCCATCTC
AGCCGGCTGGACATGCGTCGT-3'
RM556-F2 (SEQ ID NO.29):
5'-GTCTCGCTCATCGACCAGCACTTTGGCTCCGCC
ATGACCGGCTCG-3'
RM556-R1 (SEQ ID NO.30):
5'-CGAGCCGGTCATGGCGGAGCCAAAGTGCTGGT
CGATGAGCGAGAC-3'

Primers RM350-F2 and RM350-R1 are for regional mutagenesis between amino acids No. 350–361, RM492-F2 and RM492-R1 for region 492–503, and RM556-F2 and RM556-R1 for region 556–564. The primers labeled with F2 are forward primers, while those labeled R1 are reverse primers. Each set of primers is complementary to each other. The bases in bold text encode the region for mutagenesis. Nine extra nucleotides were included on both 5'- and 3'-ends around the targeted region for mutagenesis and normal oligo synthesis conditions were used for those bases.

Bases in bold text must be doped with non-wild type (WT) nucleotides. The following special bases were used for synthesis of RM350-F2, RM350-R1, RM492-F2 and RM492-R1:

A (50 mM) mixed with 0.73 mM G, 0.73 mM C and 0.73 mM T

G (50 mM) mixed with 0.73 mM A, 0.73 mM C and 0.73 mM T

C (50 mM) mixed with 0.73 mM A, 0.73 mM G and 0.73 mM T

T (50 mM) mixed with 0.73 mM A, 0.73 mM G and 0.73 mM C

The resulting nucleotide mixture in the synthesis chamber therefore contained 1.4% each of the three non-WT nucleotides and 95.8% WT, resulting in a misincorporation rate of 0.042/nucleotide. Since the region targeted for misincorporation was 36 bases, this would result in an average of 1.5 misincorporations (non-WT nucleotides) per oligomer, a level that maximizes the proportion of one and two-base substitutions in the resulting pool of degenerate oligomers.

For RM556-F2 and RM556-R1, the region targeted for misincorporation was 27 bases. The following special bases were used for synthesizing the bases wrote in bold text:

A (50 mM) mixed with 0.98 mM G, 0.98 mM C and 0.98 mM T

G (50 mM) mixed with 0.98 mM A, 0.98 mM C and 0.98 mM T

C (50 mM) mixed with 0.98 mM A, 0.98 mM G and 0.98 mM T

T (50 mM) mixed with 0.98 mM A, 0.98 mM G and 0.98 mM C

Again, this would result in an average of 1.5 misincorporation per oligomer.

Making Mutant DNA Fragments by PCR:

The following normal oligo primers were also used for making mutant DNA fragments:

Primer A (SEQ ID NO:5):
5'-TAGCTCTAGAATGGCACCCTCG-3'
Primer B (SEQ ID NO:6):
5'-AACTGCAGCTAAGCGAGCATC-3'

Two PCR reactions were prepared for amino acid No. 350–361 regional mutagenesis. Primer sets used were: primer A (forward primer)/RM350-R1 (reverse primer) and RM350-F2 (forward primer)/primer B (reverse primer). Template DNA was EP18Km-6 plasmid and HotStart Taq (Promega, Madison, Wis.) was used as the polymerase. PCR was carried out for 25 cycles with a 95 C. hot start for 10 min, a 94 C. melting temperature for 30 sec, a 45 C. annealing temperature for 1 min, and 72 C. elongation temperature for 2 min. The PCR products were then purified (Qiagen PCR Quicken Spin kit, according manufacturer's instruction). The ends of PCR fragments were polished in a polishing reaction mixture containing 50 μL of PCR product, 2 μL of 2 mM dNTPs, 2 μL of Pfu enzyme (5 U/μL) (Stratagen, La Jolla, Calif.) and 6 μL of 10× Pfu buffer. The polishing reaction mixtures were incubated at 72° C. for 30 min. Since both PCR products overlapped each other, the two fragments were then combined and the full-length gene (2.15 kb) was obtained by 3' extension and amplification with the outer set of primers. A touch down PCR reaction was carried out in a reaction mixture containing the two polished PCR fragments (10 μL each), 1 μL of expand Taq polymerase (Boehringer Manheim, Indianapolis, Ind.), 7 μL of 10× buffer, 3 μL of primer A, 3 μL of primer B and 60 μL of distilled deionized water. The following touch down PCR conditions were used:

94° C. for 1 min, 60° C. for 1 min, 68° C. for 4 min, 3 cycles;

94° C. for 1 min, 58° C. for 1 min, 68° C. for 4 min, 3 cycles;

94° C. for 1 min, 56° C. for 1 min, 68° C. for 4 min, 3 cycles;

94° C. for 1 min, 54° C. for 1 min, 68° C. for 4 min, 3 cycles;

94° C. for 1 min, 52° C. for 1 min, 68° C. for 4 min and 15 sec, 3 cycles;

94° C. for 1 min, 50° C. for 1 min, 68° C. for 4 min and 30 sec, 3 cycles.

The touch down PCR product was loaded onto a 1% agarose gel, and the 2.15 kb DNA band was purified from the gel using Qiagen Quicken Spin kit. This 2.15 kb fragment contains the full-length PAL gene from 5'-end to 3'-end, and the region corresponding to amino acid No. 350–361 was randomly mutagenized.

The same experiments were carried out using primer A/RM492-R1 and RM492-F2/primer B for amino acid No. 492–503 regional mutagenesis, and using primer A/RM556-R1 and RM556-F2/primer B for amino acid No. 556–564 regional mutagenesis. For each case, a full-length gene in which the desired region was randomly mutagenized was obtained.

Making the Regional Mutant Libraries:

In addition to the unique restriction enzyme ClaI (cleaves mutant PAL gene at base pair No. 829; see Example 21), two other unique sites cut pET17b-Km6: NcoI and SacI at base pairs No. 1262 and 1718, respectively. These three sites were used for library construction.

To make regional mutagenesis library for amino acid No. 350–361, the above-mentioned 2.15 kb fragment was digested with ClaI and NcoI to generate a 434 bp DNA fragment. This fragment was then ligated into ClaI/NcoI-digested pET17b-Km6 vector. The mutant library was obtained by transforming the ligation mixture into BL21 (DE3) *E. coli* cells. The other two libraries were made at same way except NcoI-SacI were used instead of ClaI-NcoI.

Screening the Mutant Library and Characterizing the Mutant:

A total of 5,000 mutant colonies from these three libraries were screened by high throughput assay (Example 20). Initial hits were further investigated by a follow-up HPLC assay to confirm the screening results as described in Example 21. One mutant with improved TAL/PAL ratio was found (Table 19).

TABLE 19

Ratio of TAL and PAL activities in a regional mutant

| Strain | TAL/PAL ratio |
| --- | --- |
| Wild type* | 0.5 |
| Mutant PAL (starting gene)** | .7 |
| RM492-4 | .0 |

*PCA18Km in XL1-Blue *E. coli* cells.
**pET17b-Km6 in BL12l (DE3) *E. coli* cells.

This result suggests that amino acid region 492–503 is important for TAL activity. Although mutants with improved TAL activity in the amino acid No. 350–361 and 556–564 regional mutant libraries were not found in the 5,000 clones screened, many mutants in these two libraries showed decreased TAL activity indicating the role of these two regions for TAL activity.

Sequence Analysis for RM492-4 Mutant:

Plasmid DNA was purified using Qiagen plasmid Mini-Prep kit and the mutant gene was sequenced on an ABI377 automated sequencer. Analysis of the mutant followed by comparison with the wild type yeast PAL gene indicated five base substitution mutations (point mutations) in mutant RM492-4: GTC(Val502) to GGC(Gly), CTG(Leu215) to CTC(Leu), GAA(Glu264) to GAG(Glu), GCT(Ala286) to GCA(Ala) and ATC(Ile540) to ACC(Thr). Except the first mutation, GTC(Val502) to GGC(Gly), all others were from the starting mutant PAL gene (EP18Km-6). This first mutation is responsible for the resulting change in TAL/PAL ratio. Val502 is proposed to be present on the substrate-binding pocket in the homology model. Changing valine to glycine at this site would make the substrate-binding pocket larger and thus easier for tyrosine to bind, since tyrosine is larger than phenylalanine, the original substrate.

What is claimed is:

1. An isolated nucleic acid fragment selected from the group consisting of:

a) an isolated nucleic acid fragment encoding a mutant tyrosine ammonia lyase polypeptide, the polypeptide having an amino acid sequence as set forth in SEQ ID NO:34; and b) an isolated nucleic acid fragment completely complementary to (a).

* * * * *